US010995336B2

(12) United States Patent
Schlegel et al.

(10) Patent No.: US 10,995,336 B2
(45) Date of Patent: May 4, 2021

(54) SERPINA1 IRNA COMPOSITIONS AND METHODS OF USE THEREOF

(71) Applicant: Alnylam Pharmaceuticals, Inc., Cambridge, MA (US)

(72) Inventors: Mark K. Schlegel, Boston, MA (US); Maja Janas, Cambridge, MA (US); Vasant R. Jadhav, Sharon, MA (US); Donald Foster, Attleboro, MA (US); Muthiah Manoharan, Weston, MA (US); Kallanthottathil G. Rajeev, Wayland, MA (US); Alexander V. Kel'in, Cambridge, MA (US); Klaus Charisse, Acton, MA (US); Jayaprakash K. Nair, Cambridge, MA (US); Martin A. Maier, Belmont, MA (US); Shigeo Matsuda, Cambridge, MA (US); Muthusamy Jayaraman, Cambridge, MA (US); Alfica Sehgal, Medford, MA (US); Christopher Brown, Cambridge, MA (US); Kevin Fitzgerald, Brookline, MA (US); Stuart Milstein, Arlington, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/420,263

(22) Filed: May 23, 2019

(65) Prior Publication Data

US 2019/0316127 A1 Oct. 17, 2019

Related U.S. Application Data

(63) Continuation of application No. PCT/US2017/062701, filed on Nov. 21, 2017.

(60) Provisional application No. 62/561,514, filed on Sep. 21, 2017, provisional application No. 62/549,099, filed on Aug. 23, 2017, provisional application No. 62/548,589, filed on Aug. 22, 2017, provisional application No. 62/425,907, filed on Nov. 23, 2016.

(51) Int. Cl.
*C12N 15/113* (2010.01)

(52) U.S. Cl.
CPC ........ *C12N 15/113* (2013.01); *C12N 2310/14* (2013.01); *C12N 2310/315* (2013.01); *C12N 2310/351* (2013.01)

(58) Field of Classification Search
CPC .............. C12N 15/113; C12N 2310/14; C12N 2310/315; C12N 2310/351; C12N 2310/31; A61P 43/00; A61P 35/00; A61P 1/16
See application file for complete search history.

(56) References Cited

U.S. PATENT DOCUMENTS

| | | | |
|---|---|---|---|
| 7,691,997 B2 | 4/2010 | Khvorova et al. |
| 9,574,192 B2 | 2/2017 | Sehgal et al. |
| 9,879,261 B2 | 1/2018 | Sehgal et al. |
| 10,030,244 B2 | 7/2018 | Sehgal et al. |
| 10,370,655 B2 | 8/2019 | Brown et al. |
| 2005/0137153 A1 | 6/2005 | McSwiggen et al. |
| 2005/0245475 A1 | 11/2005 | Khvorova et al. |
| 2006/0234247 A1 | 10/2006 | Puttaraju et al. |
| 2015/0087691 A1 | 3/2015 | Monia et al. |
| 2018/0195069 A1 | 7/2018 | Li et al. |

FOREIGN PATENT DOCUMENTS

| | | | |
|---|---|---|---|
| EP | 1752536 A1 | 2/2007 |
| WO | WO-2004/045543 A2 | 6/2004 |
| WO | WO-2006/006948 A2 | 1/2006 |
| WO | WO-2009/073809 A2 | 6/2009 |
| WO | WO-2009/120878 A2 | 10/2009 |
| WO | WO-2009/134487 A2 | 11/2009 |
| WO | WO-2010/148013 A2 | 12/2010 |
| WO | WO-2012/178033 A2 | 12/2012 |
| WO | WO-2014/190137 A1 | 11/2014 |
| WO | WO-2016/028649 A1 | 2/2016 |

OTHER PUBLICATIONS

Harborth et al. (2001) J. Cell Science 114:4557-4565. (Year: 2001).*
Holen et al. (2002) Nucleic Acids Res. 30:1757-1766. (Year: 2002).*
Boese et al., (2005) Methods in Enzymology 392:73-96. (Year: 2005).*
Reynolds et al., (2004) Nature Biotechnology 22:326-330. (Year: 2004).*
International Search Report and Written Opinion from PCT/US2014/039109 dated Oct. 21, 2014.
Sehgal, Alfica, et al. "Developing and RNAi Therapeutic for Liver Disease Associated with Alpha-1-Antitrypsin Deficiency", Hepatology, vol. 58, No. SI, Oct. 15, 2013, p. 412A.
GenBank Acession AC_235087; Jun. 24, 2009 [online] downloaded from: http://www.ncbi.nlm.nih.gov/nuccore/226938113/ on Jan. 18, 2017.

(Continued)

*Primary Examiner* — J. E. Angell

(74) *Attorney, Agent, or Firm* — McCarter & English, LLP; Maria Laccotripe Zacharakis; Deborah L. Nagle

(57) ABSTRACT

The invention relates to RNAi agents, e.g., double stranded RNAi agents, targeting the Serpina1 gene, and methods of using such RNAi agents to inhibit expression of Serpina1 and methods of treating subjects having a Serpina1 associated disease, such as a liver disorder.

41 Claims, 3 Drawing Sheets

Specification includes a Sequence Listing.

(56) References Cited

OTHER PUBLICATIONS

GenBank Acession M_26123; Oct. 30, 1994 [online] downloaded from: http://www.ncbi.nlm.nih.gov/nuccore/177815/ on Jan. 18, 2017.
GenBank Acession BC_011991; Jul. 15, 2006 [online] downloaded from: http://www.ncbi.nlm.nih.gov/nuccore/15080498/ on Jan. 18, 2017.
GenBank Acession DQ_682455; Jul. 22, 2006 [online] downloaded from: http://www.ncbi.nlm.nih.gov/nuccore/110350938/ on Jan. 18, 2017.
GenBank Acession CU_680153; Feb. 19, 2008 [online] downloaded from: http://www.ncbi.nlm.nih.gov/nuccore/Cu680153/ on Jan. 18, 2017.
GenBank Acession GZ_281832; Jun. 4, 2012 [online] downloaded from: http://www.ncbi.nlm.nih.gov/nuccore/389820151/ on Jan. 18, 2017.
GenBank Acession HV_439167; Sep. 27, 2011[online] downloaded from: http://www.ncbi.nlm.nih.gov/nuccore/hv439167/ on Jan. 18, 2017.
GenBank Acession HC_680729; May 13, 2010 [online] downloaded from: http://www.ncbi.nlm.nih.gov/nuccore/HC680729 on Jan. 18, 2017.
GenBank Acession DM_075322; Apr. 21, 2009 [online] downloaded from: http://www.ncbi.nlm.nih.gov/nuccore/DM075322 on Jan. 18, 2017.
GenBank Acession GC_604704; Dec. 10, 2008 online] downloaded from: http://www.ncbi.nlm.nih.gov/nuccore/217168445/ on Jan. 18, 2017.
GenBank Acession EA_307422; Dec. 14, 2007 [online] downloaded from: http://www.ncbi.nlm.nih.gov/nuccore/162460313/ on Jan. 18, 2017.
GenBank Acession DL_143111; Sep. 26, 2008 [online] downloaded from: http://www.ncbi.nlm.nih.gov/nuccore/DL143111 on Jan. 18, 2017.
GenBank Acession BD_472318; Nov. 4, 2005 [online] downloaded from: http://www.ncbi.nlm.nih.gov/nuccore/BD472318 on Jan. 18, 2017.
GenBank Acession CS_273919; Jul. 17, 2006 [online] downloaded from: http://www.ncbi.nlm.nih.gov/nuccore/CS273919 on Jan. 18, 2017.
GenBank Acession AR_791176; Apr. 5, 2006 [online] downloaded from: http://www.ncbi.nlm.nih.gov/nuccore/91138047/ on Jan. 18, 2017.
GenBank Acession AR_583727; Dec. 15, 2004 [online] downloaded from: http://www.ncbi.nlm.nih.gov/nuccore/56621150 on Jan. 18, 2017.
GenBank Acession CQ_896528; Nov. 5, 2004 [online] downloaded from: http://www.ncbi.nlm.nih.gov/nuccore/CQ896528 on Jan. 18, 2017.
GenBank Acession CQ_541805; Jan. 30, 2004 [online] downloaded from: http://www.ncbi.nlm.nih.gov/nuccore/CQ541805 on Jan. 18, 2017.
GenBank Acession CQ_663228; Feb. 3, 2004 [online] downloaded from: http://www.ncbi.nlm.nih.gov/nuccore/CQ663228 on Jan. 18, 2017.
GenBank Acession AX_616365; Feb. 20, 2003 [online] downloaded from: http://www.ncbi.nlm.nih.gov/nuccore/AX616365 on Jan. 18, 2017.
GenBank Acession AR_044165; Sep. 29, 1999 [online] downloaded from: http://www.ncbi.nlm.nih.gov/nuccore/5965630 on Jan. 18, 2017.
GenBank Acession GU_727620; Jan. 11, 2011 [online] downloaded from: http://www.ncbi.nlm.nih.gov/nuccore/317040113/ on Jan. 18, 2017.
Cruz et al., "In vivo post-transcriptional gene silencing of a-1 antitrypsin by adeno-associated virus vectors expressing siRNA", Laboratory Investigation (2007) 87, 893-902.
Reynolds et al., "Rational siRNA design for RNA interference," Nature Biotechnology, vol. 22, pp. 326-330, 2004.
Fairbanks et al., "Liver Disease in Alpha 1—Antitrypsin Deficiency: A Review", Am J Gastroenterol 2008;103:2136-2141.
U.S. Appl. No. 14/284,745 U.S. Pat. No. 9,574,192, filed May 22, 2014 Feb. 21, 2017, US 20140350071, Granted.
U.S. Appl. No. 15/399,820 U.S. Pat. No. 10,030,244, filed Jan. 6, 2017 Jul. 24, 2018, US 20170114342, Granted.
U.S. Appl. No. 16/008,461, filed Jun. 14, 2018, US 20180346910, Published.
U.S. Appl. No. 16/679,691, filed Nov. 11, 2019, Pending.

* cited by examiner

SERPINA1 IRNA COMPOSITIONS AND METHODS OF USE THEREOF

RELATED APPLICATIONS

This application is a 35 § U.S.C. 111(a) continuation application which claims the benefit of priority to PCT/US2017/062701, filed on Nov. 21, 2017, which claims the benefit of priority to U.S. Provisional Application No. 62/425,907, filed on Nov. 23, 2016; U.S. Provisional Application No. 62/548,589, filed on Aug. 22, 2017; U.S. Provisional Application No. 62/549,099, filed on Aug. 23, 2017; and U.S. Provisional Application No. 62/561,514, filed on Sep. 21, 2017. The entire contents of each of the foregoing applications are hereby incorporated herein by reference.

This application is related to U.S. Provisional Application No. 61/826,125, filed on May 22, 2013, U.S. Provisional Application No. 61/898,695, filed on Nov. 1, 2013; U.S. Provisional Application No. 61/979,727, filed on Apr. 15, 2014; U.S. Provisional Application No. 61/989,028, filed on May 6, 2014; U.S. patent application Ser. No. 14/284,745, now issued as U.S. Pat. No. 9,574,192, issued on Feb. 21, 2017; U.S. patent application Ser. No. 15/399,820, filed on Jan. 6, 2017; and International Patent Application No. PCT/US2014/039109, filed on May 22, 2014. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on May 20, 2019, is named 121301-07802_SL.txt and is 128,971 bytes in size.

BACKGROUND OF THE INVENTION

Serpina1 encodes alpha-1-antitrypsin which predominantly complexes with and inhibits the activity of neutrophil elastase produced by hepatocytes, mononuclear monocytes, alveolar macrophages, enterocytes, and myeloid cells. Subjects having variations in one or both copies of the Serpina1 gene may suffer from alpha-1-antitrypsin deficiency and are at risk of developing pulmonary emphysema and/or chronic liver disease due to greater than normal elastase activity in the lungs and liver.

In affected subjects, the deficiency in alpha-1-antitrypsin is a deficiency of wild-type, functional alpha-1-antitrypsin. In some cases, a subject having a variation in one or both copies of the Serpina1 gene is carrying a null allele. In other cases, a subject having a variation in one or both copies of the Serpina1 gene is carrying a deficient allele.

For example, a subject having a deficient allele of Serpina1, such as the PIZ allele, may be producing misfolded proteins which cannot be properly transported from the site of synthesis to the site of action within the body. Such subjects are typically at risk of developing lung and/or liver disease. Subjects having a Serpina1 null allele, such as the PINULL (Granite Falls), are typically only at risk of developing lung disease.

Liver disease resulting from alpha-1 antitrypsin deficiency is the result of variant forms of alpha-1-antitypsin produced in liver cells which misfold and are, thus, not readily transported out of the cells. This leads to a buildup of misfolded protein in the liver cells and can cause one or more diseases or disorders of the liver including, but not limited to, chronic liver disease, liver inflammation, cirrhosis, liver fibrosis, and/or hepatocellular carcinoma.

There are currently very limited options for the treatment of patients with liver disease arising from alpha-1-antitrypsin deficiency, including hepatitis vaccination, supportive care, and avoidance of injurious agents (e.g., alcohol and NSAIDs). Although replacement alpha-1-antitrypsin therapy is available, such treatment has no impact liver disease in these subjects and, although liver transplantation may be effective, it is a difficult, expensive and risky procedure and liver organs are not readily available.

Accordingly, there is a need in the art for effective treatments for Serpina1-associated diseases, such as a chronic liver disease, liver inflammation, cirrhosis, liver fibrosis, and/or hepatocellular carcinoma.

SUMMARY OF THE INVENTION

As described in more detail below, disclosed herein are compositions comprising agents, e.g., RNAi agents, e.g., double stranded iRNA agents, targeting Serpina1. Also disclosed are methods using the compositions of the invention for inhibiting Serpina1 expression and for treating Serpina1 associated diseases, e.g., chronic liver disease, liver inflammation, cirrhosis, liver fibrosis, and/or hepatocellular carcinoma.

The present invention is based, at least in part on the discovery of effective nucleotide or chemical motifs for dsRNA agents targeting Serpina1 which are advantageous for inhibition of target gene expression, while having reduced off-target gene silencing effects, as well as compositions comprising such agents suitable for therapeutic use. More specifically, it has been discovered inter alia that dsRNA agents targeting Serpina1 where the antisense strand comprises at least one thermally destabilizing modification of the duplex within the seed region (i.e., at position 2-9 of the 5'-end of the antisense strand, counting from the 5'-end) and/or the dsRNA agent has a melting temperature in the range of from about 40° C. to about 80° C. can be more effective in mediating RNA interference than a parent dsRNA agent lacking the destabilizing modification.

Accordingly, in one aspect, the present invention provides a double stranded RNA (dsRNA) agent that inhibits expression of a serine peptidase inhibitor, clade A, member 1 (Serpina1) target gene sequence, comprising a sense strand and an antisense strand, wherein the antisense strand has sufficient complementarity to the target sequence to mediate RNA interference, wherein said antisense strand comprises at least one thermally destabilizing modification within the first 9 nucleotide positions of the 5' region or a precursor thereof, wherein said sense strand comprises an asialoglycoprotein receptor (ASGPR) ligand, and wherein each of the sense strand and the antisense strand are independently 14 to 40 nucleotides in length.

In another aspect, the present invention provides a double stranded RNA (dsRNA) agent that inhibits expression of a serine peptidase inhibitor, clade A, member 1 (Serpina1) gene, comprising a sense strand and an antisense strand forming a double stranded region, wherein the sense strand comprises at least 15 contiguous nucleotides differing by no more than 3 nucleotides from the nucleotide sequence of SEQ ID NO:1, and the antisense strand comprises at least 15 contiguous nucleotides differing by no more than 3 nucleotides from the nucleotide sequence of SEQ ID NO:15, wherein said antisense strand comprises at least one thermally destabilizing modification of the double stranded region within the first 9 nucleotide positions of the 5' region or a precursor thereof, wherein said sense strand comprises an asialoglycoprotein receptor (ASGPR) ligand, and wherein each of the sense strand and the antisense strand are independently 14 to 40 nucleotides in length.

In yet another aspect, the present invention provides a double stranded RNA (dsRNA) agent that inhibits expression of a serine peptidase inhibitor, clade A, member 1 (Serpina1) gene, comprising a sense strand and an antisense strand forming a double stranded region, said antisense strand comprising a region of complementarity to an mRNA encoding Serpina1, wherein the region of complementarity comprises at least 15 contiguous nucleotides differing by no more than 3 nucleotides from the nucleotide sequence of SEQ ID NO:15, wherein said antisense strand comprises at least one thermally destabilizing modification within the first 9 nucleotide positions of the 5' region or a precursor thereof, wherein said sense strand comprises an asialoglycoprotein receptor (ASGPR) ligand, wherein each of the sense strand and the antisense strand are independently 14 to 40 nucleotides in length.

In one embodiment, the dsRNA agent comprises at least four nucleotides comprising a 2'-fluoro modification.

In one embodiment, the dsRNA agent has the following characteristics: a) the thermally destabilizing modification is located in position 4-8 of the 5' region of the antisense strand; b) and each of the sense and antisense strands independently comprise at least two nucleotides comprising a 2'-fluoro modification; and c) an ASGPR ligand attached to either end of the sense strand.

In another embodiment, the antisense strand has at least two of the following characteristics: a) the thermally destabilizing modification is located in position 4 to 8 of the antisense strand; b) at least two nucleotides comprise a 2'-fluoro modification; c) a phosphorothioate internucleotide linkages between nucleotide positions 1 and 2 (counting from the 5' end); d) a length of 18 to 35 nucleotides.

In one embodiment, the sense strand has at least one of the following characteristics: a) the ASGPR ligand attached to either end of the sense strand; b) at least two nucleotides comprise a 2'-fluoro modification; c) the sense strand and the antisense strand form a double stranded region spanning at least 19 nucleotide positions and wherein the thermally destabilizing modification is located within said double stranded region.

In one embodiment, the thermally destabilizing modification is selected from the group consisting of

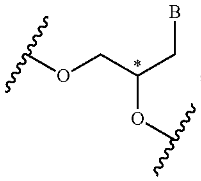
,
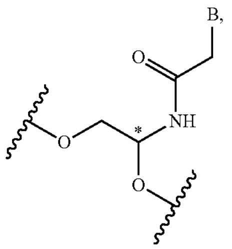
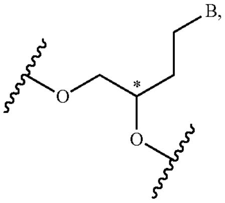
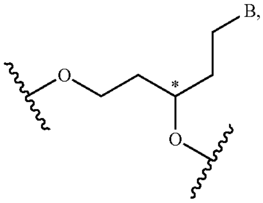
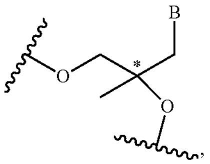
and
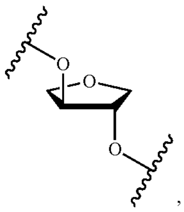
, wherein B is nucleobase.

In one embodiment, the destabilizing modification is located in position 7 of the antisense strand.

In one embodiment, the ASGPR ligand is one or more GalNAc derivatives attached through a bivalent or trivalent branched linker.

In one embodiment, the ASGPR ligand is:

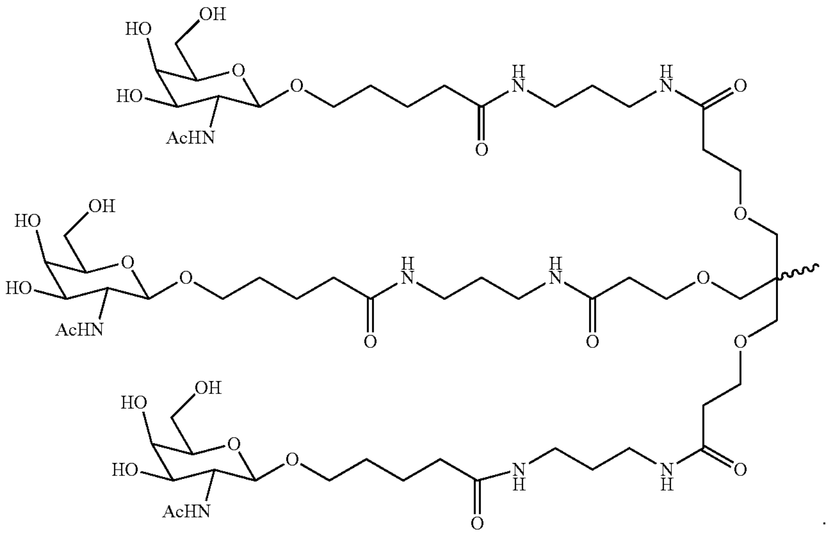 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
.

In one embodiment, the dsRNA agent is conjugated to the ligand as shown in the following schematic

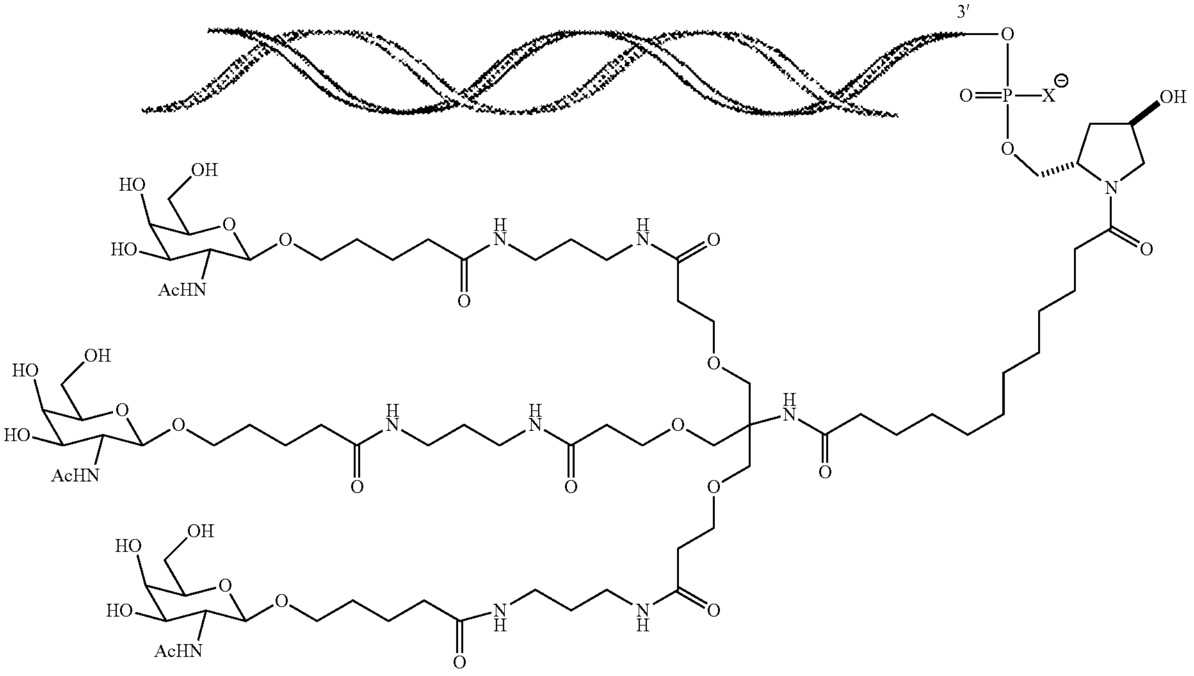

wherein X is O or S.

In one aspect, the present invention provides a double stranded RNA (dsRNA) agent that inhibits expression of a serine peptidase inhibitor, clade A, member 1 (Serpina1) target gene sequence, comprising a sense strand and an antisense strand, wherein the antisense strand has sufficient complementarity to a target sequence to mediate RNA interference, wherein the antisense strand comprises at least one thermally destabilizing modification within the first 9 nucleotide positions of the 5' region, wherein each of the sense strand and the antisense strand are independently 14 to 40 nucleotides in length, and wherein the dsRNA has a melting temperature of from about 40° C. to about 80° C.

In another aspect, the present invention provides a double stranded RNA (dsRNA) agent that inhibits expression of a serine peptidase inhibitor, clade A, member 1 (Serpina1) target gene sequence, comprising a sense strand and an antisense strand, wherein the sense strand comprises at least 15 contiguous nucleotides differing by no more than 3 nucleotides from the nucleotide sequence of SEQ ID NO:1, and the antisense strand comprises at least 15 contiguous nucleotides differing by no more than 3 nucleotides from the nucleotide sequence of SEQ ID NO:15, wherein the antisense strand comprises at least one thermally destabilizing modification within the first 9 nucleotide positions of the 5' region, wherein each of the sense strand and the antisense strand are independently 14 to 40 nucleotides in length, and wherein the dsRNA has a melting temperature of from about 40° C. to about 80° C.

In yet another aspect, the present invention provides a double stranded RNA (dsRNA) agent that inhibits expression of a serine peptidase inhibitor, clade A, member 1 (Serpina1) target gene sequence, comprising a sense strand and an antisense strand, said antisense strand comprising a region of complementarity to an mRNA encoding Serpina1, wherein the region of complementarity comprises at least 15 contiguous nucleotides differing by no more than 3 nucleotides from the nucleotide sequence of SEQ ID NO:15, wherein the antisense strand comprises at least one thermally destabilizing modification within the first 9 nucleotide positions of the 5' region, wherein each of the sense strand and the antisense strand are independently 14 to 40 nucleotides in length, and wherein the dsRNA has a melting temperature of from about 40° C. to about 80° C.

In one embodiment, the dsRNA agent has a melting temperature of from about 55° C. to about 67° C. In another embodiment, the dsRNA agent has a melting temperature of from about 60° C. to about 67° C.

In one embodiment, the dsRNA agent further comprises an asialoglycoprotein receptor (ASGPR) ligand.

In one embodiment, the ASGPR ligand is one or more GalNAc derivatives attached through a bivalent or trivalent branched linker.

In one embodiment, the ASGPR ligand is:

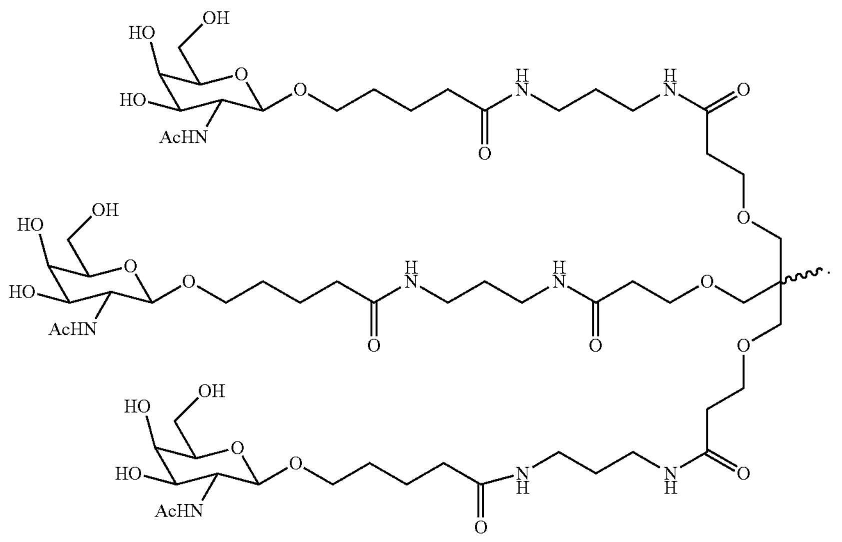 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one embodiment, the dsRNA agent is conjugated to the ligand as shown in the following schematic

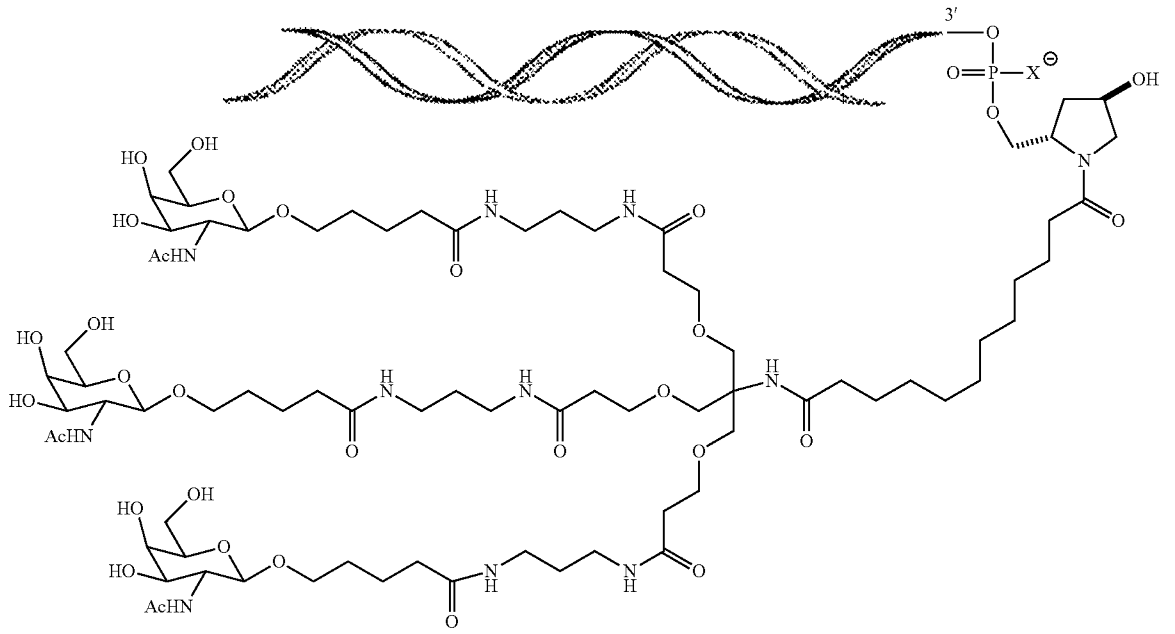

wherein X is O or S.

In one embodiment, the dsRNA agent further has at least one of the following characteristics: (i) the antisense strand comprises 2, 3, 4, 5 or 6 nucleotides comprising a 2'-fluoro modifications (ii) the antisense strand comprises 1, 2, 3 or 4 phosphorothioate internucleotide linkages; (iii) the sense strand is conjugated with a ligand; (iv) the sense strand comprises 2, 3, 4 or 5 nucleotides comprising a 2'-fluoro modification; (v) the sense strand comprises 1, 2, 3 or 4 phosphorothioate internucleotide linkages; (vi) the dsRNA comprises at least four nucleotides comprising a 2'-fluoro modification; (vii) the dsRNA comprises a double stranded region region of 12-40 nucleotide pairs in length; and (viii) a blunt end at 5'end of the antisense strand.

In some embodiment, each strand of the dsRNA agent may have 15-30 nucleotides, 19-30 nucleotides; or the sense strand may have 21 nucleotides, and the antisense strand may have 23 nucleotides.

In one embodiment, the antisense strand comprises a region of complementarity comprising at least 15 contiguous nucleotides differing by no more than 3 nucleotides from nucleotides 1440-1480 of SEQ ID NO:1; or nucleotides 1441-1479 of SEQ ID NO:1; or nucleotides 1442-1478 of SEQ ID NO:1; or nucleotides 1443-1477 of SEQ ID NO:1; or nucleotides 1444-1476 of SEQ ID NO:1; or nucleotides 1445-1475 of SEQ ID NO:1; or nucleotides 1446-1474 of SEQ ID NO:1; or nucleotides 1447-1473 of SEQ ID NO:1; or nucleotides 1448-1473 of SEQ ID NO:1; or nucleotides 1448-1472 of SEQ ID NO:1; or nucleotides 1448-1471 of SEQ ID NO:1; or nucleotides 1448-1470 of SEQ ID NO:1; or nucleotides 1447-1469 of SEQ ID NO:1; or nucleotides 1446-1478 of SEQ ID NO:1; or nucleotides 1449-1471 of SEQ ID NO:1; or nucleotides 1450-1472 of SEQ ID NO:1; or nucleotides 1440-1475 of SEQ ID NO:1; or nucleotides 1445-1480 of SEQ ID NO:1; or nucleotides 1445-1475 of SEQ ID NO:1.

In one embodiment, the region of complementarity comprises at least 15 contiguous nucleotides differing by no more than 3 nucleotides from the nucleotide sequence 5'-UUUUGUUCAAUCAUUAAGAAGAC-3' (SEQ ID NO: 419).

In one embodiment, the sense strand comprises the nucleotide sequence 5'-CUUCUUAAUGAUUGAACAAAA-3' (SEQ ID NO: 417) and the antisense strand comprises the nucleotide sequence 5'-UUUUGUUCAAUCAUUAAGAAGAC-3' (SEQ ID NO: 419).

In one embodiment, the sense strand comprises the nucleotide sequence 5'-csusucuuAfaUfGfAfuugaacaaaa-3' (SEQ ID NO: 33) and the antisense strand comprises the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA) S-Isomer.

In one aspect, the present invention provides a double stranded RNA (dsRNA) molecule that inhibits expression of a serine peptidase inhibitor, clade A, member 1 (Serpina1) gene, comprising a sense strand and an antisense strand forming a double stranded region, wherein the sense strand comprises the nucleotide sequence 5'-csusucuuAfaUfGfAfuugaacaaaaL96-3' (SEQ ID NO: 35) and the antisense strand comprises the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; (Tgn) is a thymidine-glycol nucleic acid (GNA) S-Isomer; and L96 is N-[tris(GalNAc-alkyl)-amidodecanoyl)]-4-hydroxyprolinol.

In one aspect the invention provides a dsRNA agent that inhibits expression of a serine peptidase inhibitor, clade a, member 1 (Serpina1) gene, comprising a sense strand and an antisense strand, each strand having 14 to 40 nucleotides, wherein the antisense strand has sufficient complementarity to a target Serpina1 sequence, e.g., nucleotides 1440-1480 of SEQ ID NO:1, to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature ($T_m$) of from about 40° C. to about 80° C.; (ii) the antisense comprises 2, 3, 4, 5 or 6 2'-fluoro modifications; (iii) the antisense comprises 1, 2, 3 or 4 phosphorothioate internucleotide linkages; (iv) the sense strand is conjugated with a ligand; (v) the sense strand comprises 2, 3, 4 or 5 2'-fluoro modifications; (vi) the sense strand comprises 1, 2, 3 or 4 phosphorothioate internucleotide linkages; (vii) the dsRNA comprises at least four 2'-fluoro modifications; (viii) the dsRNA comprises a duplex region of 12-40 nucleotide pairs in length; and (ix) a blunt end at 5'end of the antisense strand.

In some embodiments, the invention provides a a dsRNA agent that inhibits expression of a serine peptidase inhibitor, clade a, member 1 (Serpina1) gene, comprising a sense strand and an antisense strand, each strand having 14 to 40 nucleotides, wherein the antisense strand has sufficient complementarity to a target Serpina1 sequence, e.g., nucleotides 1440-1480 of SEQ ID NO:1, to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven, eight or all nine) of the following characteristics: (i) a melting temperature ($T_m$) of from about 40° C. to about 80° C.; (ii) the antisense comprises 6, 7, 8, 9, 10, 11 or 12 2'-OMe modifications; (iii) the antisense comprises 1, 2, 3 or 4 phosphorothioate internucleotide linkages; (iv) the sense strand is conjugated with a ligand; (v) the sense strand comprises 6, 7, 8, 9, 10, 11 or 12 2'-OMe modifications; (vi) the sense strand comprises 1, 2, 3 or 4 phosphorothioate internucleotide linkages; (vii) the dsRNA comprises at least 1, 2, 3, 4 or 5 2'-deoxy modification(s); (viii) the dsRNA comprises a duplex region of 12-40 nucleotide pairs in length; and (ix) a blunt end at 5' end of the antisense strand.

In some embodiments, the dsRNA has a melting temperature with a lower end of the range from about 40° C., 45° C., 50° C., 55° C., 60° C. or 65° C., and upper end of the arranger from about 70° C., 75° C. or 80° C. In some embodiments, the dsRNA has a melting temperature in the range from about 55° C. to about 70° C. In some embodiments, the dsRNA has a melting temperature in the range from about 57° C. to about 67° C. In some particular embodiments, the dsRNA has a melting temperature in the range from about 60° C. to about 67° C. In some additional embodiments, the dsRNA has a melting temperature in the range from about 62° C. to about 66° C.

It has also been discovered that dsRNA agents having a melting temperature of at least 60° C. are more effective in vivo and in vitro. Thus, in some embodiments, the dsRNA has a melting temperature of at least 60° C.

In some embodiments, the dsRNA agent comprises a sense strand and an antisense strand, each strand having 14 to 40 nucleotides, wherein the antisense strand has sufficient complementarity to a target Serpina1 sequence, e.g., nucleotides 1440-1480 of SEQ ID NO:1, to mediate RNA interference and wherein the antisense strand comprises at least one thermally destabilizing modification of the duplex within the seed region (i.e., at position 2-9 of the 5'-end of the antisense strand, counting from the 5'-end), the dsRNA has a melting temperature ($T_m$) of from about 40° C. to about 80° C., and the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) a blunt end at 5'end of the antisense strand.

In some embodiments, the dsRNA agent has a duplex region of 12-40 nucleotide pairs in length, wherein the antisense strand comprises at least one thermally destabilizing modification of the duplex within the seed region (i.e., at position 2-9 of the 5'-end of the antisense strand, counting from the 5'-end), and the dsRNA has a $T_m$ of from about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and vii) a blunt end at 5'end of the antisense strand.

In some embodiments, the dsRNA agent has a duplex region of 19, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C.

In some embodiments, the dsRNA agent has a duplex region of 19, 21, 22 or 23 nucleotide base pairs in length, wherein the antisense strand contains at least one thermally destabilizing modification of the duplex located in the seed region of the antisense strand (i.e., at position 2-9 of the 5'-end of the antisense strand), and wherein the dsRNA has a melting temperature of about 40° C. to about 80° C. (e.g., 40° C., 50° C., 60° C., 70° C. or 80° C.).

In some particular embodiments, the thermally destabilizing modification of the duplex is at position 5, 6, 7, or 8 of the antisense strand, counting from 5'-end of the antisense strand.

In some particular embodiments, the thermally destabilizing modification of the duplex is at position 6 of the antisense strand, counting from 5'-end of the antisense strand.

In some particular embodiments, the thermally destabilizing modification of the duplex is at position 7 of the antisense strand, counting from 5'-end of the antisense strand.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference and wherein the antisense strand comprises at least one thermally destabilizing modification of the duplex within the seed region (i.e., at position 2-9 of the 5'-end of the antisense strand, counting from the 5'-end), wherein the dsRNA has a melting temperature of about 40° C. to about 80° C., and the antisense strand further comprises one or both of the following characteristics:

(i) 2, 3, 4, 5 or 6 2'-fluoro modifications; and (ii) 1, 2, 3 or 4 phosphorothioate internucleotide linkages; and the sense strand comprises one, two or three of the following characteristics:

(i) a ligand conjugated with the sense strand;

(ii) 2, 3, 4 or 5 2'-fluoro modifications; and (iii) 1, 2, 3 or 4 phosphorothioate internucleotide linkages.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference and wherein the antisense strand comprises at least one thermally destabilizing modification of the duplex within the first 9 nucleotide positions counting from the 5'-end, and a ligand is conjugated with the sense strand, and wherein the dsRNA has a melting temperature of about 40° C. to about 80° C.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, said sense strand comprises a ligand, and wherein the dsRNA has a melting temperature of about 40° C. to about 80° C. In some further embodiments of this, the ligand is an ASGPR ligand.

In some embodiments, the dsRNA agent comprises a sense strand and an antisense strand, each strand having 14 to 40 nucleotides, wherein the antisense strand has sufficient complementarity to a Serina1 target sequence, e.g., nucleotides 1440-1480 of SEQ ID NO:1, to mediate RNA interference, wherein said antisense strand comprises at least one thermally destabilizing modification of the duplex located in position 4-8, counting from the 5'-end, wherein said sense strand comprises a ligand, wherein each of the sense and antisense strands comprise at least two 2'-fluoro modifications, and wherein the dsRNA has a melting temperature of about 40° C. to about 80° C. In some further embodiments of this, the ligand is an ASGPR ligand.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and antisense strand has a length of 18 to 35 nucleotides. In some further embodiments the ligand is an ASGPR ligand.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double stranded region.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the thermally destabilizing modification of the duplex is selected from the group consisting of:

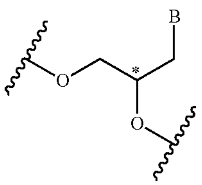,
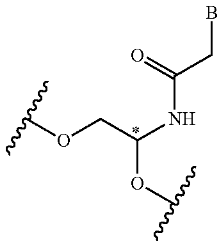,
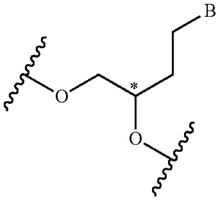,
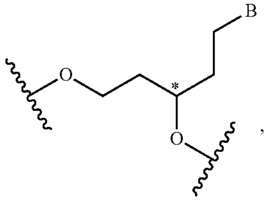,
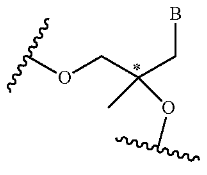, and
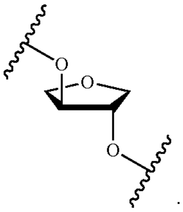.

wherein B is a modified or unmodified nucleobase and the asteric on each structure represents either R, S or racemic.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the thermally destabilizing modification of the duplex is selected from the group consisting of:

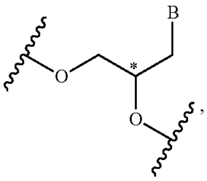,
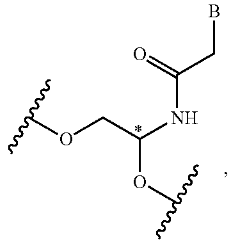,
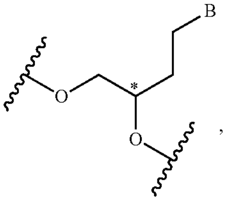,
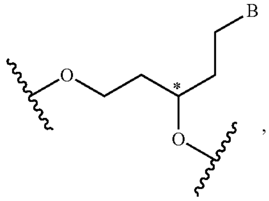,
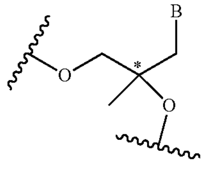, and
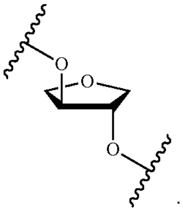.

wherein B is a modified or unmodified nucleobase and the asteric on each structure represents either R, S or racemic.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex located at position 7, counting from the 5'-end of the antisense strand, wherein said sense strand comprises a ligand, and wherein the dsRNA has a melting temperature of about 40° C. to about 80° C.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, wherein the dsRNA has a melting temperature of about 40° C. to about 80° C., and wherein the thermally destabilizing modification of the duplex is selected from the group consisting of:

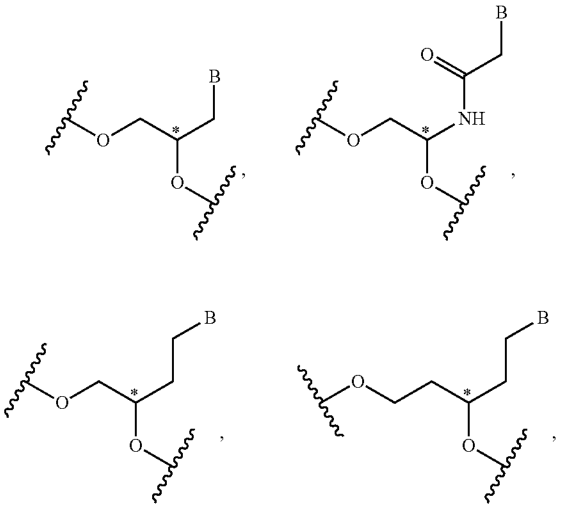

-continued

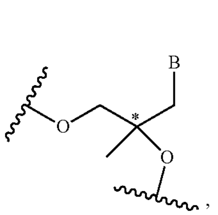

and

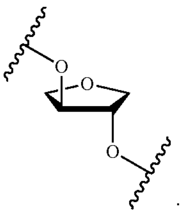

wherein B is a modified or unmodified nucleobase and the asteric on each structure represents either R, S or racemic.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, wherein said sense strand comprises a ligand, wherein the dsRNA has a melting temperature of about 40° C. to about 80° C., and wherein the ligand comprises one or more GalNAc derivatives attached through a bivalent or trivalent branched linker.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the dsRNA has a melting temperature of about 40° C. to about 80° C., and wherein the ligand is an ASGPR ligand of structure:

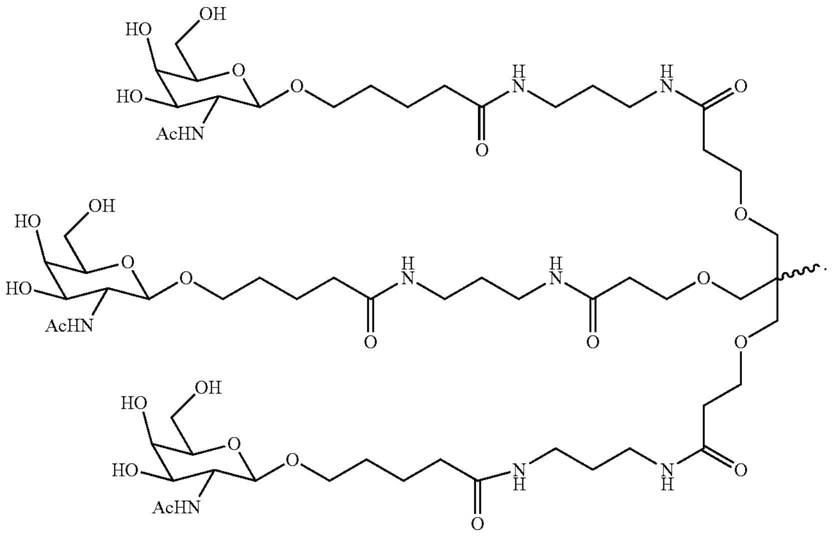 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1 or 2 phosphorothioate internucleotide linkages; wherein the antisense strand comprises 3, 4, 5 or 6 2'-fluoro modifications, comprises 2, 3 or 4 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3 or 4 phosphorothioate internucleotide linkages; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0 or 2 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0 or 2 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 18, 19, 21, 22, 23, 24 or 24 nucleotide pairs in length; and (viii) the dsRNA comprises a blunt end at 5'-end of the sense strand. In some particular embodiments, sense strand is 19, 20 or 21 or 22 nucleotides in length and the antisense strand is 20, 21 or 22 nucleotides in length.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; wherein the dsRNA has a melting temperature of about 40° C. to about 80° C.; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) and the dsRNA comprises a duplex region of 12-40 nucleotide pairs in length. In some embodiments, the overhang is on the 3'-end of the antisense strand and the blunt end is at the 5'-end of the antisense strand. In some particular embodiments, the overhang is 2, 3 or 4-nucleotides in length.

In some embodiments, the dsRNA agent has a duplex region of 19, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand.

In some embodiments, the dsRNA agent of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and (vii) the dsRNA comprises a duplex region of 12-40 nucleotide pairs in length.

In some embodiments, the dsRNA agent has a duplex region of 19, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications.

In some embodiments, the dsRNA agent of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA agent of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce Serpina1 target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), and wherein the dsRNA has a melting temperature of about 40° C. to about 80° C. For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA agent of the invention comprises a sense and antisense strands, wherein said dsRNA agent comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a Serina1 target mRNA along at least 19 nt of said antisense strand length to reduce target gene expression when said dsRNA agent is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications; and (vii) the dsRNA has a duplex region of 12-29 nucleotide pairs in length.

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3 or 4 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), wherein the dsRNA has a melting temperature of about 40° C. to about 80° C., and wherein the dsRNA optionally further has at least one (e.g., one, two, three, four, five, six or all seven) of the following characteristics: (i) the antisense comprises 2, 3, 4, 5 or 6

2'-fluoro modifications; (ii) the sense strand is conjugated with a ligand; (iii) the sense strand comprises 2, 3, 4 or 5 2'-fluoro modifications; (iv) the sense strand comprises 3 or 4 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In one aspect the invention provides a dsRNA agent capable of inhibiting the expression of a Serpina1 target sequence, e.g., nucleotides 1440-1480 of SEQ ID NO:1, comprising a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference and wherein the antisense strand comprises at least one thermally destabilizing modification of the duplex within the seed region (i.e., at position 2-9 of the 5'-end of the antisense strand, counting from the 5'-end), and the dsRNA further has at least one (e.g., one, two, three, four, five, six seven or all eight) of the following characteristics:

(i) the antisense comprises 2, 3, 4, 5 or 6 2'-fluoro modifications;
(ii) the antisense comprises 1, 2, 3 or 4 phosphorothioate internucleotide linkages;
(iii) the sense strand is conjugated with a ligand;
(iv) the sense strand comprises 2, 3, 4 or 5 2'-fluoro modifications;
(v) the sense strand comprises 1, 2, 3 or 4 phosphorothioate internucleotide linkages;
(vi) the dsRNA comprises at least four 2'-fluoro modifications;
(vii) the dsRNA comprises a duplex region of 12-40 nucleotide pairs in length; and
(viii) a blunt end at 5'end of the antisense strand.

In some particular embodiments, the thermally destabilizing modification of the duplex is at position 7 of the antisense strand, counting from 5'-end of the antisense strand.

In some embodiments, the dsRNA agent comprises a sense strand and an antisense strand, each strand having 14 to 40 nucleotides, wherein the antisense strand has sufficient complementarity to the target sequence to mediate RNA interference and wherein the antisense strand comprises at least one thermally destabilizing modification of the duplex within the seed region (i.e., at position 2-9 of the 5'-end of the antisense strand, counting from the 5'-end), and the antisense strand further comprises one or both of the following characteristics:

(iii) 2, 3, 4, 5 or 6 2'-fluoro modifications; and
(iv) 1, 2, 3 or 4 phosphorothioate internucleotide linkages; and the sense strand comprises one, two or three of the following characteristics:

(iv) a ligand conjugated with the sense strand;
(v) 2, 3, 4 or 5 2'-fluoro modifications; and
(vi) 1, 2, 3 or 4 phosphorothioate internucleotide linkages.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference and wherein the antisense strand comprises at least one thermally destabilizing modification of the duplex within the first 9 nucleotide positions counting from the 5'-end, and a ligand is conjugated with the sense strand.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference and wherein the antisense strand comprises at least one thermally destabilizing modification of the duplex within the first 9 nucleotide positions counting from the 5'-end, a ligand is conjugated with the sense strand, and the dsRNA comprises at least four 2'-fluoro modifications.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand. In some further embodiments of this, the ligand is an ASGPR ligand.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications. In some further embodiments of this, the ligand is an ASGPR ligand.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the antisense further comprises at least two of the following characteristics: (i) the thermally destabilizing modification of the duplex is located in position 4 to 8 of the antisense strand; (ii) at least two 2'-fluoro modifications; (iii) phosphorothioate internucleotide linkages between nucleotide positions 1 and 2 (counting from the 5' end); and antisense strand has a length of 18 to 35 nucleotides. In some further embodiments the ligand is an ASGPR ligand.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and the sense strand has at least one of the following characteristics: (i) the ligand is attached to either end of the sense strand; (ii) sense strand comprises at least two 2'-fluoro modifications; and (iii) the sense strand and the antisense strand show sufficient complementarity to form a double stranded region spanning at least 19 nucleotide positions and wherein the thermally destabilizing modification of the duplex is located within said double stranded region.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, and wherein the thermally destabilizing modification of the duplex is selected from the group consisting of:

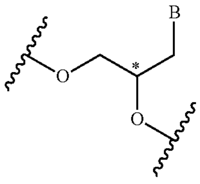,
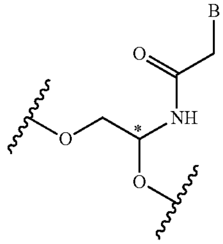,
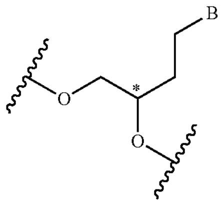,
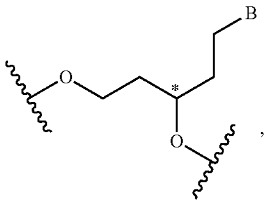,
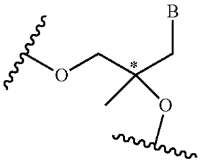, and
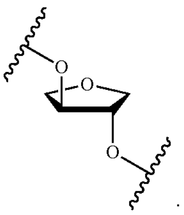.

wherein B is a modified or unmodified nucleobase and the asteric on each structure represents either R, S or racemic.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein said antisense strand comprises at least one thermally destabilizing modification of the duplex located in position 4-8, counting from the 5'-end, wherein said sense strand comprises a ligand, and wherein each of the sense and antisense strands comprise at least two 2'-fluoro modifications, and wherein the thermally destabilizing modification of the duplex is selected from the group consisting of:

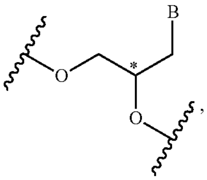,
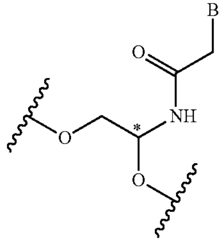,
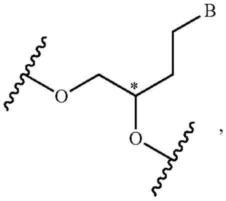,
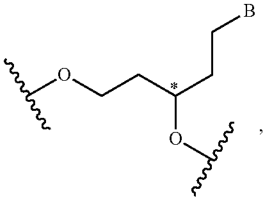,
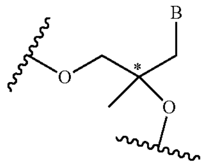, and
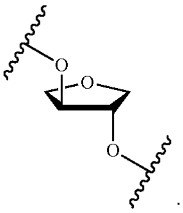.

wherein B is a modified or unmodified nucleobase and the asteric on each structure represents either R, S or racemic.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex located at position 7, counting from the 5'-end of the antisense strand, and wherein said sense strand comprises a ligand.

In some embodiments, the dsRNA agent comprises a sense strand and an antisense strand, each strand having 14 to 40 nucleotides, wherein the antisense strand has sufficient complementarity to the Serpina1 target sequence, e.g., nucleotides 1440-1480 of SEQ ID NO:1, to mediate RNA interference, wherein said antisense strand comprises at least one thermally destabilizing modification of the duplex located at position 7, counting from the 5'-end, wherein said sense strand comprises a ligand, and wherein each of the sense and antisense strands comprise at least two 2'-fluoro modifications, and wherein the thermally destabilizing modification of the duplex is selected from the group consisting of:

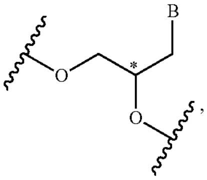,
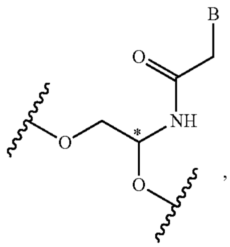,

-continued

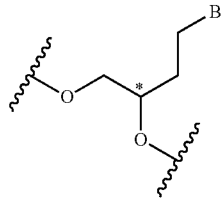 , 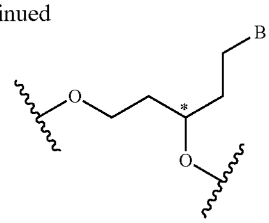 ,

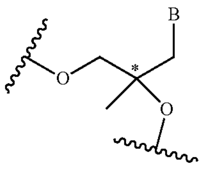 , and 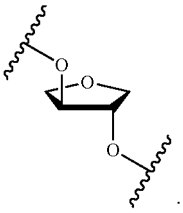 .

wherein B is a modified or unmodified nucleobase and the asteric on each structure represents either R, S or racemic.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the ligand comprises one or more GalNAc derivatives attached through a bivalent or trivalent branched linker.

In some embodiments, the dsRNA agent comprises a sense strand and an antisense strand, each strand having 14 to 40 nucleotides, wherein the antisense strand has sufficient complementarity to a Serpina1 target sequence, e.g., nucleotides 1440-1480 of SEQ ID NO:1, to mediate RNA interference, wherein the dsRNA comprises at least four 2'-fluoro, wherein said antisense strand comprises at least one thermally destabilizing modification of the duplex within the first 9 nucleotide positions, counting from the 5'-end, and wherein said sense strand comprises a ligand, wherein the ligand is an ASGPR ligand of structure:

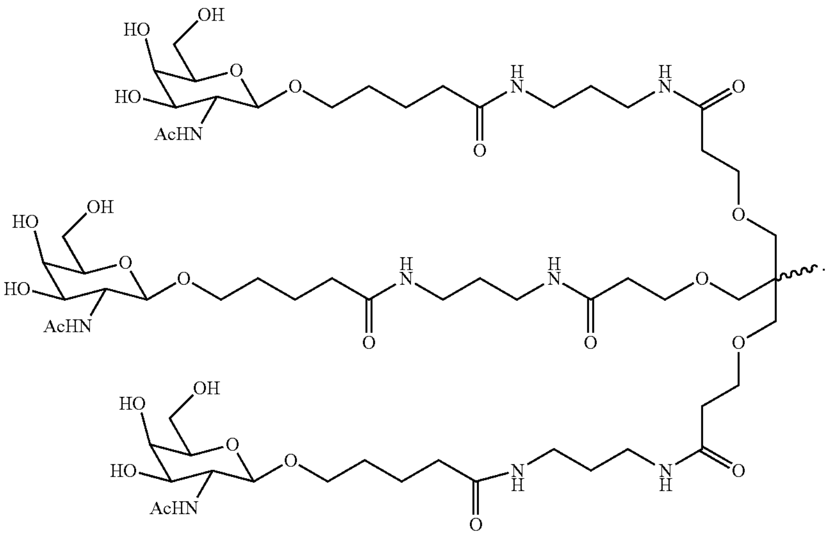 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0, 1 or 2 phosphorothioate internucleotide linkages; wherein the antisense strand comprises 3, 4, 5 or 6 2'-fluoro modifications, comprises 2, 3 or 4 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 3, 4, 5 or 6 2'-fluoro modifications, comprises 2, 3 or 4 phosphorothioate internucleotide linkages; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0 or 2 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 3 or 4 2'-fluoro modifications, and comprises 0 or 2 phosphorothioate internucleotide linkages; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, and between nucleotide positions 22 and 23; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In some embodiments, the sense and antisense strands are independently 19, 20, 21, 22, 23, 24 or 25 nucleotides in length; the antisense strand contains at least one thermally destabilizing nucleotide, where the at least one thermally destabilizing nucleotide is in the seed region of the antisense strand (i.e., at position 2-9 of the 5'-end of the antisense strand); wherein the sense strand is conjugated with a ligand, comprises 2'-fluoro modifications at positions 7, 10 and 11 or at positions 7, 9, 10 and 11 (counting from 5'-end of the sense strand), and optionally comprises phosphorothioate internucleotide linkages between nucleotide positions 1 and 2, and between nucleotide positions 2 and 3; wherein the antisense strand comprises 2'-fluoro modifications at positions 2, 6, 8, 9, 14 or 16, or at positions 2, 6, 14 or 16, or at positions 2, 14 and 16; and the antisense comprises phosphorothioate internucleotide linkages between nucleotide positions 21 and 22, between nucleotide positions 22 and 23, between nucleotide positions 1 and 2, between nucleotide positions 2 and 3; and wherein the dsRNA optionally further has at least one (e.g., one, two or all three) of the following characteristics: (i) the dsRNA comprises a duplex region of 12-25 nucleotide pairs in length; (ii) the dsRNA comprises a blunt end at 5'-end of the antisense strand; and (iii) the dsRNA has at least a two nucleotide overhang at the 3'-end of the antisense strand.

In a particular embodiment, the dsRNA agents of the present invention comprise:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker; and
  (iii) 2'-F modifications at positions 7, 10, and 11 (counting from the 5' end); and
(b) an antisense strand having:
  (i) a length of 23 nucleotides;
  (ii) 2'-F modifications at positions 2, 6 to 8, 9, 14, and 16 (counting from the 5' end);
  (iii) phosphorothioate internucleotide linkages between nucleotide positions 21 and 22, and between nucleotide positions 22 and 23 (counting from the 5' end); and
  (iv) a thermally destabilizing modification of the duplex at position 7 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);
  and
(b) an antisense strand having:
  (i) a length of 23 nucleotides;
  (ii) 2'-F modifications at positions 2, 6, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);

and (b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 6 or 7 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);

and (b) an antisense strand having:
  (i) a length of 23 nucleotides;
  (ii) 2'-F modifications at positions 2, 6, 8, 9, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprise:

(a) a sense strand having:
  (i) a length of 21 nucleotides;
  (ii) an ASGPR ligand attached to the 3'-end, wherein said ASGPR ligand comprises three GalNAc derivatives attached through a trivalent branched linker;
  (iii) 2'-F modifications at positions 7, 9, 10, and 11 (counting from the 5' end); and
  (iv) phosphorothioate internucleotide linkages between nucleotide positions 1 and 2, and between nucleotide positions 2 and 3 (counting from the 5' end);

and (b) an antisense strand having:
  (i) a length of 23 nucleotides;
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 7 (counting from the 5' end);

wherein the dsRNA agents have a two nucleotide overhang at the 3'-end of the antisense strand, and a blunt end at the 5'-end of the antisense strand.

In another particular embodiment, the dsRNA agents of the present invention comprising an antisense strand having:
  (i) 2'-F modifications at positions 2, 14, and 16 (counting from the 5' end); and
  (2) a thermally destabilizing modification of the duplex at position 6 or 7 (counting from the 5' end).

In another particular embodiment, the dsRNA agents of the present invention comprise:

(a) a sense strand having:
  (i) an ASGPR ligand, wherein said ASGPR ligand;
  (ii) phosphorothioate internucleotide linkages between nucleotide positions 1 and 2, and between nucleotide positions 2 and 3 (counting from the 5' end);

and (b) an antisense strand having:
  (i) 2'-F modifications at positions 2, 14, and 16 (counting from the 5' end);
  (ii) a thermally destabilizing modification of the duplex at position 6 or 7 (counting from the 5' end); In another particular embodiment, the dsRNA agents of the present invention comprise:

(a) a sense strand having:
  (i) an ASGPR ligand attached to the 3'-end, wherein said ASGPR ligand comprises three GalNAc derivatives attached through a trivalent branched linker;
  (ii) phosphorothioate internucleotide linkages between nucleotide positions 1 and 2, and between nucleotide positions 2 and 3 (counting from the 5' end);

and (b) an antisense strand having:
  (ii) 2'-F modifications at positions 2, 14, and 16 (counting from the 5' end);
  (iii) phosphorothioate internucleotide linkages between nucleotide positions 1 and 2, between nucleotide positions 2 and 3, between nucleotide positions 21 and 22, and between nucleotide positions 22 and 23 (counting from the 5' end); and
  (iv) a thermally destabilizing modification of the duplex at position 6 or 7 (counting from the 5' end);

wherein the dsRNA agents have a two nucleotide overhang at the 3'-end of the antisense strand, and a blunt end at the 5'-end of the antisense strand.

In some embodiments, the dsRNA agent further comprises at least one ASGPR ligand. For example, the ASGPR ligand is one or more GalNAc derivatives attached through a bivalent or trivalent branched linker, such as:

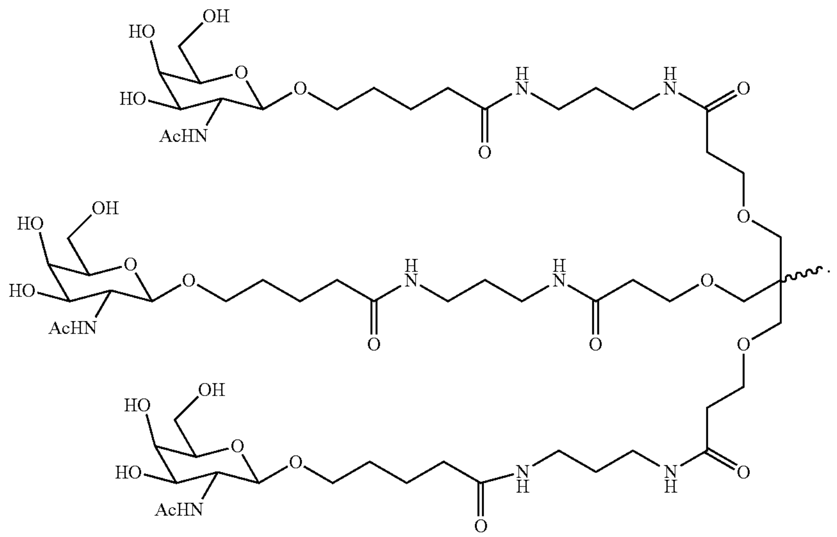 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In one example, the ASGPR ligand is attached to the 3' end of the sense strand.

The region of a Serpina1 mRNA targeted by any of the dsRNA agents described herein may be nucleotides 1440-1480 of SEQ ID NO:1; or nucleotides 1441-1479 of SEQ ID NO:1; or nucleotides 1442-1478 of SEQ ID NO:1; or nucleotides 1443-1477 of SEQ ID NO:1; or nucleotides 1444-1476 of SEQ ID NO:1; or nucleotides 1445-1475 of SEQ ID NO:1; or nucleotides 1446-1474 of SEQ ID NO:1; or nucleotides 1447-1473 of SEQ ID NO:1; or nucleotides 1448-1473 of SEQ ID NO:1; or nucleotides 1448-1472 of SEQ ID NO:1; or nucleotides 1448-1471 of SEQ ID NO:1; or nucleotides 1448-1470 of SEQ ID NO:1; or nucleotides 1447-1469 of SEQ ID NO:1; or nucleotides 1446-1478 of SEQ ID NO:1; or nucleotides 1449-1471 of SEQ ID NO:1; or nucleotides 1450-1472 of SEQ ID NO:1; or nucleotides 1440-1475 of SEQ ID NO:1; or nucleotides 1445-1480 of SEQ ID NO:1; or nucleotides 1445-1475 of SEQ ID NO:1.

The present invention also provides vectors, cells, and pharmaceutical compositions comprising the dsRNA agents of the invention.

The pharmaceutical compositions of the invention may be an unbuffered solution, e.g., saline or water; or a buffered solution, e.g., a buffered solution comprising acetate, citrate, prolamine, carbonate, or phosphate or any combination thereof, or phosphate buffered saline (PBS).

In one aspect, the present invention provides a method of inhibiting Serpina1 expression in a cell. The method includes contacting the cell with any of the foregoing dsRNA agents or pharmaceutical composition of the invention, thereby inhibiting expression of the Serpina1 gene in the cell.

In one embodiment, the cell is in a subject, such as a human subject.

In one embodiment, the Serpina1 expression is inhibited by at least about 30%, about 40%, about 50%, about 60%, about 70%, about 80%, about 90%, about 95%, about 98%, or about 100%.

In one aspect, the present invention provides a method of treating a subject having a Serpina1 associated disease. The method includes administering to the subject a therapeutically effective amount of any of the foregoing dsRNA agents or pharmaceutical composition of the invention, thereby treating said subject.

In one embodiment, the subject is a human.

In one embodiment, the Serpina1 associated disease is a liver disorder.

In one embodiment, the liver disorder is selected from the group consisting of chronic liver disease, liver inflammation, cirrhosis, liver fibrosis, and/or hepatocellular carcinoma.

In another aspect, the present invention provides a method of inhibiting development of hepatocellular carcinoma in a subject having a Serpina1 deficiency variant. The method includes administering to the subject a therapeutically effective amount of any of the foregoing dsRNA agents or pharmaceutical composition of the invention, thereby inhibiting development of hepatocellular carcinoma in the subject.

In yet another aspect, the present invention provides a method of reducing the accumulation of misfolded Serpina1 in the liver of a subject having a Serpina1 deficiency variant. The method includes administering to the subject a therapeutically effective amount of any of the foregoing dsRNA agents or pharmaceutical composition of the invention, thereby reducing the accumulation of misfolded Serpina1 in the liver of the subject.

The dsRNA agent may administered to the subject at a dose of about 0.01 mg/kg to about 10 mg/kg or about 0.5 mg/kg to about 50 mg/kg; or a dose of about 10 mg/kg to about 30 mg/kg.

The dsRNA agent may administered to the subject subcutaneously; or intravenously.

The dsRNA agent may administered to the subject in two or more doses.

The present invention is further illustrated by the following detailed description and drawings.

BRIEF DESCRIPTION OF THE DRAWINGS

FIG. 1A discloses SEQ ID NOs: 36-37, 36, 38, 36 and 39, respectively, in order of appearance.

FIG. 1C discloses SEQ ID NOs: 36-37, 36-37, 36 and 39, respectively, in order of appearance.

DETAILED DESCRIPTION OF THE INVENTION

Figures 1A, 1B, 1C, 1D:
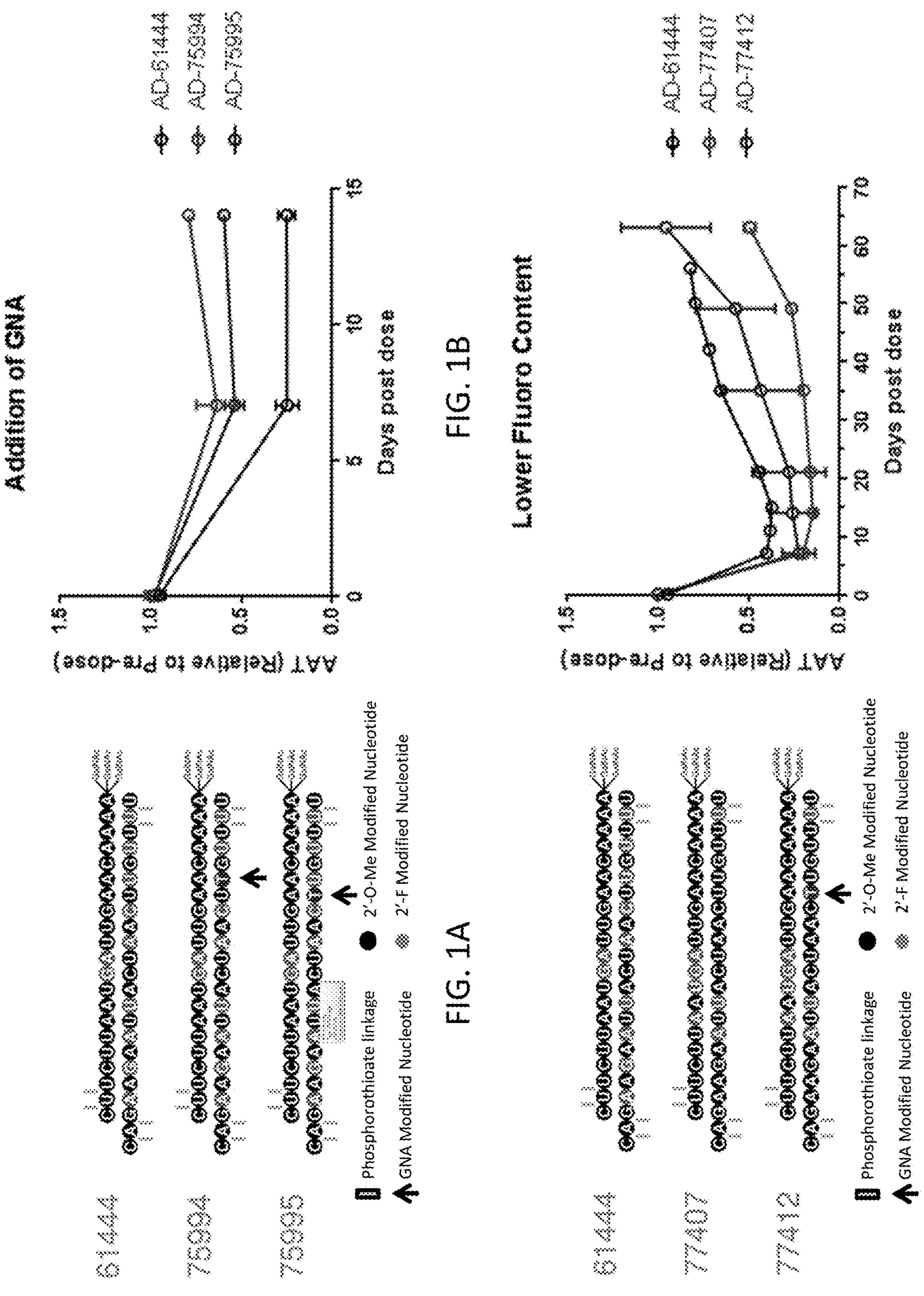
FIG. 1A schematically depicts the modified sense and antisense strand nucleotide sequences of AD-61444; AD-75994; and AD-75995.
FIG. 1B is a graph depicting the in vivo effect of administration of the indicated dsRNA agents on the level of expression of AAT (Serpina). The level of expression of AAT shown is relative to the pre-bleed level of expression of AAT.
FIG. 1C schematically depicts the modified sense and antisenes strand nucleotide sequences of AD-61444; AD-77404; and AD-77412.
FIG. 1D is a graph depicting the in vivo effect of administration of the indicated dsRNA agents on the level of expression of AAT (Serpina).

The present invention provides compositions comprising agents, e.g., RNAi agents, e.g., double stranded iRNA agents, targeting Serpina1. Also disclosed are methods using the compositions of the invention for inhibiting Serpina1 expression and for treating Serpina1 associated diseases, such as liver disorders, e.g., chronic liver disease, liver inflammation, cirrhosis, liver fibrosis, and/or hepatocellular carcinoma.

The present invention is based, at least in part on the discovery of effective nucleotide or chemical motifs for dsRNA agents targeting Serpina1 which are advantageous for inhibition of target gene expression, while having reduced off-target gene silencing effects, as well as compositions comprising such agents suitable for therapeutic use. More specifically, it has been discovered inter alia that dsRNA agents targeting Serpina1 where the antisense strand comprises at least one thermally destabilizing modification of the duplex within the seed region (i.e., at position 2-9 of the 5'-end of the antisense strand, counting from the 5'-end) and/or the dsRNA agent has a melting temperature in the range of from about 40° C. to about 80° C. can be more effective in mediating RNA interference than a parent dsRNA agent lacking the destabilizing modification.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "Serpina1" refers to the serpin peptidase inhibitor, clade A, member 1 gene or protein. Serpina1 is also known as alpha-1-antitrypsin, α-1-antitrypsin, AAT, protease inhibitor 1, PI, PI1, anti-elastase, and antitrypsin.

The term Serpina1 includes human Serpina1, the amino acid and nucleotide sequence of which may be found in, for example, GenBank Accession Nos. GI:189163524 (SEQ ID NO:1), GI:189163525 (SEQ ID NO:2), GI:189163526 (SEQ ID NO:3), GI:189163527 (SEQ ID NO:4), GI:189163529 (SEQ ID NO:5), GI:189163531 (SEQ ID NO:6), GI:189163533 (SEQ ID NO:7), GI:189163535 (SEQ ID NO:8), GI:189163537 (SEQ ID NO:9), GI:189163539 (SEQ ID NO:10), and/or GI:189163541 (SEQ ID NO:11); rhesus Serpina1, the amino acid and nucleotide sequence of which may be found in, for example, GenBank Accession Nos. GI:402766667 (SEQ ID NO:12), GI:297298519 (SEQ ID NO:13), and/or GI: 297298520 (SEQ ID NO:14); mouse Serpina1, the amino acid and nucleotide sequence of which may be found in, for example, GenBank Accession No. GI:357588423 and/or GI:357588426; and rat, the amino acid and nucleotide sequence of which may be found in, for example, GenBank Accession No. GI:77020249. Additional examples of Serpina1 mRNA sequences are readily available using, e.g., GenBank and OMIM.

Over 120 alleles of Serpina1 have been identified and the "M" alleles are considered the wild-type or "normal" allele (e.g., "PIM1-ALA213" (also known as PI, M1A), "PIM1-VAL213" (also known as PI, MIV), "PIM2", "PIM3", and PIM4"). Additional variants may be found in, for example, the A(1)ATVar database (see, e.g., Zaimidou, S., et al. (2009) *Hum Mutat.* 230(3):308-13 and www.goldenhelix-.org/A1ATVar).

As used herein, the term "Serpina1 deficiency allele" refers to a variant allele that produces proteins which do not fold properly and may aggregate intracellularly and are, thus, not properly transported from the site of synthesis in the liver to the site of action within the body.

Exemplary Serpina1 deficiency alleles include, the "Z allele", the "S allele", the "PIM(Malton) allele", and the "PIM(Procida) allele".

As used herein, the terms "Z allele", "PIZ" and "Z-AAT" refer to a variant allele of Serpina1 in which the amino acid at position 342 of the protein is changed from a glutamine to a lysine as a result of the relevant codon being changed from GAG to AAG. A subject homozygous for a Z allele can be referred to as "PIZZ." Z-AAT mutations account for 95% of Serpina1 deficiency patients and are estimated to be present in 100,000 Americans and about 3 million individuals worldwide. The Z allele reaches polymorphic frequencies in Caucasians and is rare or absent in Asians and blacks. The homozygous ZZ phenotype is associated with a high risk of both emphysema and liver disease. Z-AAT protein does not fold correctly in the endoplasmic reticulum, leading to loop-sheet polymers which aggregate and reduce secretion, elicitation of the unfolded protein response, apoptosis, endoplasmic reticulum overload response, autophagy, mitochondrial stress, and altered hepatocyte function.

As used herein, the terms "PIM(Malton)" and "M(Malton)-AAT" refer to a variant allele of Serpina1 in which one of the adjacent phenylalanine residues at position 51 or 52 of the mature protein is deleted. Deletion of this one amino acid shortens one strand of the beta-sheet, B6, preventing normal processing and secretion in the liver which is associated with hepatocyte inclusions and impaired secretion of the protein from the liver.

As used herein, the term "PIS" refers to a variant allele of Serpina1 in which a glutamic acid at position 264 is substituted with valine. Although the majority of this variant protein is degraded intracellularly, there is a high frequency of the PIS allele in the Caucasian population and, thus, compound heterozygotes with a Z or null allele are frequent.

As used herein, "target sequence" refers to a contiguous portion of the nucleotide sequence of an mRNA molecule formed during the transcription of a Serpina1 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine, 2'-deoxythymidine or thymidine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

"Polynucleotides," also referred to as "oligonucleotides," are formed through the covalent linkage of adjacent nucleosides to one another, to form a linear polymeric oligonucleotide. Within the polynucleotide structure, the phosphate groups are commonly referred to as forming the internucleoside linkages of the polynucleotide. Polynucleotides may be either RNA or DNA and are, for example less than about 100, 200, 300, or about 400 nucleotides in length.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of Serpina1 in a cell, e.g., a cell within a subject, such as a mammalian subject.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

In one embodiment, an RNAi agent of the invention includes a single stranded RNA that interacts with a target RNA sequence, e.g., a Serpina1 target mRNA sequence, to direct the cleavage of the target RNA. Without wishing to be bound by theory it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (sssiRNA) generated within a cell and which promotes the formation of a RISC complex to effect silencing of the target gene, i.e., a Serpina1 gene. Accordingly, the term "siRNA" is also used herein to refer to an RNAi as described above.

In another embodiment, the RNAi agent may be a single-stranded RNAi agent that is introduced into a cell or organism to inhibit a target mRNA. Single-stranded RNAi agents (ssRNAi) bind to the RISC endonuclease, Argonaute 2, which then cleaves the target mRNA. The single-stranded siRNAs are generally 15-30 nucleotides and are chemically modified. The design and testing of single-stranded RNAi agents are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150; 883-894.

In another embodiment, an "iRNA" for use in the compositions and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an Serpina1 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA agent are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In one embodiment, an RNAi agent of the invention is a dsRNA, each strand of which comprises 19-23 nucleotides, that interacts with a target RNA sequence, e.g., a Serpina1 target mRNA sequence, to direct the cleavage of the target RNA. Without wishing to be bound by theory, long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In another embodiment, one or more of the nucleotides in the overhang is replaced with a nucleoside thiophosphate.

In certain embodiments, the overhang on the sense strand or the antisense strand, or both, can include extended lengths longer than 10 nucleotides, e.g., 10-30 nucleotides, 10-25 nucleotides, 10-20 nucleotides or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the extended overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence, e.g., a Serpina1 mRNA.

As used herein, the term "region of complementarity" refers to the region on the antisense strand that is substantially complementary to a sequence, for example a target sequence, e.g., a Serpina1 nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand" or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. For example, a complementary sequence is sufficient to allow the relevant function of the nucleic acid to proceed, e.g., RNAi. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Serpina1) including a 5' UTR, an open reading frame (ORF), or a 3' UTR. For example, a polynucleotide is complementary to at least a part of a Serpina1 mRNA if the sequence is substantially complementary to a non-interrupted portion of an mRNA encoding Serpina1.

In some embodiments, a dsRNA agent of the invention is "sufficiently complementary" to a Serpina1 target RNA, e.g., a target mRNA, such that the dsRNA agent silences production of protein encoded by the target mRNA. In another embodiment, the dsRNA agent of the invention is "exactly complementary" or fully complementary to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA agent of the invention specifically discriminates a single-nucleotide difference. In this case, the dsRNA agent only mediates RNAi if exact complementary is found in the region (e.g., within 7 nucleotides of) the single-nucleotide difference.

The term 'BNA' refers to bridged nucleic acid, and is often referred as constrained or inaccessible RNA. BNA can contain a 5-, 6-membered, or even a 7-membered bridged structure with a "fixed" $C_3$'-endo sugar puckering. The bridge is typically incorporated at the 2'-, 4'-position of the ribose to afford a 2',4'-BNA nucleotide (e.g., LNA, or ENA). Examples of BNA nucleotides include the following nucleosides:

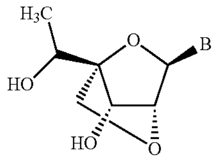

5' Me BNA

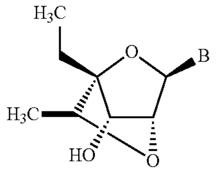

cEt BNA

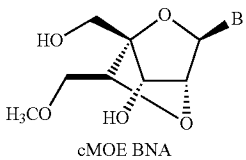

cMOE BNA

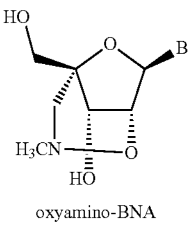

oxyamino-BNA

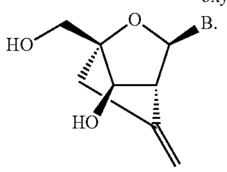

vinyl-carbo-BNA

The term 'LNA' refers to locked nucleic acid, and is often referred as constrained or inaccessible RNA. LNA is a modified RNA nucleotide. The ribose moiety of an LNA nucleotide is modified with an extra bridge (e.g., a methylene bridge or an ethylene bridge) connecting the 2' hydroxyl to the 4' carbon of the same ribose sugar. For instance, the bridge can "lock" the ribose in the 3'-endo North) conformation:

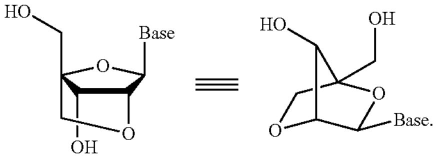

The term 'ENA' refers to ethylene-bridged nucleic acid, and is often referred as constrained or inaccessible RNA.

The term "inhibiting," as used herein, is used interchangeably with "reducing," "silencing," "downregulating," "suppressing" and other similar terms, and includes any level of inhibition.

The phrase "inhibiting expression of a Serpina1," as used herein, includes inhibition of expression of any Serpina1 gene (such as, e.g., a mouse Serpina1 gene, a rat Serpina1 gene, a monkey Serpina1 gene, or a human Serpina1 gene) as well as variants, (e.g., naturally occurring variants), or mutants of a Serpina1 gene. Thus, the Serpina1 gene may be a wild-type Serpina1 gene, a variant Serpina1 gene, a mutant Serpina1 gene, or a transgenic Serpina1 gene in the context of a genetically manipulated cell, group of cells, or organism.

"Inhibiting expression of a Serpina1 gene" includes any level of inhibition of a Serpina1 gene, e.g., at least partial suppression of the expression of a Serpina1 gene, such as an inhibition of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a Serpina1 gene may be assessed based on the level of any variable associated with Serpina1 gene expression, e.g., Serpina1 mRNA level, Serpina1 protein level, or serum AAT levels. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The phrase "contacting a cell with a double stranded RNAi agent," as used herein, includes contacting a cell by any possible means. Contacting a cell with a double stranded RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, the bloodstream or the subcutaneous space, such that the agent will subsequently reach the tissue where the cell to be contacted is located. For example, the RNAi agent may contain and/or be coupled to a ligand, e.g., a GalNAc3 ligand, that directs the RNAi agent to a site of interest, e.g., the liver. Combinations of in vitro and in vivo methods of contacting are also possible. In connection with the methods of the invention, a cell might also be contacted in vitro with an RNAi agent and subsequently transplanted into a subject.

A "patient" or "subject," as used herein, is intended to include either a human or non-human animal, preferably a mammal, e.g., a monkey. Most preferably, the subject or patient is a human.

A "Serpina1 associated disease," as used herein, is intended to include any disease, disorder, or condition associated with the Serpina1 gene or protein. Such a disease may be caused, for example, by misfolding of a Serpina1 protein, intracellular accumulation of Serpina1 protein (e.g., misfolded Serpina1 protein), excess production of the Serpina1 protein, by Serpina1 gene variants, Serpina1 gene mutations, by abnormal cleavage of the Serpina1 protein, by abnormal interactions between Serpina1 and other proteins or other endogenous or exogenous substances. A Serpina1 associated disease may be a liver disease and/or a lung disease.

A "liver disease", as used herein, includes a disease, disorder, or condition affecting the liver and/or its function. A liver disorder can be the result of accumulation of Serpina1 protein in the liver and/or liver cells. Examples of liver disorders include liver disorders resulting from, viral infections, parasitic infections, genetic predisposition, autoimmune diseases, exposure to radiation, exposure to hepatotoxic compounds, mechanical injuries, various environmental toxins, alcohol, acetaminophen, a combination of alcohol and acetaminophen, inhalation anesthetics, niacin, chemotherapeutics, antibiotics, analgesics, antiemetics and the herbal supplement kava, and combinations thereof.

For example, a liver disorder associated with Serpina1 deficiency may occur more often in subjects with one or more copies of certain alleles (e.g., the PIZ, PiM(Malton), and/or PIS alleles). Without wishing to be bound by theory, it is thought that alleles associated with a greater risk of developing an alpha-1 anti-tryp sin liver disease encode forms of Serpina1 which are subject to misfolding and are not properly secreted from the hepatocytes. The cellular responses to these misfolded proteins can include the unfolded protein response (UPR), endoplasmic reticulum-associated degradation (ERAD), apoptosis, ER overload response, autophagy, mitochondrial stress and altered hepatocyte function. The injuries to the hepatocytes can lead to symptoms such as, but not limited to, inflammation, cholestasis, fibrosis, cirrhosis, prolonged obstructive jaundice, increased transaminases, portal hypertension and/or hepatocellular carcinoma. Without wishing to be bound by theory, the highly variable clinical course of this disease is suggestive of modifiers or "second hits" as contributors to developing symptoms or progressing in severity.

For example, subjects with a PIZ allele can be more sensitive to Hepatitis C infections or alcohol abuse and more likely to develop a liver disorder if exposed to such factors. Additionally cystic fibrosis (CF) subjects carrying the PIZ allele are at greater risk of developing severe liver disease with portal hypertension. A deficiency of Serpina1 can also cause or contribute to the development of early onset emphysema, necrotizing panniculitis, bronchiectasis, and/or prolonged neonatal jaundice. Some patients having or at risk of having a deficiency of alpha-1-antitrypsin are identified by screening when they have family members affected by an alpha-1-antitrypsin deficiency.

Exemplary liver disorders include, but are not limited to, liver inflammation, chronic liver disease, cirrhosis, liver fibrosis, hepatocellular carcinoma, liver necrosis, steatosis, cholestatis and/or reduction and/or loss of hepatocyte function.

"Cirrhosis" is a pathological condition associated with chronic liver damage that includes extensive fibrosis and regenerative nodules in the liver.

"Fibrosis" is the proliferation of fibroblasts and the formation of scar tissue in the liver.

The phrase "liver function" refers to one or more of the many physiological functions performed by the liver. Such functions include, but are not limited to, regulating blood sugar levels, endocrine regulation, enzyme systems, interconversion of metabolites (e.g., ketone bodies, sterols and steroids and amino acids); manufacturing blood proteins such as fibrinogen, serum albumin, and cholinesterase, erythropoietic function, detoxification, bile formation, and vitamin storage. Several tests to examine liver function are known in the art, including, for example, measuring alanine amino transferase (ALT), alkaline phosphatase, bilirubin, prothrombin, and albumin.

"Therapeutically effective amount," as used herein, is intended to include the amount of an RNAi agent that, when administered to a patient for treating a Serpina1-associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by Serpina1 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of an Serpina1-associated disease, but who may be predisposed to the disease, is sufficient to prevent or ameliorate the disease or one or more symptoms of the disease. Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylacticaly effective amount" also includes an amount of an RNAi agent that produces some desired local or systemic effect at a reasonable benefit/risk ratio applicable to any treatment. RNAi gents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, urine, lymph, cerebrospinal fluid, ocular fluids, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue (or subcomponents thereof) derived from the subject.

II. iRNAs of the Invention

Described herein are improved double stranded RNAi agents which inhibit the expression of a Serpina1 gene in a cell, such as a cell within a subject, e.g., a mammal, such as a human having a Serpina1 associated disease, e.g., a liver disease, e.g., chronic liver disease, liver inflammation, cirrhosis, liver fibrosis, and/or hepatocellular carcinoma.

Accordingly, the invention provides double stranded RNAi agents with chemical modifications capable of inhibiting the expression of a target gene (i.e., a Serpina1 gene) in vivo. In certain aspects of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The RNAi agent comprises a sense strand and an antisense strand. Each strand of the RNAi agent may range from 12-30 nucleotides in length. For example, each strand may be between 14-30 nucleotides in length, 17-30 nucleotides in length, 19-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

Any of the nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science,* 1991, 254, 1497-1500.

Some embodiments featured in the invention include RNAs with phosphorothioate backbones and oligonucleosides with heteroatom backbones, and in particular $—CH_2—NH—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—CH_2—$ [wherein the native phosphodiester backbone is represented as $—O—P—O—CH_2—$] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)._nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78:486-504) i.e., an alkoxy-alkoxy group. Another exemplary modification is 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_2)_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$) and 2'-fluoro (2'-F) Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA of the invention can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., (1991) *Angewandte Chemie, International Edition,* 30:613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

An iRNA of the invention can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

An iRNA of the invention can also be modified to include one or more bicyclic sugar moities. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-(CH2)-O-2' (LNA);

4'-(CH2)-S-2'; 4'-(CH2)2-O-2' (ENA); 4'-CH(CH3)-O-2' (also referred to as "constrained ethyl" or "cEt") and 4'-CH (CH2OCH3)-O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(OCH3)-2' (and analogs thereof; see e.g., U.S. Pat. No. 8,278,425); 4'-CH2-O—N(CH3)-2' (see, e.g., U.S. Patent Publication No. 2004/0171570); 4'-CH2-N(R)—O-2', wherein R is H, C1-C12 alkyl, or a protecting group (see, e.g., U.S. Pat. No. 7,427,672); 4'-CH2-C(H)(CH3)-2' (see, e.g., Chattopadhyaya et al., *J. Org. Chem.*, 2009, 74, 118-134); and 4'-CH2-C(=CH2)-2' (and analogs thereof; see, e.g., U.S. Pat. No. 8,278,426). The entire contents of each of the foregoing are hereby incorporated herein by reference.

Additional representative U.S. patents and US patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

An iRNA of the invention can also be modified to include one or more constrained ethyl nucleotides. As used herein, a "constrained ethyl nucleotide" or "cEt" is a locked nucleic acid comprising a bicyclic sugar moiety comprising a 4'-CH(CH3)-0-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

In some embodiments, an iRNA of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-0-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

A. iRNAs Comprising Thermally Destabilizing Modifications.

As described herein, it has been discovered inter alia that off-target effects of dsRNA agents targeting Serpina1 can be reduced or inhibited by incorporating thermally destabilizing nucleotides at certain positions in the antisense strand of the dsRNA. With these thermally destabilizing modifications at certain positions in antisense strand, the dsRNA agents were able to retain gene silencing activity similar to the parent dsRNA while having reduced off-target gene silencing. Further, the number of off-target genes that are down-regulated or up-regulated is also reduced by dsRNA agents comprising these thermally destabilizing modifications when compared to the parent dsRNA.

As such, in one aspect, the invention provides a double stranded RNAi (dsRNA) agent capable of inhibiting expression of a Serpina1 target gene. Generally, the dsRNA agents of the invention show high on-target gene silencing while reducing or minimizing off-target gene silencing and/or toxicity. Without limitations, the dsRNA agents of the invention can be substituted for the dsRNA agents and can be used for in RNA interference based gene silencing techniques, including, but not limited to, in vitro or in vivo applications.

Generally, the dsRNA agent comprises a sense strand (also referred to as passenger strand) and an antisense strand (also referred to as guide strand). Each strand of the dsRNA agent can range from 12-40 nucleotides in length. For example, each strand can be between 14-40 nucleotides in length, 17-37 nucleotides in length, 25-37 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length. Without limitations, the sense and antisense strands can be equal length or unequal length.

In some embodiments, the antisense strand is of length 18 to 35 nucleotides. In some embodiments, the antisense strand is 21-25, 19-25, 19-21 or 21-23 nucleotides in length. In some particular embodiments, the antisense strand is 23 nucleotides in length Similar to the antisense strand, the sense strand can be, in some embodiments, 18-35 nucleotides in length. In some embodiments, the sense strand is 21-25, 19-25, 19-21 or 21-23 nucleotides in length. In some particular embodiments, the antisense strand is 21 nucleotides in length.

In some embodiments, the sense and antisense strands are independently 19, 20, 21, 22, 23, 24 or 25 nucleotides in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 18, 19, 21, 22, 23, 24 or 24 nucleotide pairs in length; and (viii) the dsRNA comprises a blunt end at 5'-end of the sense strand. In some particular embodiments, sense strand is 19, 20 or 21 or 22 nucleotides in length and the antisense strand is 20, 21 or 22 nucleotides in length.

The sense strand and antisense strand typically form a duplex dsRNA. The duplex region of a dsRNA agent may be 12-40 nucleotide pairs in length. For example, the duplex region can be between 14-40 nucleotide pairs in length, 17-30 nucleotide pairs in length, 25-35 nucleotides in length, 27-35 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotide pairs in length.

In some embodiments, the dsRNA agent of the invention has a duplex region of 12-40 nucleotides pairs in length, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications; and (vii) the dsRNA comprises a blunt end at 5'-end of the antisense strand. In some particular embodiments, the duplex region is 18, 19, 20, 21, 22 or 23 nucleotides pairs in length. In a particular embodiment, the duplex region is 21 nucleotide pairs in length.

In some embodiments, the dsRNA agent of the invention comprises one or more overhang regions and/or capping groups of dsRNA agent at the 3'-end, or 5'-end or both ends of a strand. The overhang can be 1-10 nucleotides in length, 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In some embodiments, the nucleotides in the overhang region of the dsRNA agent of the invention can each independently be a modified or unmodified nucleotide including, but not limited to 2'-sugar modified, such as, 2-F 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA agent of the invention may be phosphorylated. In some embodiments, the overhang region contains two nucleotides having a phosphorothioate between the two nucleotides, where the two nucleotides can be the same or different. In some embodiments, the overhang is present at the 3'-end of the sense strand, antisense strand or both strands. In some embodiments, this 3'-overhang is present in the antisense strand. In some embodiments, this 3'-overhang is present in the sense strand.

The dsRNA agent of the invention may comprise only a single overhang, which can strengthen the interference activity of the dsRNA, without affecting its overall stability. For example, the single-stranded overhang is located at the 3'-terminal end of the sense strand or, alternatively, at the 3'-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process. For example the single overhang comprises at least two, three, four, five, six, seven, eight, nine, or ten nucleotides in length. In some embodiments, the dsRNA has a 2 nucleotide overhang on the 3'-end of the antisense strand and a blunt end at the 5'-end of the antisense strand.

In some embodiments, one end of the dsRNA is a blunt end and the other end has an overhang, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) and the dsRNA comprises a duplex region of 12-40 nucleotide pairs in length. In some embodiments, the overhang is on the 3'-end of the antisense strand and the blunt end is at the 5'-end of the antisense strand. In some particular embodiments, the overhang is 2, 3 or 4-nucleotides in length.

In some embodiments, the dsRNA agent has a duplex region of 19, 21, 22 or 23 nucleotide base pairs in length, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications, and optionally the 2 nucleotide overhang is on the 3'-end of the antisense strand and the blunt end is at the 5'-end of the antisense strand. In some embodiments, the overhang is on the 3'-end of the antisense strand and the blunt end is at the 5'-end of the antisense strand.

In some embodiments, the dsRNA agent of the invention may also have two blunt ends, at both ends of the dsRNA duplex.

In some embodiments, the dsRNA has a blunt end at both ends of the duplex, wherein the antisense strand contains at least one thermally destabilizing nucleotide, and where the at least one thermally destabilizing nucleotide is in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and (vii) the dsRNA comprises a duplex region of 12-40 nucleotide pairs in length.

In some embodiments, the dsRNA agent has a duplex region of 19, 21, 22 or 23 nucleotide base pairs in length and has a blunt end at both ends of the duplex, wherein one end of the dsRNA is a blunt end and the other end has an overhang, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, five or all six) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications.

In some embodiments, the antisense strand comprises at least one (e.g., one, two, three, four, five or more) thermally destabilizing modification of the duplex within the first 9 nucleotide positions of the 5' region of the antisense strand. In some embodiments, thermally destabilizing modification of the duplex is located in positions 2-9, or preferably positions 4-8, from the 5'-end of the antisense strand. In some further embodiments, the thermally destabilizing modification of the duplex is located at position 6, 7 or 8 from the 5'-end of the antisense strand. In still some further embodiments, the thermally destabilizing modification of the duplex is located at position 7 from the 5'-end of the antisense strand. The term "thermally destabilizing modification(s)" includes modification(s) that would result with a dsRNA with a lower overall melting temperature (Tm) (preferably a Tm with one, two, three or four degrees lower than the Tm of the dsRNA without having such modification(s).

The thermally destabilizing modifications can include, but are not limited to, abasic modification; mismatch with the opposing nucleotide in the opposing strand; and sugar modification such as 2'-deoxy modification or acyclic nucleotide, e.g., unlocked nucleic acids (UNA) or glycol nucleic acid (GNA).

Exemplified abasic modifications include, but are not limited to the following:

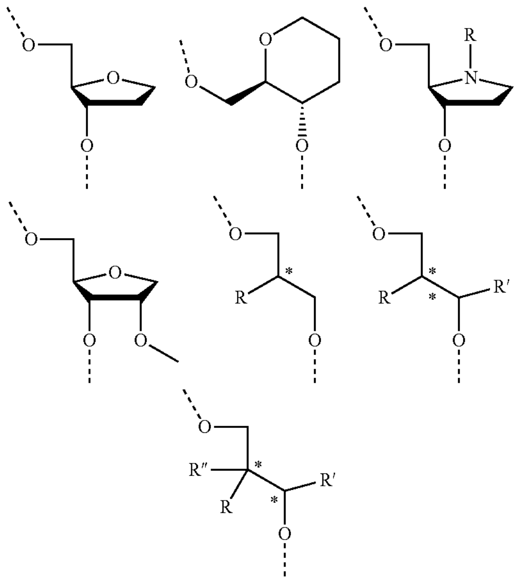

Wherein R=H, Me, Et or OMe; R'=H, Me, Et or OMe; R''=H, Me, Et or OMe

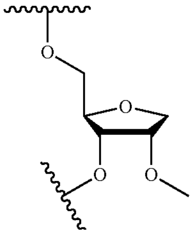

Mod2
(2'-OMe Abasic
Spacer)

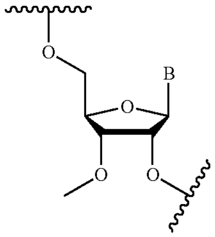

Mod3
(3'-OMe)

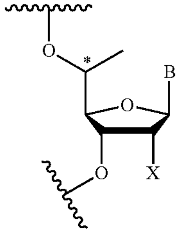

Mod4
(5'-Me)
X = OMe, F

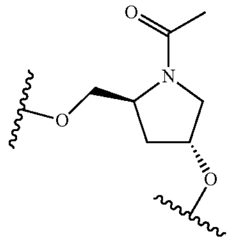

Mod5
(Hyp-spacer)

wherein B is a modified or unmodified nucleobase.

Exemplified sugar modifications include, but are not limited to the following:

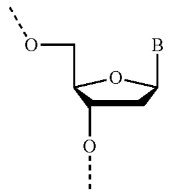

2′-deoxy

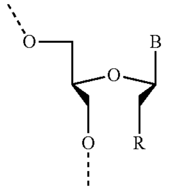

unlocked nucleic acid
R = H, OH, O-alkyl

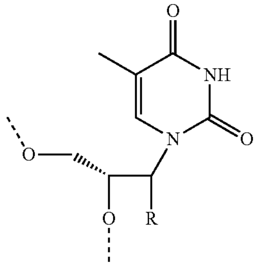

glycol nucleic acid
R = H, OH, O-alkyl

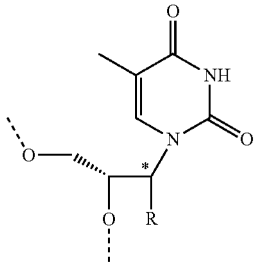

glycol nucleic acid
R = H, OH, O-alkyl

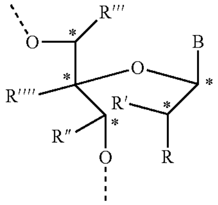

unlocked nucleic acid
R = H, OH, $CH_3$, $CH_2CH_3$, O-alkyl, $NH_2$, NHMe, $NMe_2$
R′ = H, OH, $CH_3$, $CH_2CH_3$, O-alkyl, $NH_2$, NHMe, $NMe_2$
R″ = H, OH, $CH_3$, $CH_2CH_3$, O-alkyl, $NH_2$, NHMe, $NMe_2$
R‴ = H, OH, $CH_3$, $CH_2CH_3$, O-alkyl, $NH_2$, NHMe, $NMe_2$
R⁗ = H, OH, $CH_3$, $CH_2CH_3$, O-alkyl, $NH_2$, NHMe, $NMe_2$ -continued

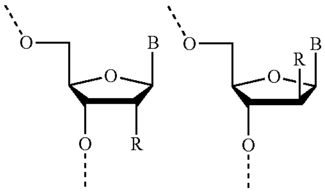

R = H, methyl, ethyl wherein B is a modified or unmodified nucleobase.

In some embodiments the thermally destabilizing modification of the duplex is selected from the group consisting of:

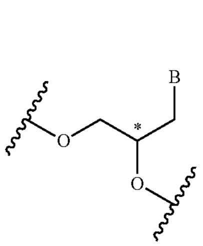,

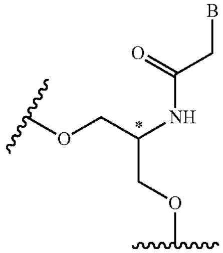,

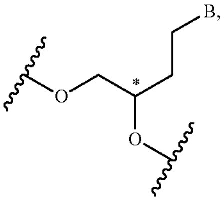

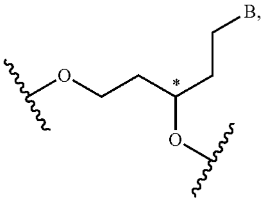

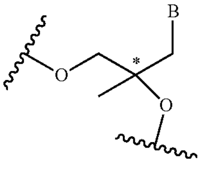, and

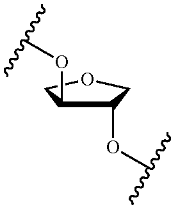, wherein B is a modified or unmodified nucleobase.

The term "acyclic nucleotide" refers to any nucleotide having an acyclic ribose sugar, for example, where any of bonds between the ribose carbons (e.g., C1'-C2', C2'-C3', C3'-C4', C4'-04', or C1'-04') is absent and/or at least one of ribose carbons or oxygen (e.g., C1', C2', C3', C4' or 04') are independently or in combination absent from the nucleotide. In some embodiments, acyclic nucleotide is

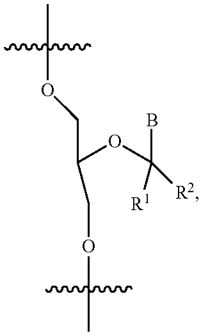

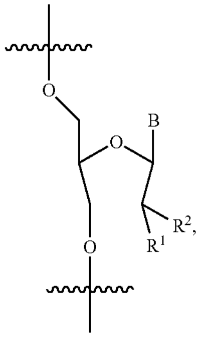

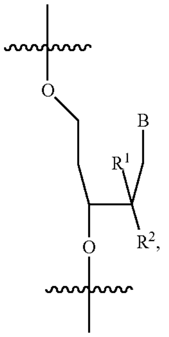

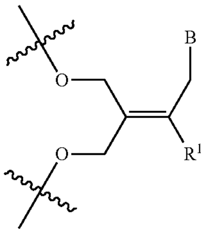

or

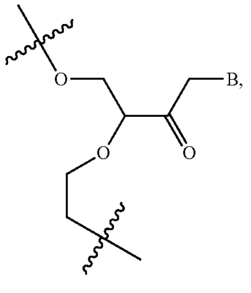

wherein B is a modified or unmodified nucleobase, $R^1$ and $R^2$ independently are H, halogen, $OR_3$, or alkyl; and $R_3$ is H, alkyl, cycloalkyl, aryl, aralkyl, heteroaryl or sugar). The term "UNA" refers to unlocked acyclic nucleic acid, wherein any of the bonds of the sugar has been removed, forming an unlocked "sugar" residue. In one example, UNA also encompasses monomers with bonds between C1'-C4' being removed (i.e. the covalent carbon-oxygen-carbon bond between the C1' and C4' carbons). In another example, the C2'-C3' bond (i.e. the covalent carbon-carbon bond between the C2' and C3' carbons) of the sugar is removed (see Mikhailov et. al., *Tetrahedron* Letters, 26 (17): 2059 (1985); and Fluiter et al., *Mol. Biosyst.,* 10: 1039 (2009), which are hereby incorporated by reference in their entirety). The acyclic derivative provides greater backbone flexibility without affecting the Watson-Crick pairings. The acyclic nucleotide can be linked via 2'-5' or 3'-5' linkage.

The term 'GNA' refers to glycol nucleic acid which is a polymer similar to DNA or RNA but differing in the composition of its "backbone" in that is composed of repeating glycerol units linked by phosphodiester bonds:

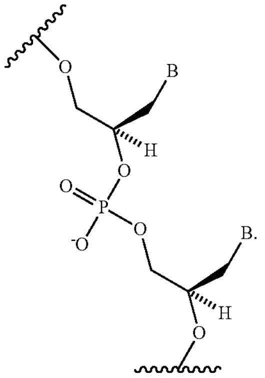

(R)-GNA

The thermally destabilizing modification of the duplex can be mismatches (i.e., noncomplementary base pairs) between the thermally destabilizing nucleotide and the opposing nucleotide in the opposite strand within the dsRNA duplex. Exemplary mismatch base pairs include G:G, G:A, G:U, G:T, A:A, A:C, C:C, C:U, C:T, U:U, T:T, U:T, or a combination thereof. Other mismatch base pairings known in the art are also amenable to the present invention. A mismatch can occur between nucleotides that are either naturally occurring nucleotides or modified nucleotides, i.e., the mismatch base pairing can occur between the nucleobases from respective nucleotides independent of the modifications on the ribose sugars of the nucleotides. In certain embodiments, the dsRNA agent contains at least one nucleobase in the mismatch pairing that is a 2'-deoxy nucleobase; e.g., the 2'-deoxy nucleobase is in the sense strand.

In some embodiments, the thermally destabilizing modification of the duplex in the seed region of the antisense strand includes nucleotides with impaired W—C H-bonding to complementary base on the target mRNA, such as:

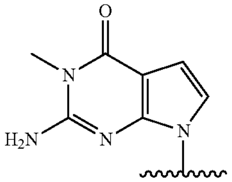

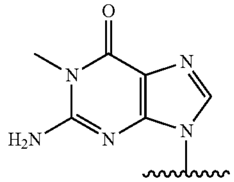

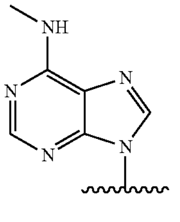

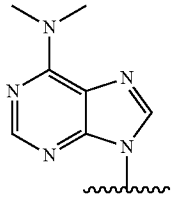

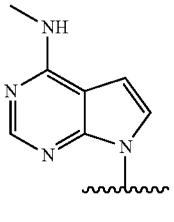

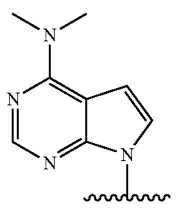

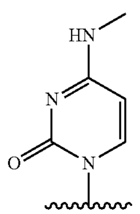

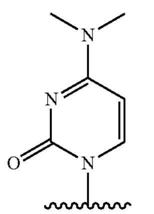

-continued

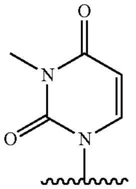
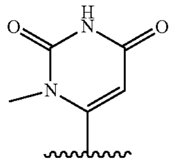
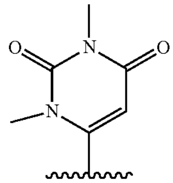

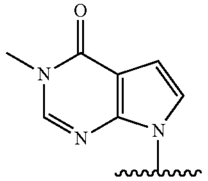
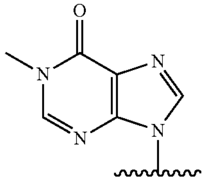

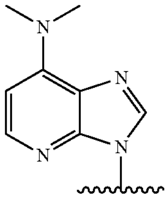
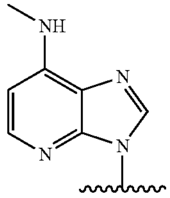
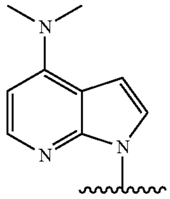

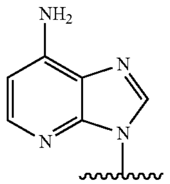
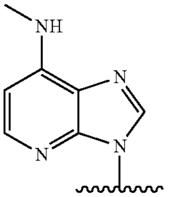
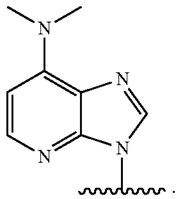

More examples of abasic nucleotide, acyclic nucleotide modifications (including UNA and GNA), and mismatch modifications have been described in detail in WO 2011/133876, which is herein incorporated by reference in its entirety.

The thermally destabilizing modifications may also include universal base with reduced or abolished capability to form hydrogen bonds with the opposing bases, and phosphate modifications.

In some embodiments, the thermally destabilizing modification of the duplex includes nucleotides with non-canonical bases such as, but not limited to, nucleobase modifications with impaired or completely abolished capability to form hydrogen bonds with bases in the opposite strand. These nucleobase modifications have been evaluated for destabilization of the central region of the dsRNA duplex as described in WO 2010/0011895, which is herein incorporated by reference in its entirety. Exemplary nucleobase modifications are:

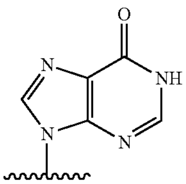
inosine

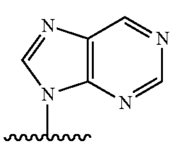
nebularine

-continued

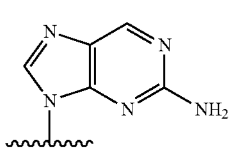
2-aminopurine

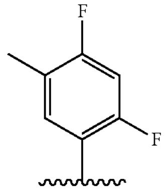
2,4-difluorotoluene

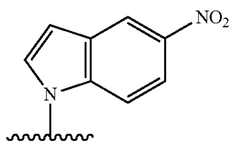
5-nitroindole

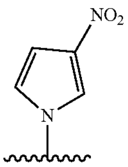
3-nitropyrrole

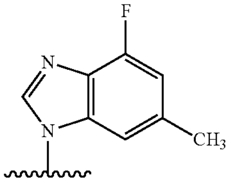
4-Fluoro-6-methylbenzimidazole

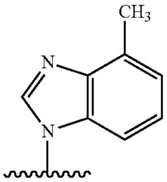
4-Methylbenzimidazole

In some embodiments, the thermally destabilizing modification of the duplex in the seed region of the antisense strand includes one or more α-nucleotide complementary to the base on the target mRNA, such as:

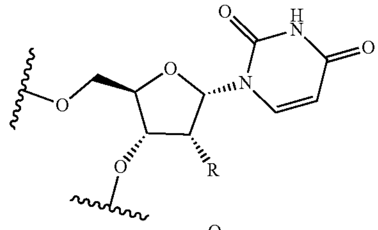

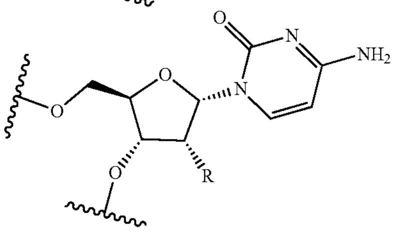

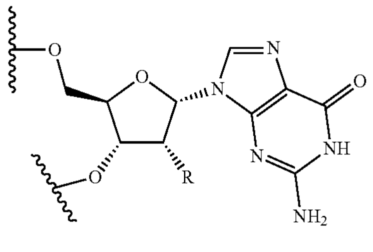

-continued

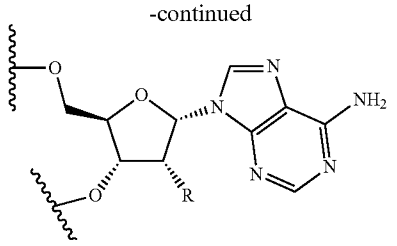

Wherein R is H, OH, $OCH_3$, F, $NH_2$, NHMe, $NMe_2$ or O-alkyl

Exemplary phosphate modifications known to decrease the thermal stability of dsRNA duplexes compared to natural phosphodiester linkages are:

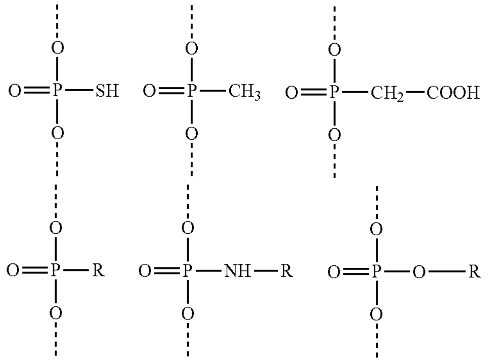

R = alkyl

The alkyl for the R group can be a $C_1$-$C_6$alkyl. Specific alkyls for the R group include, but are not limited to methyl, ethyl, propyl, isopropyl, butyl, pentyl and hexyl. In addition to the antisense strand comprising a thermally destabilizing modification, the dsRNA can also comprise one or more stabilizing modifications. For example, the dsRNA can comprise at least two (e.g., two, three, four, five, six, seven, eight, nine, ten or more) stabilizing modifications. Without limitations, the stabilizing modifications all can be present in one strand. In some embodiments, both the sense and the antisense strands comprise at least two stabilizing modifications. The stabilizing modification can occur on any nucleotide of the sense strand or antisense strand. For instance, the stabilizing modification can occur on every nucleotide on the sense strand and/or antisense strand; each stabilizing modification can occur in an alternating pattern on the sense strand or antisense strand; or the sense strand or antisense strand comprises both stabilizing modification in an alternating pattern. The alternating pattern of the stabilizing modifications on the sense strand may be the same or different from the antisense strand, and the alternating pattern of the stabilizing modifications on the sense strand can have a shift relative to the alternating pattern of the stabilizing modifications on the antisense strand.

In some embodiments, the antisense strand comprises at least two (e.g., two, three, four, five, six, seven, eight, nine, ten or more) stabilizing modifications. Without limitations, a stabilizing modification in the antisense strand can be present at any positions. In some embodiments, the antisense comprises stabilizing modifications at positions 2, 6, 8, 9, 14 and 16 from the 5'-end. In some other embodiments, the antisense comprises stabilizing modifications at positions 2, 6, 14 and 16 from the 5'-end. In still some other embodiments, the antisense comprises stabilizing modifications at positions 2, 14 and 16 from the 5'-end.

In some embodiments, the antisense strand comprises at least one stabilizing modification adjacent to the destabilizing modification. For example, the stabilizing modification can be the nucleotide at the 5'-end or the 3'-end of the destabilizing modification, i.e., at position −1 or +1 from the position of the destabilizing modification. In some embodiments, the antisense strand comprises a stabilizing modification at each of the 5'-end and the 3'-end of the destabilizing modification, i.e., positions −1 and +1 from the position of the destabilizing modification.

In some embodiments, the antisense strand comprises at least two stabilizing modifications at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) stabilizing modifications. Without limitations, a stabilizing modification in the sense strand can be present at any positions. In some embodiments, the sense strand comprises stabilizing modifications at positions 7, 10 and 11 from the 5'-end. In some other embodiments, the sense strand comprises stabilizing modifications at positions 7, 9, 10 and 11 from the 5'-end. In some embodiments, the sense strand comprises stabilizing modifications at positions opposite or complimentary to positions 11, 12 and 15 of the antisense strand, counting from the 5'-end of the antisense strand. In some other embodiments, the sense strand comprises stabilizing modifications at positions opposite or complimentary to positions 11, 12, 13 and 15 of the antisense strand, counting from the 5'-end of the antisense strand. In some embodiments, the sense strand comprises a block of two, three or four stabilizing modifications.

In some embodiments, the sense strand does not comprise a stabilizing modification in position opposite or complimentary to the thermally destabilizing modification of the duplex in the antisense strand.

Exemplary thermally stabilizing modifications include, but are not limited to 2'-fluoro modifications.

In some embodiments, the dsRNA of the invention comprises at least four (e.g., four, five, six, seven, eight, nine, ten or more) 2'-fluoro nucleotides. Without limitations, the 2'-fluoro nucleotides all can be present in one strand. In some embodiments, both the sense and the antisense strands comprise at least two 2'-fluoro nucleotides. The 2'-fluoro modification can occur on any nucleotide of the sense strand or antisense strand. For instance, the 2'-fluoro modification can occur on every nucleotide on the sense strand and/or antisense strand; each 2'-fluoro modification can occur in an alternating pattern on the sense strand or antisense strand; or the sense strand or antisense strand comprises both 2'-fluoro modifications in an alternating pattern. The alternating pattern of the 2'-fluoro modifications on the sense strand may be the same or different from the antisense strand, and the alternating pattern of the 2'-fluoro modifications on the sense strand can have a shift relative to the alternating pattern of the 2'-fluoro modifications on the antisense strand.

In some embodiments, the antisense strand comprises at least two (e.g., two, three, four, five, six, seven, eight, nine, ten or more) 2'-fluoro nucleotides. Without limitations, a 2'-fluoro modification in the antisense strand can be present at any positions. In some embodiments, the antisense comprises 2'-fluoro nucleotides at positions 2, 6, 8, 9, 14 and 16 from the 5'-end. In some other embodiments, the antisense comprises 2'-fluoro nucleotides at positions 2, 6, 14 and 16 from the 5'-end. In still some other embodiments, the antisense comprises 2'-fluoro nucleotides at positions 2, 14 and 16 from the 5'-end.

In some embodiments, the antisense strand comprises at least one 2'-fluoro nucleotide adjacent to the destabilizing modification. For example, the 2'-fluoro nucleotide can be the nucleotide at the 5'-end or the 3'-end of the destabilizing modification, i.e., at position −1 or +1 from the position of the destabilizing modification. In some embodiments, the antisense strand comprises a 2'-fluoro nucleotide at each of the 5'-end and the 3'-end of the destabilizing modification, i.e., positions −1 and +1 from the position of the destabilizing modification.

In some embodiments, the antisense strand comprises at least two 2'-fluoro nucleotide at the 3'-end of the destabilizing modification, i.e., at positions +1 and +2 from the position of the destabilizing modification.

In some embodiments, the sense strand comprises at least two (e.g., two, three, four, five, six, seven, eight, nine, ten or more) 2'-fluoro nucleotides. Without limitations, a 2'-fluoro modification in the sense strand can be present at any positions. In some embodiments, the antisense comprises 2'-fluoro nucleotides at positions 7, 10 and 11 from the 5'-end. In some other embodiments, the sense strand comprises 2'-fluoro nucleotides at positions 7, 9, 10 and 11 from the 5'-end. In some embodiments, the sense strand comprises 2'-fluoro nucleotides at positions opposite or complimentary to positions 11, 12 and 15 of the antisense strand, counting from the 5'-end of the antisense strand. In some other embodiments, the sense strand comprises 2'-fluoro nucleotides at positions opposite or complimentary to positions 11, 12, 13 and 15 of the antisense strand, counting from the 5'-end of the antisense strand. In some embodiments, the sense strand comprises a block of two, three or four 2'-fluoro nucleotides.

In some embodiments, the sense strand does not comprise a 2'-fluoro nucleotide in position opposite or complimentary to the thermally destabilizing modification of the duplex in the antisense strand.

In some embodiments, the dsRNA agent of the invention comprises a 21 nucleotides (nt) sense strand and a 23 nucleotides (nt) antisense, wherein the antisense strand contains at least one thermally destabilizing nucleotide, where the at least one thermally destabilizing nucleotide occurs in the seed region of the antisense strand (i.e., at position 2-9 of the 5'-end of the antisense strand), wherein one end of the dsRNA is blunt, while the other end is comprises a 2 nt overhang, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; and (vii) the dsRNA comprises a blunt end at 5'-end of the antisense strand. Preferably, the 2 nt overhang is at the 3'-end of the antisense.

In some embodiments, the dsRNA agent of the invention comprising a sense and antisense strands, wherein: the sense strand is 25-30 nucleotide residues in length, wherein starting from the 5' terminal nucleotide (position 1), positions 1 to 23 of said sense strand comprise at least 8 ribonucleotides; antisense strand is 36-66 nucleotide residues in length and, starting from the 3' terminal nucleotide, at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the antisense strand contains at least one thermally destabilizing nucleotide, where at least one thermally destabilizing nucleotide is in the seed region of the antisense strand (i.e. at position 2-9 of the 5'-end of the antisense strand), For example, the thermally destabilizing nucleotide occurs between positions opposite or complimentary to positions 14-17 of the 5'-end of the sense strand, and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications; and (vii) the dsRNA comprises a duplex region of 12-30 nucleotide pairs in length.

In some embodiments, the dsRNA agent of the invention comprises a sense and antisense strands, wherein said dsRNA agent comprises a sense strand having a length which is at least 25 and at most 29 nucleotides and an antisense strand having a length which is at most 30 nucleotides with the sense strand comprises a modified nucleotide that is susceptible to enzymatic degradation at position 11 from the 5'end, wherein the 3' end of said sense strand and the 5' end of said antisense strand form a blunt end and said antisense strand is 1-4 nucleotides longer at its 3' end than the sense strand, wherein the duplex region which is at least 25 nucleotides in length, and said antisense strand is sufficiently complementary to a target mRNA along at least 19 nt of said antisense strand length to reduce target gene expression when said dsRNA agent is introduced into a mammalian cell, and wherein dicer cleavage of said dsRNA preferentially results in an siRNA comprising said 3' end of said antisense strand, thereby reducing expression of the target gene in the mammal, wherein the antisense strand contains at least one thermally destabilizing nucleotide, where the at least one thermally destabilizing nucleotide is in the seed region of the antisense strand (i.e. at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; and (vi) the dsRNA comprises at least four 2'-fluoro modifications; and (vii) the dsRNA has a duplex region of 12-29 nucleotide pairs in length.

In some embodiments, every nucleotide in the sense strand and antisense strand of the dsRNA agent may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking 0 of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. E.g., a phosphorothioate modification at a non-linking 0 position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In some embodiments, each residue of the sense strand and antisense strand is independently modified with LNA, HNA, CeNA, 2'-methoxyethyl, 2'-O-methyl, 2'-O-allyl, 2'-C— allyl, 2'-deoxy, or 2'-fluoro. The strands can contain more than one modification. In some embodiments, each residue of the sense strand and antisense strand is independently modified with 2'-O-methyl or 2'-fluoro. It is to be understood that these modifications are in addition to the at least one thermally destabilizing modification of the duplex present in the antisense strand.

At least two different modifications are typically present on the sense strand and antisense strand. Those two modifications may be the 2'-deoxy, 2'-O-methyl or 2'-fluoro modifications, acyclic nucleotides or others. In some embodiments, the sense strand and antisense strand each comprises two differently modified nucleotides selected from 2'-O-methyl or 2'-deoxy. In some embodiments, each residue of the sense strand and antisense strand is independently modified with 2'-O-methyl nucleotide, 2'-deoxy nucleotide, 2'-deoxyfluoro nucleotide, 2'-O—N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide. Again, it is to be understood that these modifications are in addition to the at least one thermally destabilizing modification of the duplex present in the antisense strand.

In some embodiments, the dsRNA agent of the invention comprises modifications of an alternating pattern, particular in the B1, B2, B3, B1', B2', B3', B4' regions. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In some embodiments, the dsRNA agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

The dsRNA agent of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In some embodiments, the dsRNA agent comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In some embodiments, the sense strand of the dsRNA agent comprises 1-10 blocks of two to ten phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of three phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of four phosphorothioate or methylphosphonate internucleotide linkages separated by 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of five phosphorothioate or methylphosphonate internucleotide linkages separated by 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of six phosphorothioate or methylphosphonate internucleotide linkages separated by 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of seven phosphorothioate or methylphosphonate internucleotide linkages separated by 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of eight phosphorothioate or methylphosphonate internucleotide linkages separated by 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the antisense strand of the dsRNA agent comprises two blocks of nine phosphorothioate or methylphosphonate internucleotide linkages separated by 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphosphonate or phosphate linkage.

In some embodiments, the dsRNA agent of the invention further comprises one or more phosphorothioate or methylphosphonate internucleotide linkage modification within 1-10 of the termini position(s) of the sense and/or antisense strand. For example, at least 2, 3, 4, 5, 6, 7, 8, 9 or 10 nucleotides may be linked through phosphorothioate or methylphosphonate internucleotide linkage at one end or both ends of the sense and/or antisense strand.

In some embodiments, the dsRNA agent of the invention further comprises one or more phosphorothioate or methylphosphonate internucleotide linkage modification within 1-10 of the internal region of the duplex of each of the sense and/or antisense strand. For example, at least 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA agent can optionally further comprise one or more phosphorothioate or methylphosphonate internucleotide linkage modification within 1-10 of the termini position(s).

In some embodiments, the dsRNA agent of the invention further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In some embodiments, the dsRNA agent of the invention further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In some embodiments, the dsRNA agent of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In some embodiments, the dsRNA agent of the invention further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In some embodiments, the dsRNA agent of the invention further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In some embodiments, the dsRNA agent of the invention further comprises one phosphorothioate internucleotide linkage modification within position 1-5 (counting from the 5'-end) of the sense strand, and two phosphorothioate internucleotide linkage modifications at positions 1 and 2 and one phosphorothioate internucleotide linkage modification within positions 18-23 of the antisense strand (counting from the 5'-end).

In some embodiments, the dsRNA agent of the invention further comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent of the invention further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In some embodiments, the dsRNA agent of the invention further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end). In some embodiments, the dsRNA agent of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In some embodiments, the dsRNA agent of the invention further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In some embodiments, the dsRNA agent of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In some embodiments, the dsRNA agent of the invention further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA agent of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In some embodiments, the dsRNA agent of the invention further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In some embodiments, the dsRNA agent of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In some embodiments, the antisense strand comprises phosphorothioate internucleotide linkages between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 3 or 4 phosphorothioate internucleotide linkages; (iii) the sense strand is conjugated with a ligand; (iv) the sense strand comprises 2, 3, 4 or 5 2'-fluoro modifications; (v) the sense strand comprises 1, 2, 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 1, 2, 3 or 4 phosphorothioate internucleotide linkages; (v) the dsRNA comprises at least four 2'-fluoro modifications; (vi) the dsRNA comprises a duplex region of 12-40 nucleotide pairs in length; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six, seven or all eight) of the following characteristics: (i) the antisense comprises 2, 3, 4, 5 or 6 2'-fluoro modifications; (ii) the antisense comprises 1, 2, 3 or 4 phosphorothioate internucleotide linkages; (iii) the sense strand is conjugated with a ligand;

(iv) the sense strand comprises 2, 3, 4 or 5 2'-fluoro modifications; (v) the sense strand comprises 3 or 4 phosphorothioate internucleotide linkages; (vi) the dsRNA comprises at least four 2'-fluoro modifications; (vii) the dsRNA comprises a duplex region of 12-40 nucleotide pairs in length; and (viii) the dsRNA has a blunt end at 5'-end of the antisense strand.

In some embodiments, the sense strand comprises phosphorothioate internucleotide linkages between nucleotide positions 1 and 2, and between nucleotide positions 2 and 3, the antisense strand comprises phosphorothioate internucleotide linkages between nucleotide positions 1 and 2, between nucleotide positions 2 and 3, between nucleotide positions 21 and 22, and between nucleotide positions 22 and 23, wherein the antisense strand contains at least one thermally destabilizing modification of the duplex located in the seed region of the antisense strand (i.e., at position 2-9 of the 5'-end of the antisense strand), and wherein the dsRNA optionally further has at least one (e.g., one, two, three, four, five, six or all seven) of the following characteristics: (i) the antisense comprises 2, 3, 4, 5 or 6 2'-fluoro modifications; (ii) the sense strand is conjugated with a ligand; (iii) the sense strand comprises 2, 3, 4 or 5 2'-fluoro modifications; (iv) the sense strand comprises 3 or 4 phosphorothioate internucleotide linkages; (v) the dsRNA comprises at least four 2'-fluoro modifications; (vi) the dsRNA comprises a duplex region of 12-40 nucleotide pairs in length; and (vii) the dsRNA has a blunt end at 5'-end of the antisense strand.

In some embodiments, the dsRNA agent of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In some embodiments, the dsRNA agent of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In some embodiments, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

It has also beEn discovered that introducing 4'-modified and/or 5'-modified nucleotide to the 3'-end of a phosphodiester (PO), phosphorothioate (PS), and/or phosphorodithioate (PS2) linkage of a dinucleotide at any position of single stranded or double stranded oligonucleotide can exert steric effect to the internucleotide linkage and, hence, protecting or stabilizing it against nucleases.

In some embodiments, 5'-modified nucleoside is introduced at the 3'-end of a dinucleotide at any position of single stranded or double stranded siRNA. For instance, a 5'-alkylated nucleoside may be introduced at the 3'-end of a dinucleotide at any position of single stranded or double stranded siRNA. The alkyl group at the 5' position of the ribose sugar can be racemic or chirally pure R or S isomer. An exemplary 5'-alkylated nucleoside is 5'-methyl nucleoside. The 5'-methyl can be either racemic or chirally pure R or S isomer.

In some embodiments, 4'-modified nucleoside is introduced at the 3'-end of a dinucleotide at any position of single stranded or double stranded siRNA. For instance, a 4'-alkylated nucleoside may be introduced at the 3'-end of a dinucleotide at any position of single stranded or double stranded siRNA. The alkyl group at the 4' position of the ribose sugar can be racemic or chirally pure R or S isomer. An exemplary 4'-alkylated nucleoside is 4'-methyl nucleoside. The 4'-methyl can be either racemic or chirally pure R or S isomer. Alternatively, a 4'-O-alkylated nucleoside may be introduced at the 3'-end of a dinucleotide at any position of single stranded or double stranded siRNA. The 4'-O-alkyl of the ribose sugar can be racemic or chirally pure R or S isomer. An exemplary 4'-O-alkylated nucleoside is 4'-O-methyl nucleoside. The 4'-O-methyl can be either racemic or chirally pure R or S isomer.

In some embodiments, 5'-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 5'-alkylated nucleoside is 5'-methyl nucleoside. The 5'-methyl can be either racemic or chirally pure R or S isomer.

In some embodiments, 4'-alkylated nucleoside is introduced at any position on the sense strand or antisense strand of a dsRNA, and such modification maintains or improves potency of the dsRNA. The 4'-alkyl can be either racemic or chirally pure R or S isomer. An exemplary 4'-alkylated nucleoside is 4'-methyl nucleoside. The 4'-methyl can be either racemic or chirally pure R or S isomer.

In some embodiments, 4'-O-alkylated nucleoside is introduced at any position on the sense strand or antisense strand of a dsRNA, and such modification maintains or improves potency of the dsRNA. The 5'-alkyl can be either racemic or chirally pure R or S isomer. An exemplary 4'-O-alkylated nucleoside is 4'-O-methyl nucleoside. The 4'-O-methyl can be either racemic or chirally pure R or S isomer.

In some embodiments, the dsRNA agent of the invention can comprise 2'-5' linkages (with 2'-H, 2'-OH and 2'-OMe and with P═O or P═S). For example, the 2'-5' linkages modifications can be used to promote nuclease resistance or to inhibit binding of the sense to the antisense strand, or can be used at the 5' end of the sense strand to avoid sense strand activation by RISC.

In another embodiment, the dsRNA agent of the invention can comprise L sugars (e.g., L ribose, L-arabinose with 2'-H, 2'-OH and 2'-OMe). For example, these L sugars modifications can be used to promote nuclease resistance or to inhibit binding of the sense to the antisense strand, or can be used at the 5' end of the sense strand to avoid sense strand activation by RISC.

Various publications describe multimeric siRNA which can all be used with the dsRNA of the invention. Such publications include WO2007/091269, U.S. Pat. No. 7,858, 769, WO2010/141511, WO2007/117686, WO2009/014887 and WO2011/031520 which are hereby incorporated by their entirely.

As discussed in detail below, the dsRNA agent that contains conjugations of one or more carbohydrate moieties to a dsRNA agent can optimize one or more properties of the dsRNA agent. In many cases, the carbohydrate moiety will be attached to a modified subunit of the dsRNA agent. e.g., the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In one embodiment the dsRNA agent of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3] dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The double stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

In some embodiments dsRNA agents of the invention are 5' phosphorylated or include a phosphoryl analog at the 5' prime terminus. 5'-phosphate modifications include those which are compatible with RISC mediated gene silencing. Suitable modifications include: 5'-monophosphate ($(HO)_2(O)P—O-5'$); 5'-diphosphate ($(HO)_2(O)P—O—P(HO)(O)—O-5'$); 5'-triphosphate ($(HO)_2(O)P—O—(HO)(O)P—O—P(HO)(O)—O-5'$); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2(S)P—O-5'$); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ($(HO)_2(O)P—NH-5'$, $(HO)(NH_2)(O)P—O-5'$), 5'-alkylphosphonates (R=alkyl=methyl, ethyl, isopropyl, propyl, etc., e.g. RP(OH)(O)—O-5'-, 5'-alkenylphosphonates (i.e. vinyl, substituted vinyl), $(OH)_2(O)P$-5'-CH2-), 5'-alkyletherphosphonates (R=alkylether=methoxymethyl (MeOCH2-), ethoxymethyl, etc., e.g. RP(OH)(O)—O-5'-). In one example, the modification can in placed in the antisense strand of a dsRNA agent.

III. iRNAs Conjugated to Ligands

Another modification of the RNA of an iRNA of the invention involves chemically linking to the iRNA one or more ligands, moieties or conjugates that enhance the activity, cellular distribution, or cellular uptake of the iRNA e.g., into a cell. Such moieties include but are not limited to lipid moieties such as a cholesterol moiety (Letsinger et al., *Proc. Natl. Acid. Sci. USA,* 1989, 86: 6553-6556). In other embodiments, the ligand is cholic acid (Manoharan et al., *Biorg. Med. Chem. Let.,* 1994, 4:1053-1060), a thioether, e.g., beryl-S-tritylthiol (Manoharan et al., *Ann. N.Y. Acad. Sci.,* 1992, 660:306-309; Manoharan et al., *Biorg. Med. Chem. Let.,* 1993, 3:2765-2770), a thiocholesterol (Oberhauser et al., *Nucl. Acids Res.,* 1992, 20:533-538), an aliphatic chain, e.g., dodecandiol or undecyl residues (Saison-Behmoaras et al., *EMBO J,* 1991, 10:1111-1118; Kabanov et al., *FEBS Lett.,* 1990, 259:327-330; Svinarchuk et al., *Biochimie,* 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.,* 1995, 36:3651-3654; Shea et al., *Nucl. Acids Res.,* 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylamino-carbonyloxycholesterol moiety (Crooke et al., *J. Pharmacol. Exp. Ther.,* 1996, 277:923-937).

In certain embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands do not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

In one embodiment, the ligand is is an asialoglycoprotein receptor ligand. As used herein an "an asialoglycoprotein receptor ligand" or "ASGPR ligand" is a ligand, such as a carbohydrate ligand (discussed below), that targets a dsRNA agent of the invention to hepatocytes. In certain embodiments, the ligand is a one or more galactose, e.g., an N-acetyl-galactosamine (GalNAc) or one or more GalNAc derivatives.

Other examples of ligands include dyes, intercalating agents (e.g. acridines), cross-linkers (e.g. psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)

lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins, etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated iRNAs of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems® (Foster City, Calif.). Any other methods for such synthesis known in the art may additionally or alternatively be employed. It is also known to use similar techniques to prepare other oligonucleotides, such as the phosphorothioates and alkylated derivatives.

In the ligand-conjugated iRNAs and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In certain embodiments, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In certain embodiments, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In other embodiments, the lipid based ligand binds HSA weakly or not at all, such that the conjugate will be preferably distributed to the kidney. Other moieties that target to kidney cells can also be used in place of, or in addition to, the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:29). An RFGF analogue (e.g., amino acid sequence AALLPVLLAAP (SEQ ID NO:30) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:31) and the *Drosophila* Antennapedia protein (RQIKIWFQNRRMKWKK (SEQ ID NO:32) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA further comprises a carbohydrate. The carbohydrate conjugated iRNA is advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri-, and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In certain embodiments, a carbohydrate conjugate for use in the compositions and methods of the invention is a monosaccharide.

In one embodiment, a carbohydrate conjugate for use in the compositions and methods of the invention is selected from the group consisting of:

Formula II
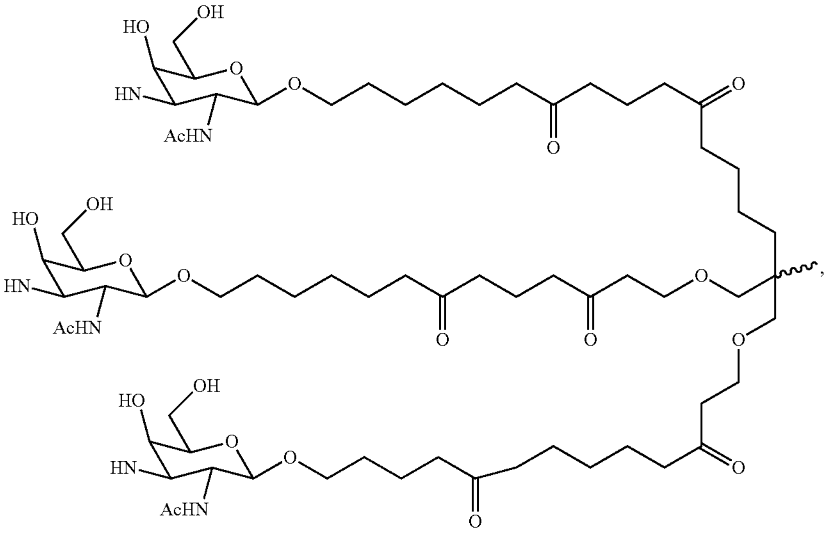
Formula III
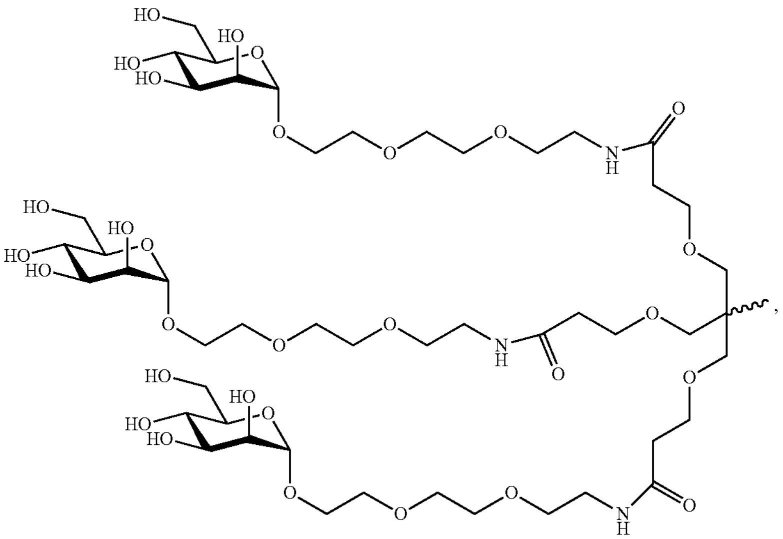
Formula IV
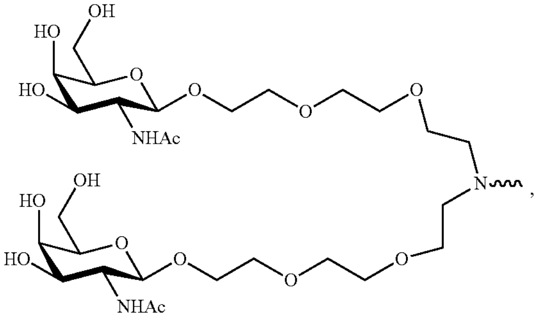
Formula V
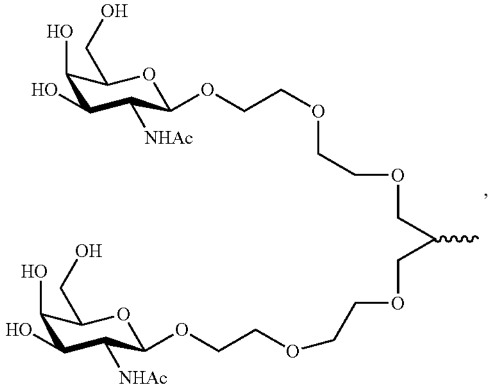

-continued
Formula VI
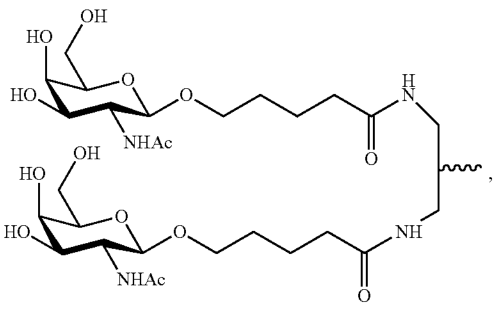
Formula VII
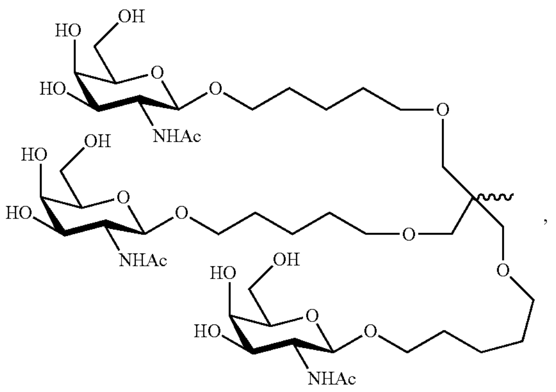
Formula VIII
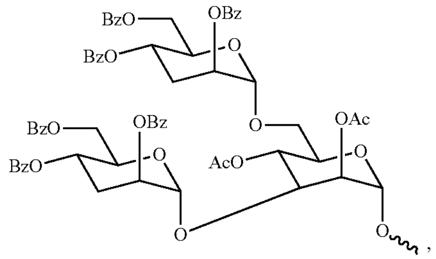
Formula IX
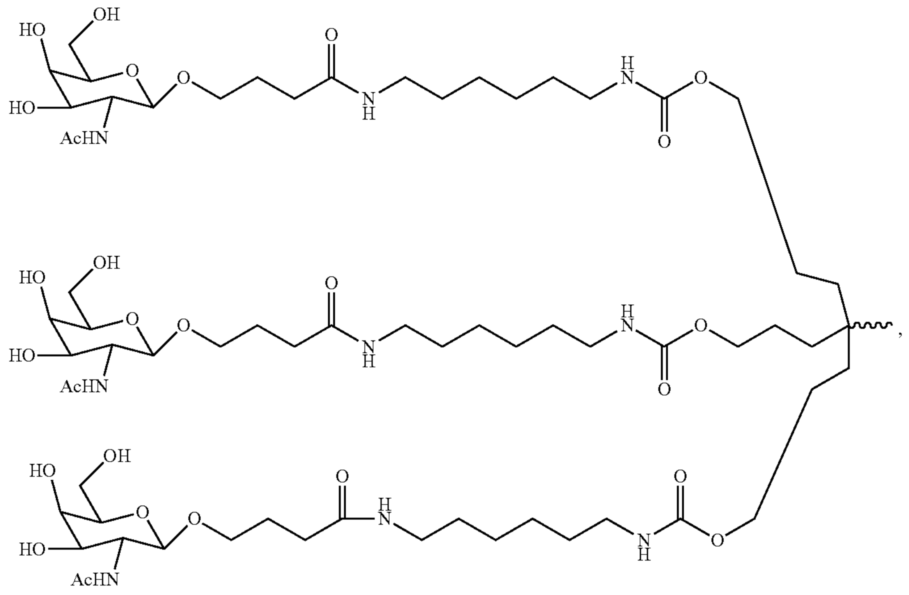

-continued
Formula X
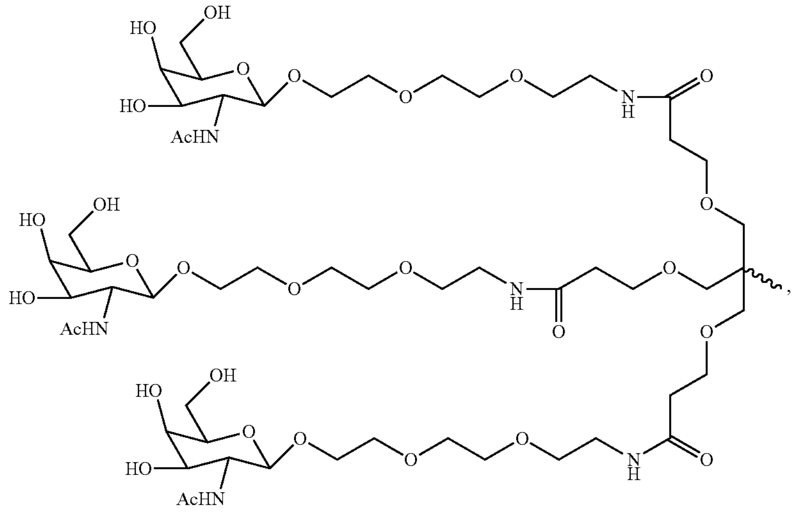
Formula XI
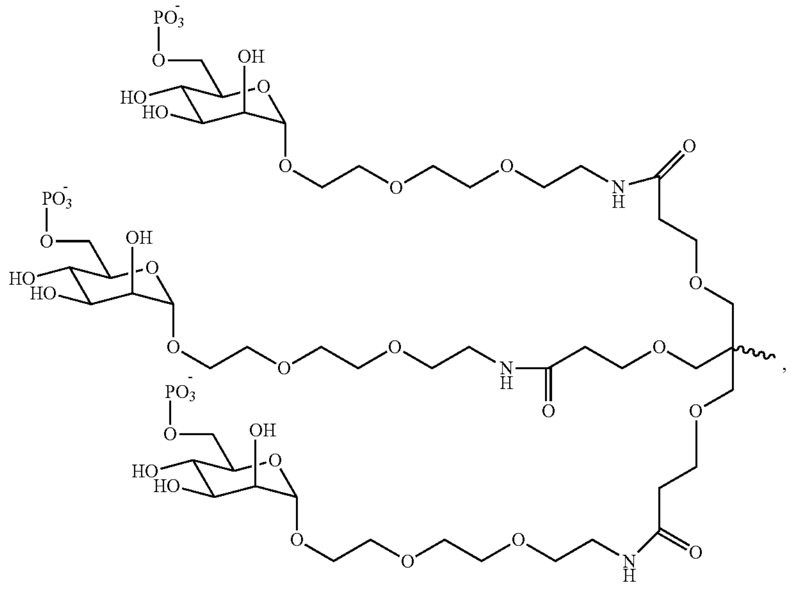

-continued
Formula XII
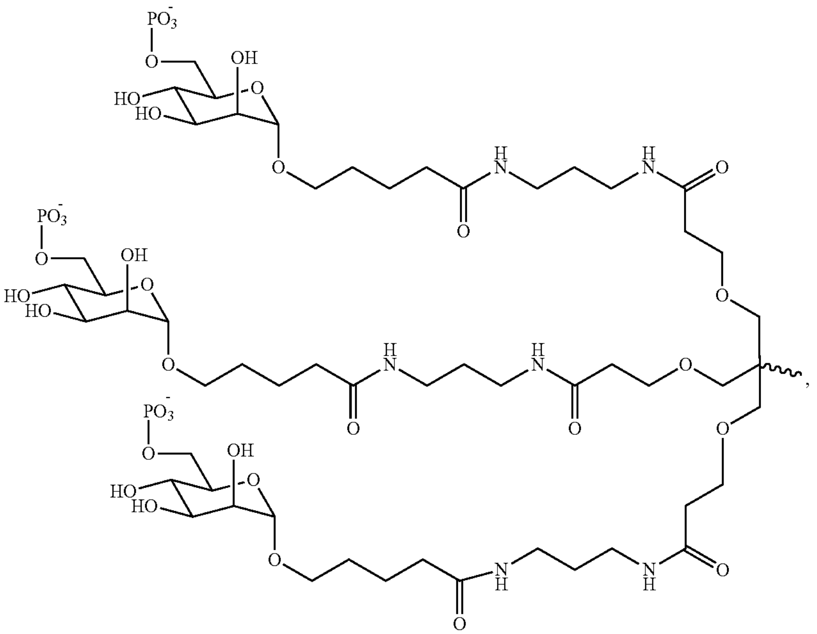
Formula XIII
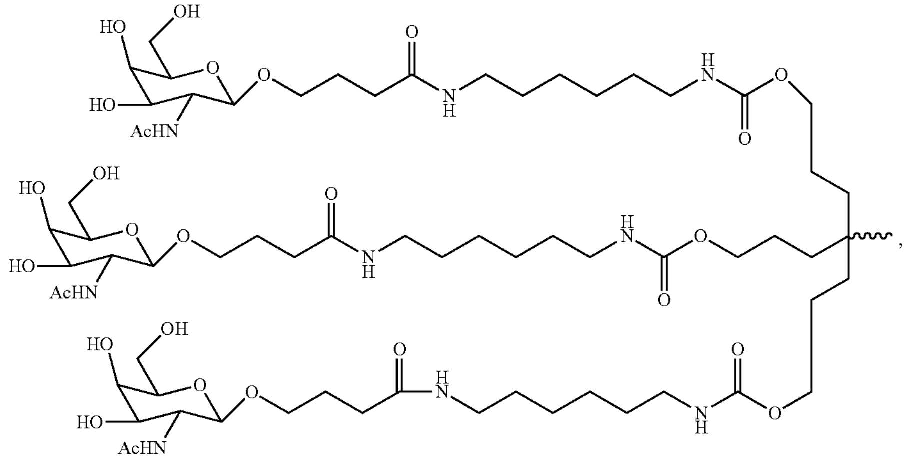
Formula XIV
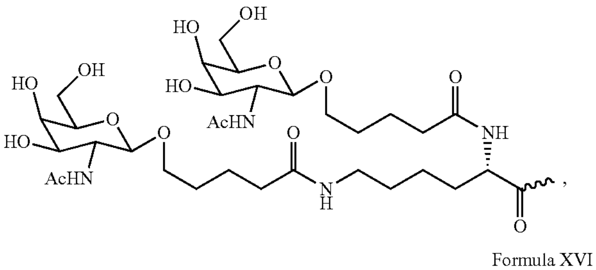
Formula XV
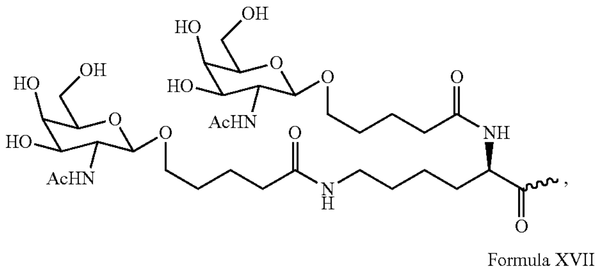
Formula XVI
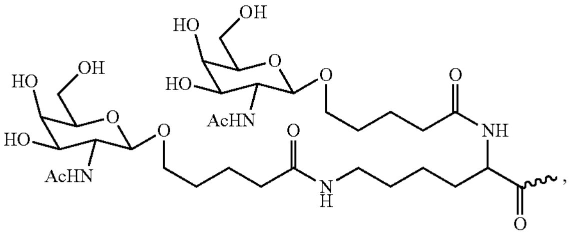
Formula XVII
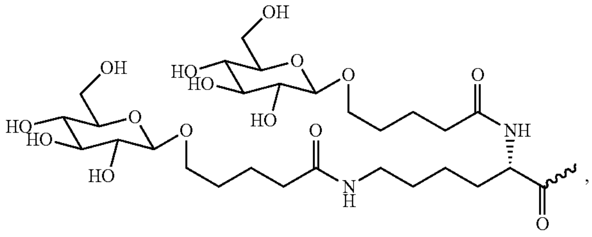

-continued
Formula XVIII
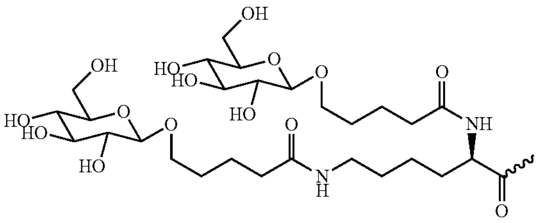
,
Formula XIX
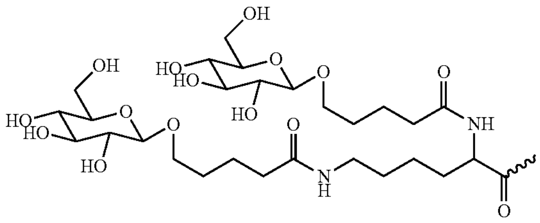
,
Formula XX
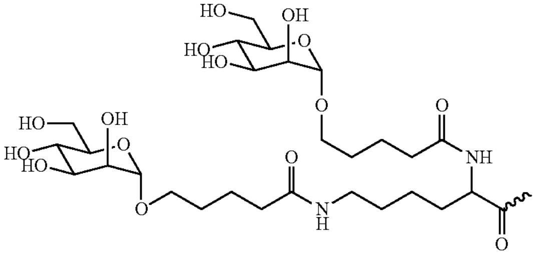
,
Formula XXI
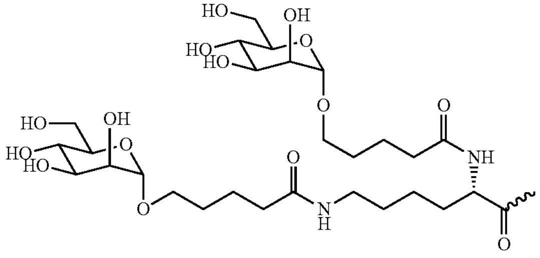
,
Formula XXII
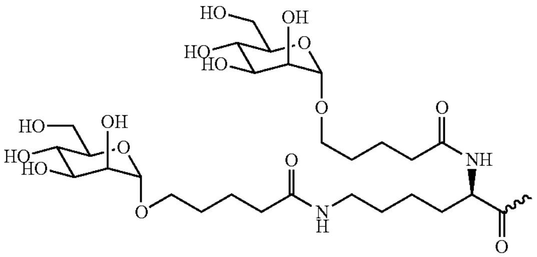
,
Formula XXIII
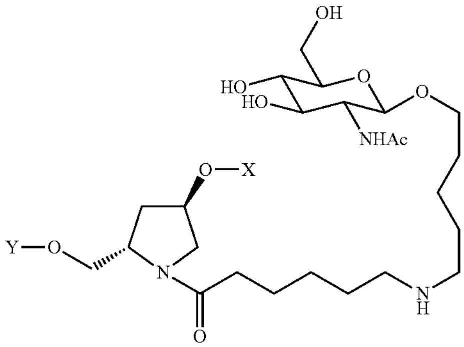
;
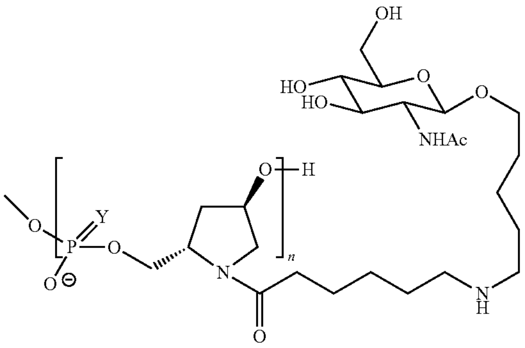
.

wherein Y is O or S and n is 3-6 (Formula XXIV);
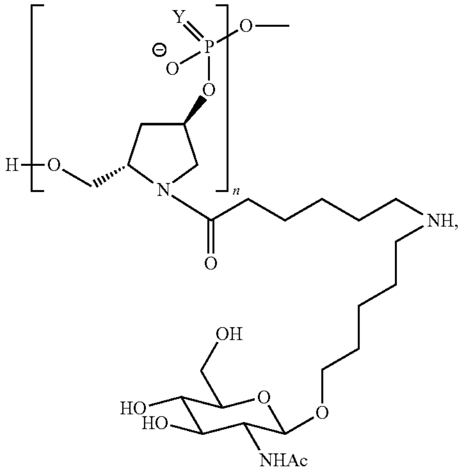
wherein Y is O or S and n is 3-6 (Formula XXV);
Formula XXVI
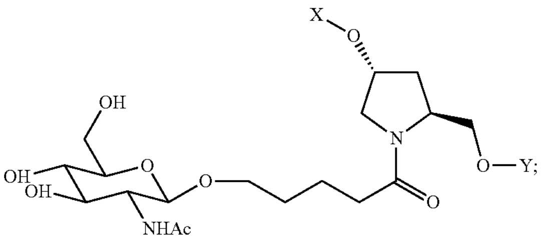
(Formula XXVII)
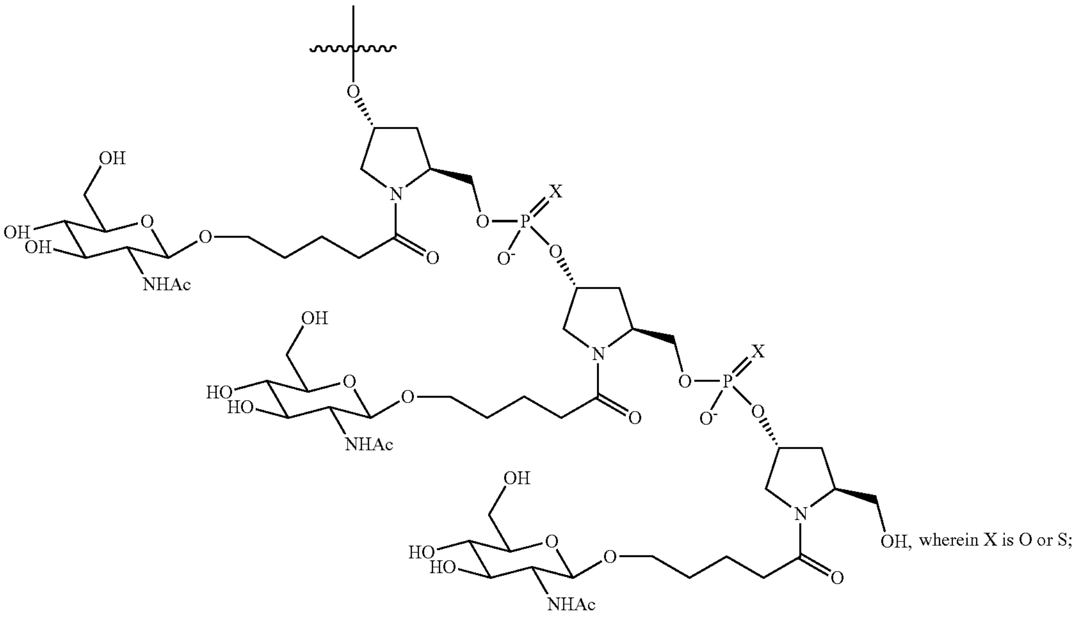
wherein X is O or S;

Formula XXVII
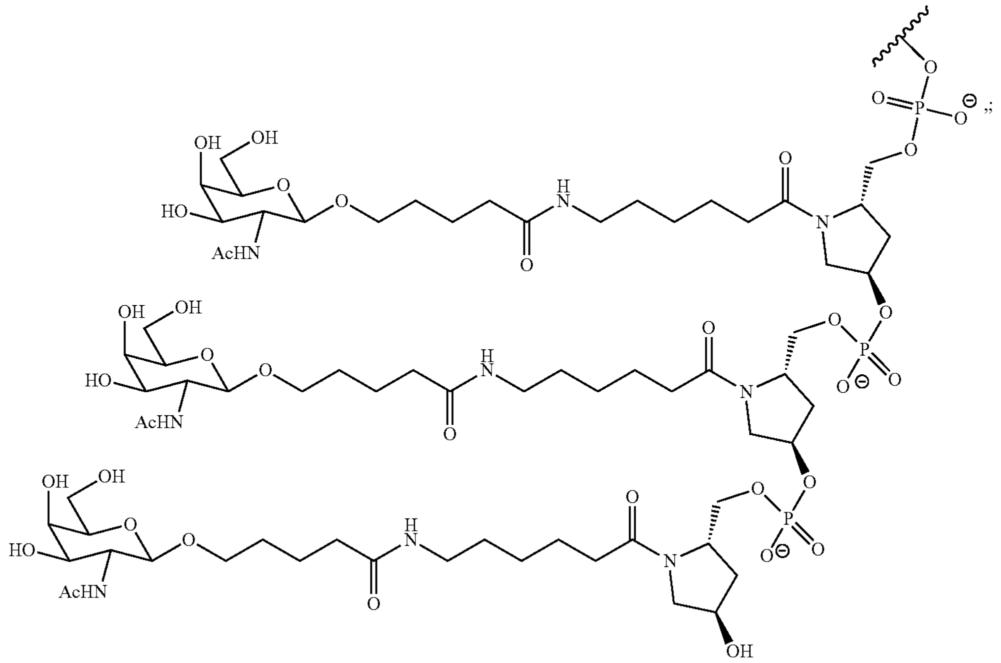
Formula XXIX
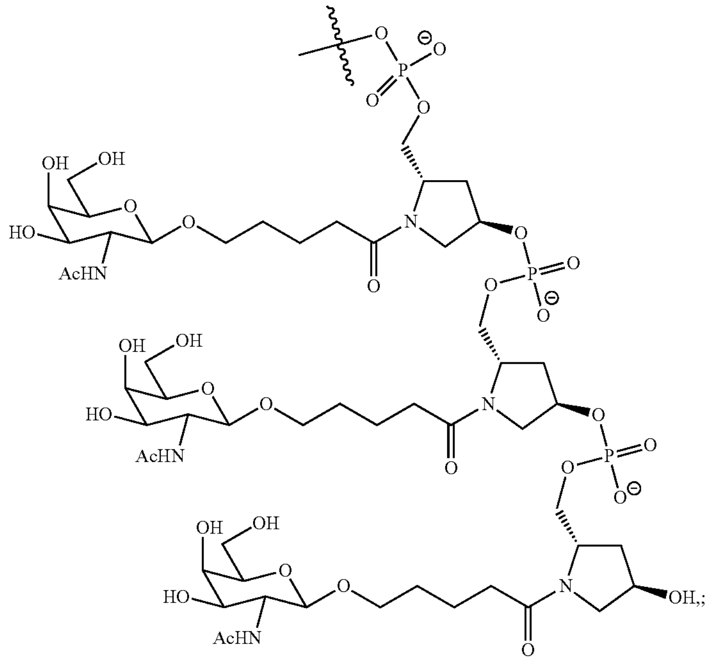

-continued
Formula XXX
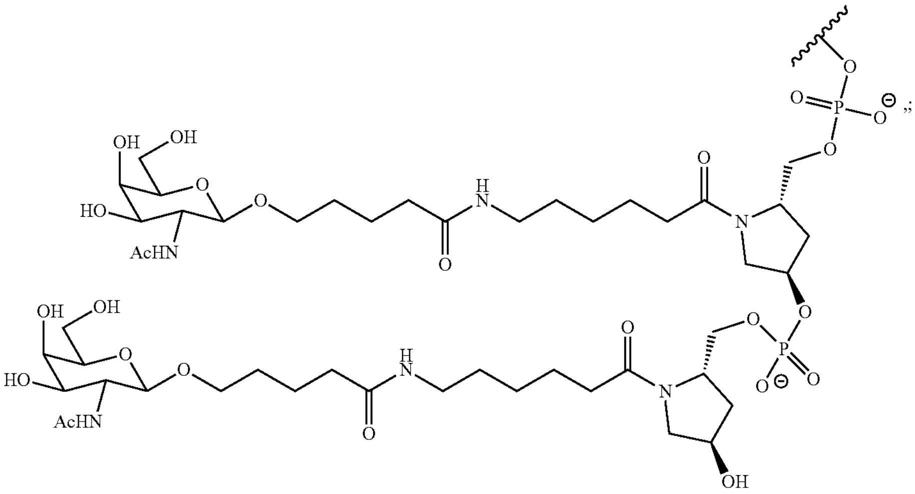
;
Formula XXXI
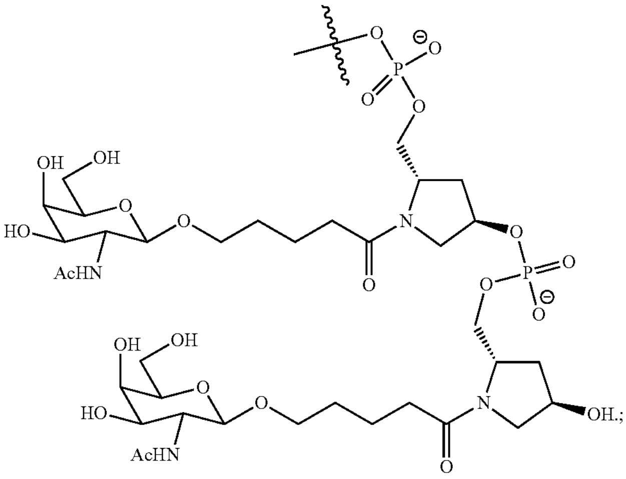
;
Formula XXXII
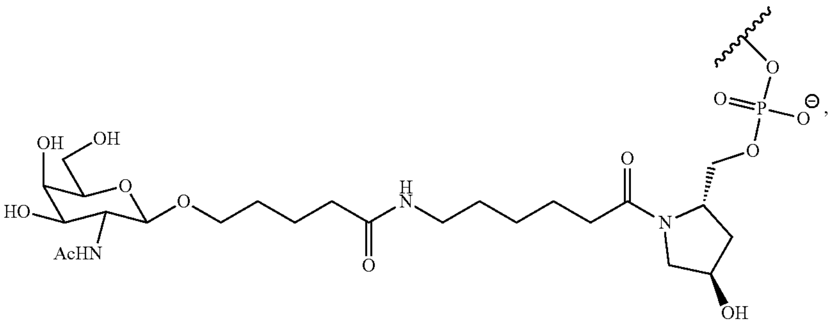
, and;

-continued
Formula XXXIII
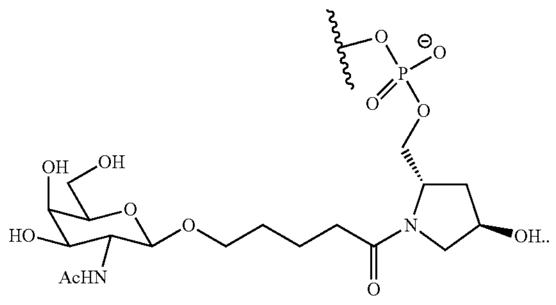
Formula XXXIV
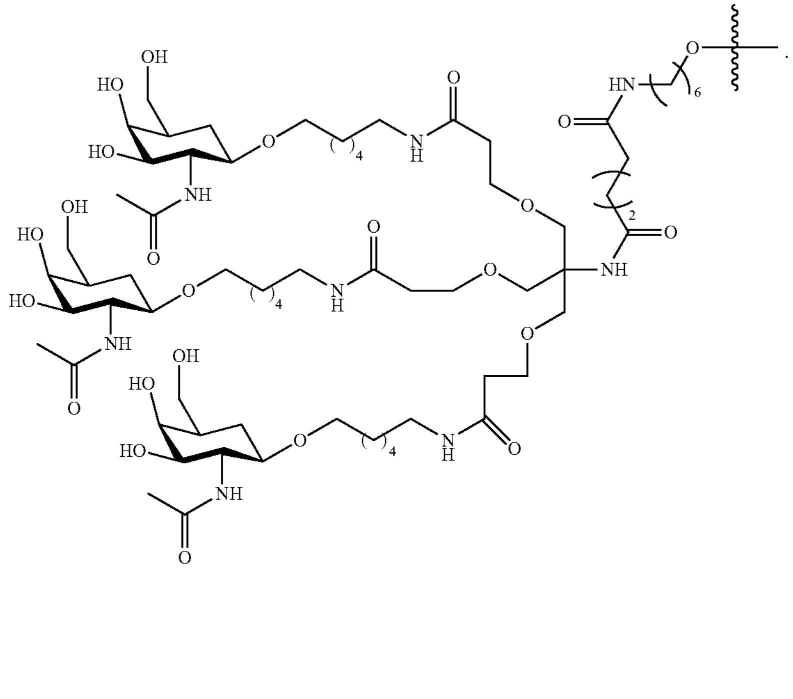

In another embodiment, a carbohydrate conjugate for use in the compositions and methods of the invention is a monosaccharide. In one embodiment, the monosaccharide is an N-acetylgalactosamine, such as Formula II

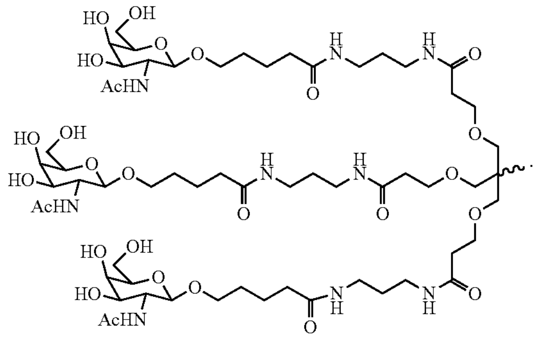

Another representative carbohydrate conjugate for use in the embodiments described herein includes, but is not limited to, (Formula XXXVI)

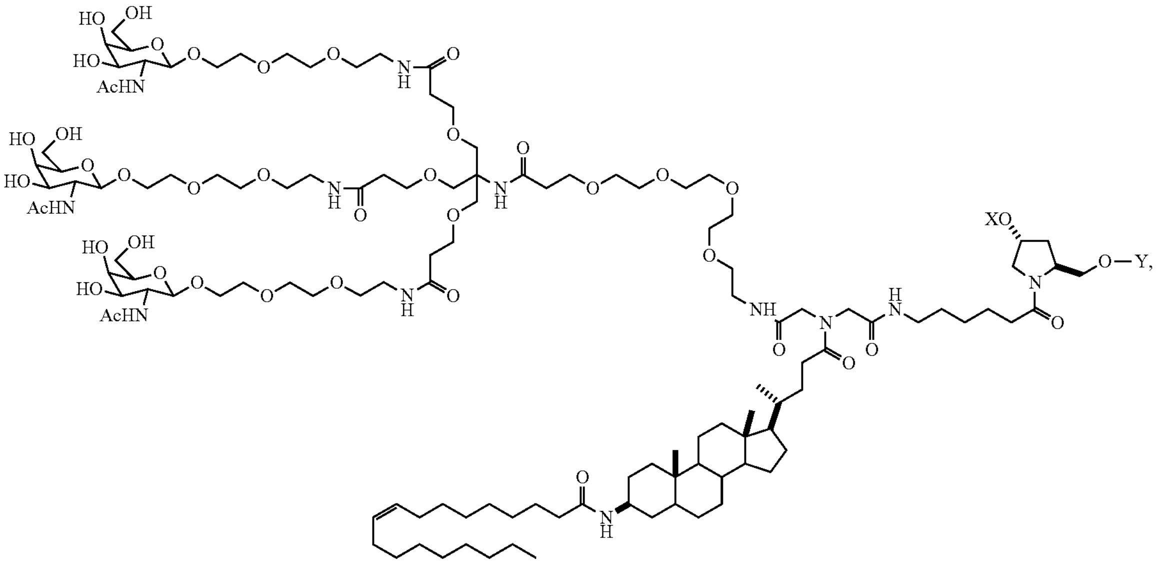

when one of X or Y is an oligonucleotide, the other is a hydrogen.

In certain embodiments of the invention, the GalNAc or GalNAc derivative is attached to an iRNA agent of the invention via a monovalent linker. In some embodiments, the GalNAc or GalNAc derivative is attached to an iRNA agent of the invention via a bivalent linker. In yet other embodiments of the invention, the GalNAc or GalNAc derivative is attached to an iRNA agent of the invention via a trivalent linker.

In one embodiment, the double stranded RNAi agents of the invention comprise one GalNAc or GalNAc derivative attached to the iRNA agent, e.g., the 5'end of the sense strand of a dsRNA agent, or the 5' end of one or both sense strands of a dual targeting RNAi agent as described herein. In another embodiment, the double stranded RNAi agents of the invention comprise a plurality (e.g., 2, 3, 4, 5, or 6) GalNAc or GalNAc derivatives, each independently attached to a plurality of nucleotides of the double stranded RNAi agent through a plurality of monovalent linkers.

In some embodiments, for example, when the two strands of an iRNA agent of the invention are part of one larger molecule connected by an uninterrupted chain of nucleotides between the 3'-end of one strand and the 5'-end of the respective other strand forming a hairpin loop comprising, a plurality of unpaired nucleotides, each unpaired nucleotide within the hairpin loop may independently comprise a GalNAc or GalNAc derivative attached via a monovalent linker.

In some embodiments, the carbohydrate conjugate further comprises one or more additional ligands as described above, such as, but not limited to, a PK modulator or a cell permeation peptide.

Additional carbohydrate conjugates and linkers suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, or substituted or unsubstituted heterocyclic; where R8 is hydrogen, acyl, aliphatic, or substituted aliphatic. In one embodiment, the linker is between about 1-24 atoms, 2-24, 3-24, 4-24, 5-24, 6-24, 6-18, 7-18, 8-18, 7-17, 8-17, 6-16, 7-17, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times, or more, or at least 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

i. Redox Cleavable Linking Groups

In certain embodiments, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In other embodiments, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, and —O—P(S)(H)—S—. A preferred embodiment is —O—P(O)(OH)—O—. These candidates can be evaluated using methods analogous to those described above.

iii. Acid Cleavable Linking Groups

In other embodiments, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In other embodiments, a cleavable linker comprises an ester-based cleavable linking group. An ester-based cleavable linking group is cleaved by enzymes such as esterases and amidases in cells. Examples of ester-based cleavable linking groups include, but are not limited to, esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet other embodiments, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHRAC(O)NHCHRBC(O)—, where RA and RB are the R groups of the two adjacent amino acids. These candidates can be evaluated using methods analogous to those described above.

In some embodiments, an iRNA of the invention is conjugated to a carbohydrate through a linker. Non-limiting examples of iRNA carbohydrate conjugates with linkers of the compositions and methods of the invention include, but are not limited to.

(Formula XXXVII)

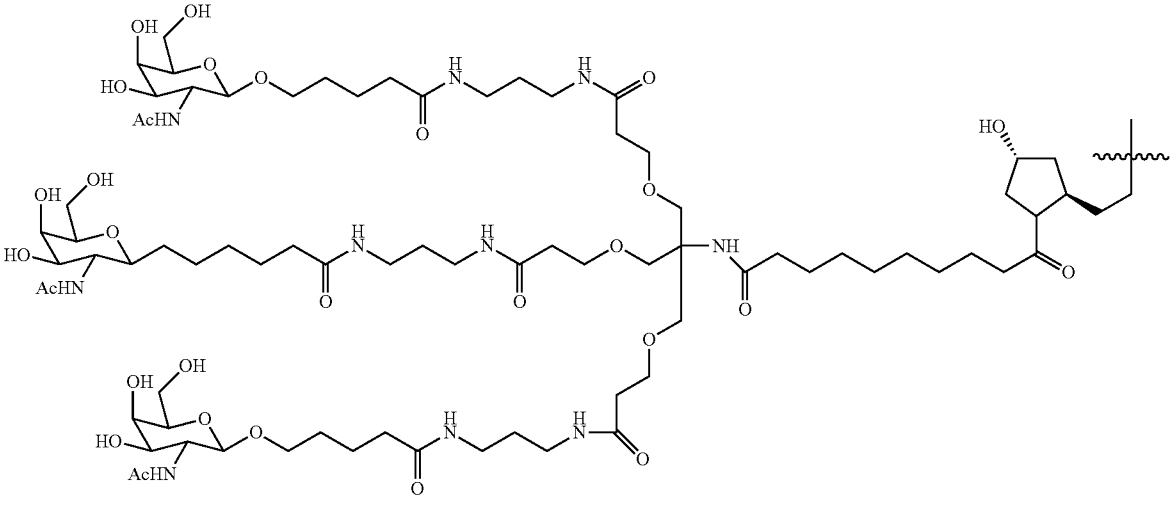

,

-continued
(Formula XXXVIII)
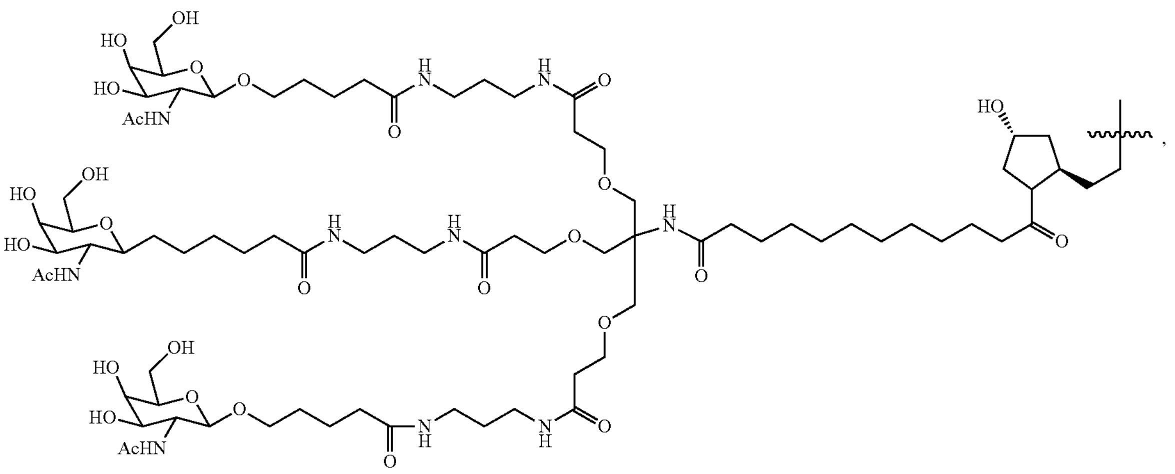
(Formula XXXIX)
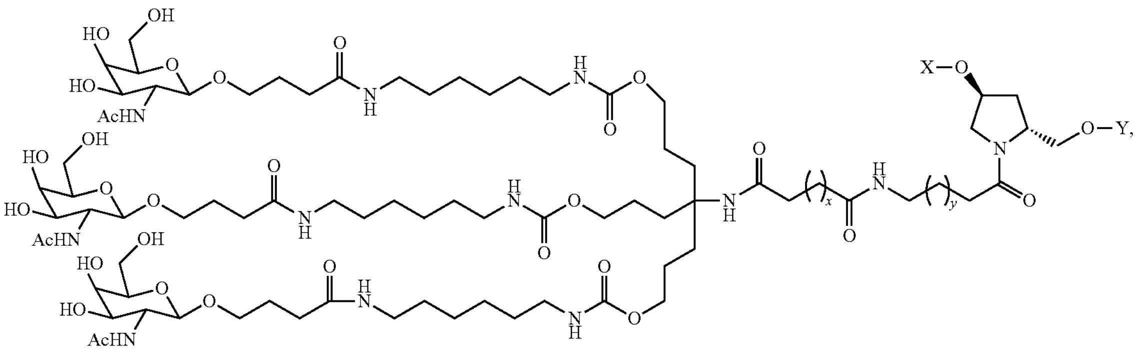
x = 1-30
y = 1-15
(Formula XL)
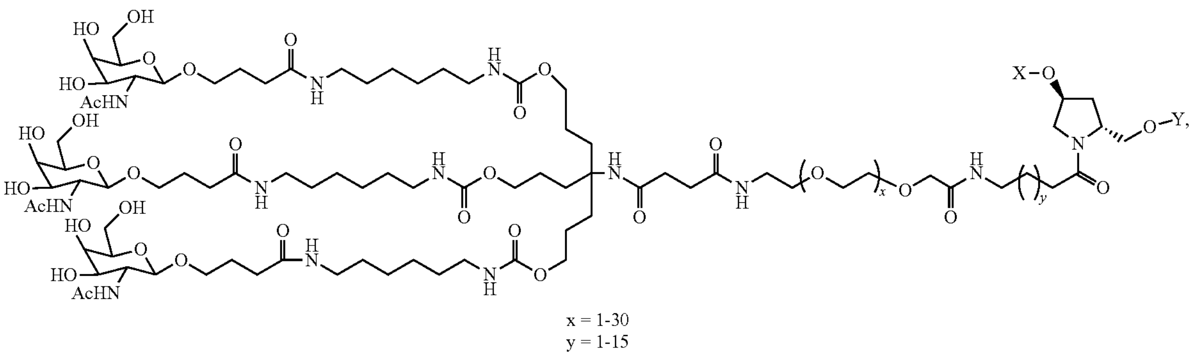
x = 1-30
y = 1-15

-continued
(Formula XLI)
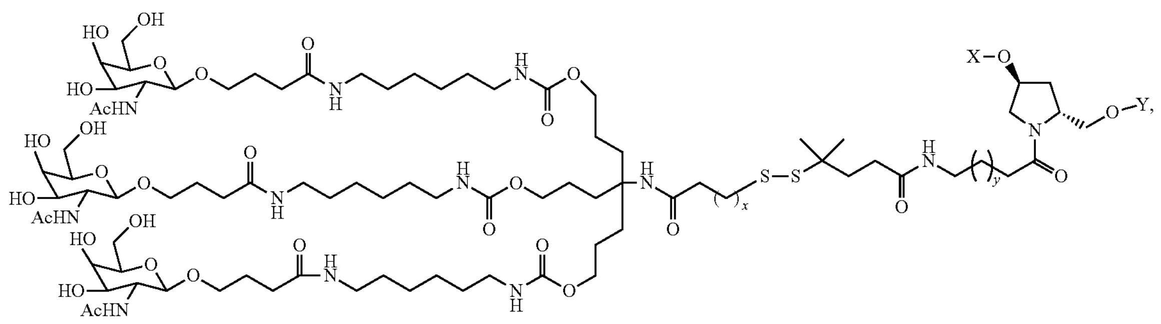
x = 0-30
y = 1-15
(Formula XLII)
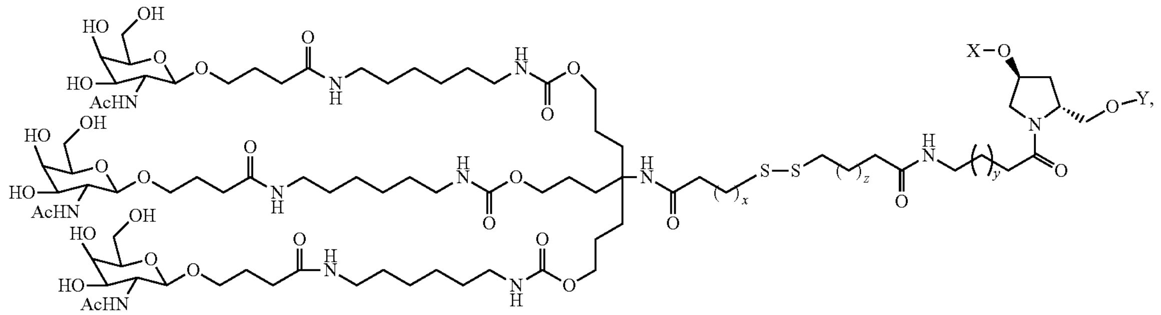
x = 0-30
y = 1-15
z = 1-20
(Formula XLIII)
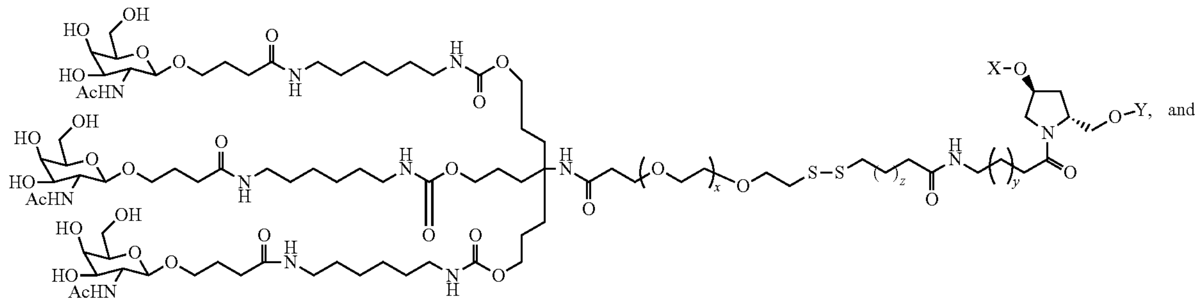
x = 1-30
y = 1=15
z = 1-20
(Formula XLIV)
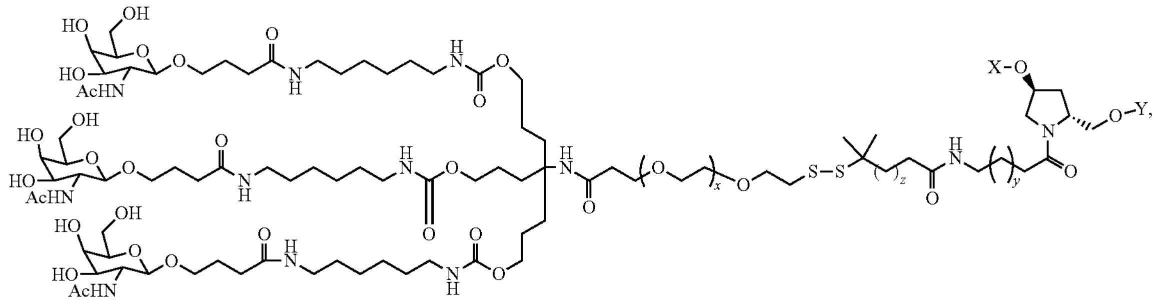
x = 1-30
y = 1=15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XLV)-(XLVI):

Formula XXXXV

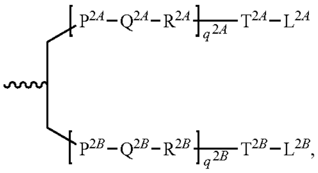

Formula XLVI

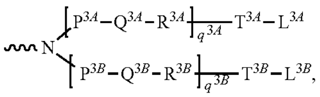

Formula XLVII

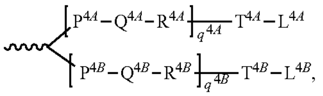

Formula XLVIII

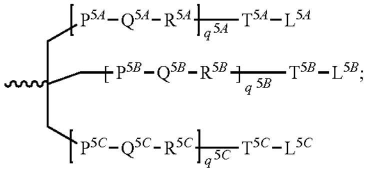

wherein:

q2A, q2B, q3A, q3B, q4A, q4B, q5A, q5B and q5C represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R"), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, $—C(O)—CH(R^a)—NH—$, CO, CH=N—O,

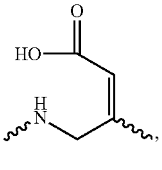,

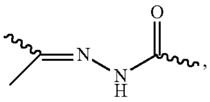,

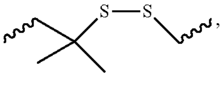,

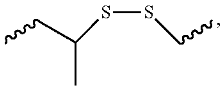,

-continued

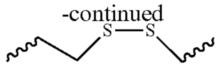

or heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XLIX):

Formula XLIX

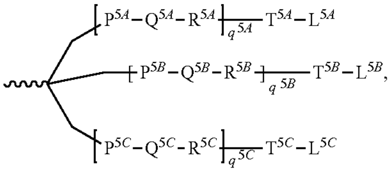

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941; 6,294,664; 6,320,017; 6,576,752; 6,783,931; 6,900,297; 7,037,646; and 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAi agents, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

IV. Delivery of an iRNA of the Invention

The delivery of an iRNA of the invention to a cell e.g., a cell within a subject, such as a human subject can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when a dsRNAi agent is administered locally. For example, intraocular delivery of a VEGF dsRNA by intravitreal injection in cynomolgus monkeys (Tolentino, M J, et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the prevention of an infection, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O, et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H, et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R, et al (2003) *J. Mol. Biol*

327:761-766; Verma, U N, et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N, et al (2003), supra), Oligofectamine, "solid nucleic acid lipid particles" (Zimmermann, T S, et al (2006) *Nature* 441:111-114), cardiolipin (Chien, P Y, et al (2005) *Cancer Gene Ther.* 12:321-328; Pal, A, et al (2005) *Int J. Oncol.* 26:1087-1091), polyethyleneimine (Bonnet Me., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A, et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector encoded iRNAs of the Invention iRNA targeting the Serpina1 gene can be expressed from transcription units inserted into DNA or RNA vectors (see, e.g., Couture, A, et al., *TIG.* (1996), 12:5-10; Skillern, A, et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are known in the art.

V. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a Serpina1 gene, e.g., a Serpina1 deficiency-associated disorder, e.g., a Serpina1 deficiency liver disorder. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions comprising RNAi agents of the invention may be, for example, solutions with or without a buffer, or compositions containing pharmaceutically acceptable carriers. Such compositions include, for example, aqueous or crystalline compositions, liposomal formulations, micellar formulations, emulsions, and gene therapy vectors.

In the methods of the invention, the RNAi agent may be administered in a solution. A free RNAi agent may be administered in an unbuffered solution, e.g., in saline or in water. Alternatively, the free siRNA may also be administered in a suitable buffer solution. The buffer solution may comprise acetate, citrate, prolamine, carbonate, or phosphate, or any combination thereof. In a preferred embodiment, the buffer solution is phosphate buffered saline (PBS). The pH and osmolarity of the buffer solution containing the RNAi agent can be adjusted such that it is suitable for administering to a subject.

In some embodiments, the buffer solution further comprises an agent for controlling the osmolarity of the solution, such that the osmolarity is kept at a desired value, e.g., at the physiologic values of the human plasma. Solutes which can be added to the buffer solution to control the osmolarity include, but are not limited to, proteins, peptides, amino acids, non-metabolized polymers, vitamins, ions, sugars, metabolites, organic acids, lipids, or salts. In some embodiments, the agent for controlling the osmolarity of the solution is a salt. In certain embodiments, the agent for controlling the osmolarity of the solution is sodium chloride or potassium chloride.

The pharmaceutical compositions of the invention may be administered in dosages sufficient to inhibit expression of a Serpina1 gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a liver disorder that would benefit from reduction in the expression of Serpina1. Such models can be used for in vivo testing of iRNA, as well as for determining a therapeutically effective dose. Suitable mouse models are known in the art and include, for example, a mouse containing a transgene expressing human Serpina1.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term “liposome” refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.,* 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release,* 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P.Pharma. Sci.,* 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters,* 1987, 223, 42; Wu et al., *Cancer Research,* 1993, 53, 3765).

Various liposomes comprising one or more glycolipids are known in the art. Papahadjopoulos et al. (*Ann. N.Y. Acad. Sci.,* 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.,* 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L.

et al., *Proc. Natl. Acad. Sci., USA* 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., *Journal of Drug Targeting,* 1992, vol. 2, 405-410 and du Plessis et al., *Antiviral Research,* 18, 1992, 259-265; Mannino, R. J. and Fould-Fogerite, S., *Biotechniques* 6:682-690, 1988; Itani, T. et al. *Gene* 56:267-276. 1987; Nicolau, C. et al. *Meth. Enz.* 149:157-176, 1987; Straubinger, R. M. and Papahadjopoulos, D. *Meth. Enz.* 101:512-527, 1983; Wang, C. Y. and Huang, *L., Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-

Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($C]_8$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

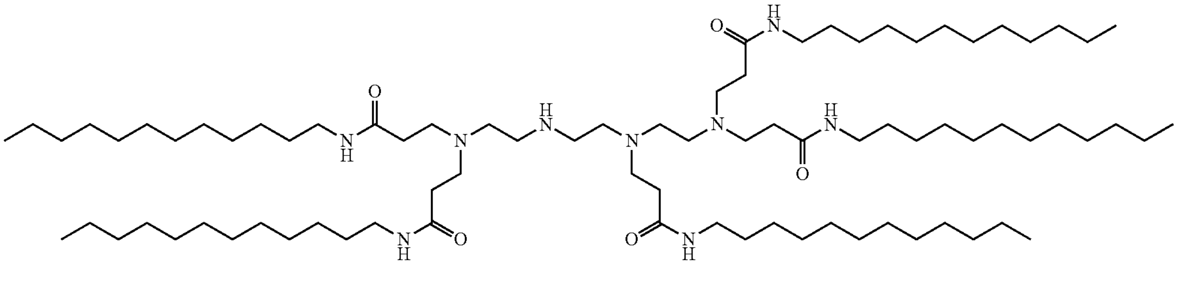

ND98 Isomer I

LNP01 formulations are described, e.g., in International Application Publication No. WO 2008/042973, which is hereby incorporated by reference.

Additional exemplary lipid-dsRNA formulations are described in Table A.

TABLE A

| | Ionizable/Cationic Lipid | cationic lipid/non-cationic lipid/cholesterol/PEG-lipid conjugate Lipid:siRNA ratio |
|---|---|---|
| LNP-1 | l,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylphosphatidylcholine

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

LNP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and antioxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., *Pharmaceutical Research,* 1994, 11, 1385-1390; Ritschel, *Meth. Find. Exp. Clin. Pharmacol.,* 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research,* 1994, 11, 1385; Ho et al., *J. Pharm. Sci.,* 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes has been discussed above.

iii. Microparticles

An RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.,* 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.,* 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.,* 1992, 263, 25; Yamashita et al., *J. Pharm. Sci.,* 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.,* 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.,* 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass' D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a bleeding disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by Serpina1 expression. In any event, the administering physician can adjust the amount and timing of iRNA administration on the basis of results observed using standard measures of efficacy known in the art or described herein.

VI. Methods for Inhibiting Serpina1 Expression

The present invention provides methods of inhibiting expression of a Serpina1 in a cell. The methods include contacting a cell with an RNAi agent, e.g., a double stranded RNAi agent, in an amount effective to inhibit expression of the Serpina1 in the cell, thereby inhibiting expression of the Serpina1 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a $GalNAc_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a Serpina1" is intended to refer to inhibition of expression of any Serpina1 gene (such as, e.g., a mouse Serpina1 gene, a rat Serpina1 gene, a monkey Serpina1 gene, or a human Serpina1 gene) as well as variants or mutants of a Serpina1 gene. Thus, the Serpina1 gene may be a wild-type Serpina1 gene, a mutant Serpina1 gene, or a transgenic Serpina1 gene in the context of a genetically manipulated cell, group of cells, or organism.

"Inhibiting expression of a Serpina1 gene" includes any level of inhibition of a Serpina1 gene, e.g., at least partial suppression of the expression of a Serpina1 gene. The expression of the Serpina1 gene may be assessed based on the level, or the change in the level, of any variable associated with Serpina1 gene expression, e.g., Serpina1 mRNA level, Serpina1 protein level, or lipid levels. This level may be assessed in an individual cell or in a group of cells, including, for example, a sample derived from a subject.

Inhibition may be assessed by a decrease in an absolute or relative level of one or more variables that are associated with Serpina1 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a Serpina1 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

Inhibition of the expression of a Serpina1 gene may be manifested by a reduction of the amount of mRNA expressed by a first cell or group of cells (such cells may be present, for example, in a sample derived from a subject) in which a Serpina1 gene is transcribed and which has or have been treated (e.g., by contacting the cell or cells with an RNAi agent of the invention, or by administering an RNAi agent of the invention to a subject in which the cells are or were present) such that the expression of a Serpina1 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA\text{ in control cells}) - (mRNA\text{ in treated cells})}{(mRNA\text{ in control cells})} \cdot 100\%$$

Alternatively, inhibition of the expression of a Serpina1 gene may be assessed in terms of a reduction of a parameter that is functionally linked to Serpina1 gene expression, e.g., Serpina1 protein expression, such as ALT, alkaline phosphatase, bilirubin, prothrombin and albumin Serpina1 gene silencing may be determined in any cell expressing Serpina1, either constitutively or by genomic engineering, and by any assay known in the art. The liver is the major site of Serpina1 expression. Other significant sites of expression include the lung and intestines.

Inhibition of the expression of a Serpina1 protein may be manifested by a reduction in the level of the Serpina1 protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a Serpina1 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of Serpina1 mRNA that is expressed by a cell or group of cells may be determined using any method known in the art for assessing mRNA expression. In one embodiment, the level of expression of Serpina1 in a sample is determined by detecting a transcribed polynucleotide, or portion thereof, e.g., mRNA of the Serpina1 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of Serpina1 is determined using a nucleic acid probe. The term "probe", as used herein, refers to any molecule that is capable of selectively binding to a specific Serpina1. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to Serpina1 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of Serpina1 mRNA.

An alternative method for determining the level of expression of Serpina1 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of Serpina1 is determined by quantitative fluorogenic RT-PCR (i.e., the TaqMan™ System).

The expression levels of Serpina1 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of Serpina1 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of Serpina1 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the RNAi agent is administered to a subject such that the RNAi agent is delivered to a specific site within the subject. The inhibition of expression of Serpina1 may be assessed using measurements of the level or change in the level of Serpina1 mRNA or Serpina1 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

VII. Methods for Treating or Preventing a Serpina1 Associated Disease

The present invention also provides methods for treating or preventing diseases and conditions that can be modulated by down regulating Serpina1 gene expression. For example, the compositions described herein can be used to treat Serpina1 associated diseases, such as liver diseases, e.g., chronic liver disease, liver inflammation, cirrhosis, liver fibrosis, and/or hepatocellular carcinoma, and other pathological conditions that may be associated with these disorders, such as lung inflammation, emphysema, and COPD.

The present invention also provides methods for inhibiting the development of hepatocellular carcinoma in a subject, e.g., a subject having a Serpina1 deficiency variant. The methods include administering a therapeutically effective amount of a composition of the invention to the subject, thereby inhibiting the development of hepatocellular carcinoma in the subject.

Methods and uses of the compositions of the invention for reducing the accumulation of misfolded Serpina1 in the liver of a subject, e.g., a subject having a Serpina1 deficiency variant, are also provided by the present invention. The methods include administering a therapeutically effective amount of a composition of the invention to the subject, thereby reducing the accumulation of misfolded Serpina1 in the liver of the subject.

As used herein, a "subject" includes a human or non-human animal, preferably a vertebrate, and more preferably a mammal A subject may include a transgenic organism. Most preferably, the subject is a human, such as a human suffering from or predisposed to developing a Serpina1-associated disease. In one embodiment, the subject suffering or predisposed to developing a Serpina1-associated disease has one or more Serpina1 deficient alleles, e.g., a PIZ, PIS, or PIM(Malton) allele.

In further embodiments of the invention, an iRNA agent of the invention is administered in combination with an additional therapeutic agent. The iRNA agent and an additional therapeutic agent can be administered in combination in the same composition, e.g., parenterally, or the additional therapeutic agent can be administered as part of a separate composition or by another method described herein.

Examples of additional therapeutic agents suitable for use in the methods of the invention include those agents known to treat liver disorders, such as liver cirhosis. For example, an iRNA agent featured in the invention can be administered with, e.g., ursodeoxycholic acid (UDCA), immunosuppressive agents, methotrexate, corticosteroids, cyclosporine, colchicine, antipruritic treatments, such as antihistamines, cholestyramine, colestipol, rifampin, dronabinol (Marinol), and plasmaphesesis, prophylactic antibiotics, ultraviolet light, zinc supplements, and hepatitis A, influenza and pneumococci vaccination.

In some embodiments of the methods of the invention, Serpina1 expression is decreased for an extended duration, e.g., at least one week, two weeks, three weeks, or four weeks or longer. For example, in certain instances, expression of the Serpina1 gene is suppressed by at least about 5%, 10%, 15%, 20%, 25%, 30%, 35%, 40%, 45%, 50%, or 55% by administration of an iRNA agent described herein. In some embodiments, the Serpina1 gene is suppressed by at least about 60%, 70%, or 80% by administration of the iRNA agent. In some embodiments, the Serpina1 gene is suppressed by at least about 85%, 90%, or 95% by administration of the iRNA agent.

The iRNA agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof. In preferred embodiments, the iRNA agents are administered subcutaneously.

In some embodiments, the administration is via a depot injection. A depot injection may release the iRNA agents in a consistent way over a prolonged time period. Thus, a depot injection may reduce the frequency of dosing needed to obtain a desired effect, e.g., a desired inhibition of Serpina1, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

The methods of the invention include administering an iRNA agent at a dose sufficient to suppress/decrease levels of Serpina1 mRNA for at least 5, more preferably 7, 10, 14, 21, 25, 30 or 40 days; and optionally, administering a second single dose of the iRNA agent, wherein the second single dose is administered at least 5, more preferably 7, 10, 14, 21, 25, 30 or 40 days after the first single dose is administered, thereby inhibiting the expression of the Serpina1 gene in a subject.

In one embodiment, doses of an iRNA agent of the invention are administered not more than once every four weeks, not more than once every three weeks, not more than once every two weeks, or not more than once every week. In another embodiment, the administrations can be maintained for one, two, three, or six months, or one year or longer.

In general, the iRNA agent does not activate the immune system, e.g., it does not increase cytokine levels, such as TNF-alpha or IFN-alpha levels. For example, when measured by an assay, such as an in vitro PBMC assay, such as described herein, the increase in levels of TNF-alpha or IFN-alpha, is less than 30%, 20%, or 10% of control cells treated with a control iRNA agent, such as an iRNA agent that does not target Serpina1.

For example, a subject can be administered a therapeutic amount of an iRNA agent, such as 0.5 mg/kg, 1.0 mg/kg, 1.5 mg/kg, 2.0 mg/kg, or 2.5 mg/kg dsRNA. The iRNA agent can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer.

After an initial treatment regimen, the treatments can be administered on a less frequent basis. For example, after administration biweekly for three months, administration can be repeated once per month, for six months or a year or longer. Administration of the iRNA agent can reduce Serpina1 levels, e.g., in a cell, tissue, blood, urine, organ (e.g., the liver), or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA agent, patients can be administered a smaller dose, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels. An exemplary smaller dose is one that results in an incidence of infusion reaction of less than or equal to 5%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of liver fibrosis or amelioration of liver fibrosis can be assessed, for example by periodic monitoring of liver fibrosis markers: a-2-macroglobulin (a-MA), transferrin, apolipoproteinA1, hyaluronic acid (HA), laminin, N-terminal procollagen III (PIIINP), 7S collagen IV (7S-IV), total bilirubin, indirect bilirubin, alanine aminotransferase (ALT), aspartate aminotransferase (AST), AST/ALT, g-glutamyl transpeptidase (GGT), alkaline phosphatase (ALP), albumin, albumin/globulin, blood urea nitrogen (BUN), creatinine (Cr), triglyceride, cholersterol, high density lipoprotein and low density lipoprotein and liver puncture biopsy. Liver fibrosis markers can be measured and/or liver puncture biopsy can be performed before treatment (initial readings) and subsequently (later readings) during the treatment regimen.

Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA agent targeting Serpina1 or pharmaceutical composition thereof, "effective against" a Serpina1 associate disease, such as a liver disease, e.g., a hepatic fibrosis condition, indicates that administration of an iRNA agent of the invention in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating liver diseases.

In the methods of the invention, an iRNA agent as described herein can be used to treat individuals having the signs, symptoms and/or markers of, or being diagnosed with, or being a risk of having an Serpina1 associate disease, such as a liver disease, e.g., liver inflammation, cirrhosis, liver fibrosis, and/or hepatoceullar carcinoma. One of skill in the art can easily monitor the signs, symptoms, and/or makers of such disorders in subjects receiving treatment with an iRNA agent as described herein and assay for a reduction in these signs, symptoms and/or makers of at least 10% and preferably to a clinical level representing a low risk of liver disease.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease (such as a liver function described supra), and preferably at least 20%, 30%, 40%, 50% or more can be indicative of effective treatment. Efficacy for a given iRNA agent of the invention or formulation of that iRNA agent can also be judged using an experimental animal model for the given disease as known in the art. When using an experimental animal model, efficacy of treatment is evidenced when a statistically significant reduction in a marker or symptom is observed.

A treatment or preventive effect is also evident when one or more symptoms are reduced or alleviated. For example, a treatment or preventive is effective when one or more of weakness, fatigue, weight loss, nausea, vomiting, abdominal swelling, extremity swelling, excessive itching, and jaundice of the eyes and/or skin is reduced or alleviated.

For certain indications, the efficacy can be measured by an increase in serum levels of Serpina1 protein. As an example, an increase of serum levels of properly folded Serpina1 of at least 10%, at least 20%, at least 50%, at least 100%, at least 200% more can be indicative of effective treatment.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). In this example, prognosis of chronic liver disease, mainly cirrhosis, is measured by an aggregate score of five clinical measures, billirubin, serum albumin, INR, ascites, and hepatic encephalopathy. Each marker is assigned a value from 1-3, and the total value is used to provide a score categorized as A (5-6 points), B (7-9 points), or C (10-15 points), which can be correlated with one and two year survival rates. Methods for determination and analysis of Child-Pugh scores are well known in the art (Farnsworth et al, Am J Surgery 2004 188:580-583; Child and Turcotte. Surgery and portal hypertension. In: The liver and portal hypertension. Edited by CG Child. Philadelphia: Saunders 1964:50-64; Pugh et al, Br J Surg 1973; 60:648-52). Efficacy can be measured in this example by the movement of a patient from e.g., a "B" to an "A." Any positive change resulting in e.g., lessening of severity of disease measured using the appropriate scale, represents adequate treatment using an iRNA or iRNA formulation as described herein.

In one embodiment, the RNAi agent is administered at a dose of between about 0.25 mg/kg to about 50 mg/kg, e.g., between about 0.25 mg/kg to about 0.5 mg/kg, between about 0.25 mg/kg to about 1 mg/kg, between about 0.25 mg/kg to about 5 mg/kg, between about 0.25 mg/kg to about 10 mg/kg, between about 1 mg/kg to about 10 mg/kg, between about 5 mg/kg to about 15 mg/kg, between about 10 mg/kg to about 20 mg/kg, between about 15 mg/kg to about 25 mg/kg, between about 20 mg/kg to about 30 mg/kg, between about 25 mg/kg to about 35 mg/kg, or between about 40 mg/kg to about 50 mg/kg.

The dose of an RNAi agent that is administered to a subject may be tailored to balance the risks and benefits of a particular dose, for example, to achieve a desired level of Serpina1 gene suppression (as assessed, e.g., based on Serpina1 mRNA suppression, Serpina1 protein expression) or a desired therapeutic or prophylactic effect, while at the same time avoiding undesirable side effects.

In some embodiments, the RNAi agent is administered in two or more doses. If desired to facilitate repeated or frequent infusions, implantation of a delivery device, e.g., a pump, semi-permanent stent (e.g., intravenous, intraperitoneal, intracisternal or intracapsular), or reservoir may be advisable. In some embodiments, the number or amount of subsequent doses is dependent on the achievement of a desired effect, e.g., the suppression of a Serpina1 gene, or the achievement of a therapeutic or prophylactic effect, e.g., reducing reducing a symptom of a liver disease. In some embodiments, the RNAi agent is administered according to a schedule. For example, the RNAi agent may be administered once per week, twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, or monthly. In other embodiments, the schedule involves closely spaced administrations followed by a longer period of time during which the agent is not administered. In some embodiments, the RNAi agent is administered in a dosing regimen that includes a "loading phase" of closely spaced administrations that may be followed by a "maintenance phase", in which the RNAi agent is administered at longer spaced intervals.

Any of these schedules may optionally be repeated for one or more iterations. The number of iterations may depend on the achievement of a desired effect, e.g., the suppression of a Serpina1 gene, and/or the achievement of a therapeutic or prophylactic effect, e.g., reducing a symptom of a Serpina1 associated disease, e.g., a liver disease.

In another aspect, the invention features, a method of instructing an end user, e.g., a caregiver or a subject, on how to administer an iRNA agent described herein. The method includes, optionally, providing the end user with one or more doses of the iRNA agent, and instructing the end user to administer the iRNA agent on a regimen described herein, thereby instructing the end user.

Genetic predisposition plays a role in the development of target gene associated diseases, e.g., liver disease. Therefore, a patient in need of a siRNA can be identified by taking a family history, or, for example, screening for one or more genetic markers or variants. Accordingly, in one aspect, the invention provides a method of treating a patient by selecting a patient on the basis that the patient has one or more of a Serpina1 deficiency or a Serpina1 deficiency gene variant, e.g., a PIZ, PIS, or PIM(Malton) allele. The method includes administering to the patient an iRNA agent in a therapeutically effective amount.

A healthcare provider, such as a doctor, nurse, or family member, can take a family history before prescribing or administering an iRNA agent of the invention. In addition, a test may be performed to determine a genotype or phenotype. For example, a DNA test may be performed on a sample from the patient, e.g., a blood sample, to identify the Serpina1 genotype and/or phenotype before a Serpina1 dsRNA is administered to the patient.

VIII. Kits

The present invention also provides kits for using any of the iRNA agents and/or performing any of the methods of the invention. Such kits include one or more RNAi agent(s) and instructions for use, e.g., instructions for inhibiting expression of a Serpina1 in a cell by contacting the cell with the RNAi agent(s) in an amount effective to inhibit expression of the Serpina1. The kits may optionally further comprise means for contacting the cell with the RNAi agent (e.g., an injection device), or means for measuring the inhibition of Serpina1 (e.g., means for measuring the inhibition of Serpina1 mRNA). Such means for measuring the inhibition of Serpina1 may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. Mitigation of Off-Target Effects and In Vivo Toxicity

RNA interference or "RNAi" is a term initially coined by Fire and co-workers to describe the observation that double stranded RNAi (dsRNA) can block gene expression (Fire et al. (1998) *Nature* 391, 806-811; Elbashir et al. (2001) *Genes Dev.* 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double stranded RNA trigger, but the protein components of this activity remained unknown.

One of the off-target effects of siRNA is the miRNA-like effect—the argonaute protein, the core effector in RNA interference, treats siRNA, which is artificially introduced in order to induce RNA interference, as a miRNA (microRNA). (Lam et al. (2015) *Molecular Therapy Nucleic Acids* (2015) 4, e252). The miRNA recognizes a target gene majorly through base-pairing between the seed region (positions 2-7 from the 5' end) and the target mRNA for gene suppression. The off-targets caused by siRNAs originate from base-complementarity of the seed regions of the RISC-loaded antisense strand of siRNA with one or more mRNA. The miRNA-like off-target effects in siRNAs have been reported in several studies, and affect expression of multitude of genes depending on sequences of the seed regions and are serious enough to cause up to 30% of the positive hits in siRNA based phenotype screening. Additionally, in the case of miRNAs, they are also reported to silence target genes through compensatory pairings within their 3' end regions (3'-compensatory pairing) when the interactions between seed region and targets become weak, implicating that the miRNA-like off-target effects are likely to be mediated by such mechanism.

As described below, it has been discovered that dsRNA agents where the antisense strand comprises at least one thermally destabilizing modification of the duplex within the seed region (i.e., at position 2-9 of the 5'-end of the antisense strand, counting from the 5'-end) and/or the dsRNA agent has a melting temperature in the range of from about 40° C. to about 80° C. can be more effective in mediating RNA interference than a parent dsRNA agent lacking the destabilizing modification. Such agents are advantageous for inhibition of target gene expression, while having reduced off-target gene silencing effects, as well as RNAi compositions suitable for therapeutic use.

Materials and Methods

The following materials and methods were used in the Examples.

siRNA Design

Lead development candidate dsRNA agents targeting serine peptidase inhibitor, clade A, member 1 (Serpina1) (AAT) were selected for evaluation in the experiments described herein. dsRNA agents targeting Serpina1 having the modified nucleotide sequence of the parent lead development candidate and having an antisense strand comprising at least one thermally destabilizing modification of the duplex within the seed region (i.e., at position 2-9 of the 5'-end of the antisense strand, counting from the 5'-end) and/or having a melting temperature in the range of from about 40° C. to about 80° C. were designed, synthesized and evaluated as described below.

Specifically, as described in U.S. Provisional Application No. 61/826,125, filed on May 22, 2013, U.S. Provisional Application No. 61/898,695, filed on Nov. 1, 2013; U.S. Provisional Application No. 61/979,727, filed on Apr. 15, 2014; U.S. Provisional Application No. 61/989,028, filed on May 6, 2014; U.S. patent application Ser. No. 14/284,745, now issued as U.S. Pat. No. 9,574,192, issued on Feb. 21, 2017; U.S. patent application Ser. No. 15/399,820, filed on Jan. 6, 2017; and International Patent Application No. PCT/US2014/039109, filed on May 22, 2014, AD-61444 was identified and shown to effectively and durably inhibit AAT in vitro and in vivo. The unmodified sense strand nucleotide sequence of AD-61444 is 5'-CUUC-UUAAUGAUUGAACAAAA-3' (SEQ ID NO: 417) and the unmodified nucleotide sequence of AD-61444 is 5'-UUUU-GUUCAAUCAUUAAGAAGAC-3' (SEQ ID NO: 419). The modified sense strand nucleotide sequence of AD-61444 is 5'-csusucuuaauGfAfuugaacaaaaL96-3' (SEQ ID NO: 418) and the modified antisense strand nucleotide sequence of AD-61444 is 5'-usUfsuUfgUfuCfaAfucaUfuAfaGfaAf-gsasc-3' (SEQ ID NO: 420).

TABLE B

Table 1: Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| Y44 | inverted abasic DNA (2-hydroxymethyl-tetrahydrofurane-5-phosphate) |
| (Agn) | Adenosine-glycol nucleic acid (GNA) |
| (Cgn) | Cytidine-glycol nucleic acid (GNA) |
| (Ggn) | Guanosine-glycol nucleic acid (GNA) |
| (Tgn) | Thymidine-glycol nucleic acid (GNA) S-Isomer |
| P | Phosphate |
| VP | Vinyl-phosphate |
| (Aam) | 2'-O-(N-methylacetamide)adenosine-3'-phosphate |
| (Aams) | 2'-O-(N-methylacetamide)adenosine-3'-phosphorothioate |
| (Tam) | 2'-O-(N-methylacetamide)thymidine-3'-phosphate |
| (Tams) | 2'-O-(N-methylacetamide)thymidine-3'-phosphorothioate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine-3'-phosphate |
| dTs | 2'-deoxythymidine-3'-phosphorothioate |
| dU | 2'-deoxyuridine |
| dUs | 2'-deoxyuridine-3'-phosphorothioate |

Synthesis and Purification

All oligonucleotides were prepared on a MerMade 192 synthesizer on a 1 µmole scale using universal or custom supports. All phosphoramidites were used at a concentration 100 mM in 100% Acetonitrile or 9:1 Acetonitrile:DMF with a standard protocol for 2-cyanoethyl phosphoramidites, except that the coupling time was extended to 400 seconds. Oxidation of the newly formed linkages was achieved using a solution of 50 mM $I_2$ in 9:1 Acetonitrile:Water to create phosphate linkages and 100 mM DDTT in 9:1 Pyridine: Acetonitrile to create phosphorothioate linkages. After the trityl-off synthesis, columns were incubated with 150 µL of 40% aqueous Methylamine for 45 minutes and the solution drained via vacuum into a 96-well plate. After repeating the incubation and draining with a fresh portion of aqueous Methylamine, the plate containing crude oligonucleotide solution was sealed and shaken at room temperature for an additional 60 minutes to completely remove all protecting groups. of the crude oligonucleotides was accomplished via the addition of 1.2 mL of 9:1 Acetonitrile:EtOH to each well followed by incubation at −20° C. overnight. The plate was then centrifuged at 3000 RPM for 45 minutes, the supernatant removed from each well, and the pellets resuspended in 950 µL of 20 mM aqueous NaOAc. Each crude solution was finally desalted over a GE Hi-Trap Desalting Column (Sephadex G25 Superfine) using water to elute the final oligonucleotide products. All identities and purities were confirmed using ESI-MS and IEX HPLC, respectively.

Temperature-Dependent UV Spectroscopy

The melting studies were performed at a duplex concentration of 1 µM (consisting of the modified antisense strand paired with the complementary unmodified RNA sense strand) in 0.33×PBS (3.3 mM Na/K phosphate buffer, pH 7.4, with 46 mM NaCl and 0.9 mM KCl) in 1 cm path length quartz cells on a Beckman DU800 spectrophotometer equipped with a thermoprogrammer Each cuvette contained 200 µL of sample solution covered by 125 µL of light mineral oil. Melting curves were monitored at 260 nm with a heating rate of 1° C./min from 15-90° C. Melting temperatures (Tm) were calculated from the first derivatives of the smoothed heating curves and the reported values are the result of at least two independent measurements.

In Vitro Reporter Assays

COS-7 cells were cultured at 37° C., 5% CO2 in Dulbecco's Modified Eagle Medium (DMEM) supplemented with 10% fetal bovine serum (FBS). Cells were co-transfected in 96-well plates (15,000 cells/well) with 10 ng luciferase reporter plasmid and 50 fM to 50 nM siRNA in 10-fold dilutions using 2 µg/mL Lipofectamine 2000 (Thermo Fisher Scientific) according to manufacturer's instructions. Cells were harvested at 48 h after transfection for the dual luciferase assay (Promega) according to manufacturer's instructions. The on-target reporter plasmid contained a single perfectly-complementary site to the antisense strand in the 3' untranslated (3' UTR) of *Renilla* luciferase. The off-target reporter plasmid contained four tandem seed-complementary sites separated by 21-28 nucleotides in the 3' UTR of *Renilla* luciferase. Both plasmids co-expressed Firefly luciferase as a transfection control.

Gene Expression Analysis

Cryopreserved rat and human hepatocytes (Bioreclamation) were cultured at 37° C., 5% CO2 in InVitroGRO CP Medium with Torpedo Antibiotic Mix. Cells were transfected in 96-well plates (20,000 cells/well) with 10 nM siRNA using 2 µg/mL Lipofectamine RNAiMAX (Thermo Fisher Scientific) according to manufacturer's instructions. Cells were harvested at 24 h after transfection for RNA extraction with the miRNeasy Kit (Qiagen) according to manufacturer's instructions. cDNA libraries were prepared using the TruSeq Stranded Total RNA Library Prep Kit (Illumina) and sequenced on NextSeq 500 (Illumina).

In Vivo Mouse and Rat Studies

All studies were conducted using protocols consistent with local, state and federal regulations as applicable and approved by the Institutional Animal Care and Use Committees (IACUCs) at Alnylam Pharmaceuticals.

In mouse pharmacodynamic studies, female C57BL/6 mice (Charles River Laboratories) were administered a single dose of a vehicle control (0.9% sodium chloride, saline) or 0.5 or 1 mg/kg siRNA subcutaneously in the upper back. On Day 8, livers were collected, rinsed in cold saline, immediately snap frozen in liquid nitrogen, and stored at −80 C for mRNA and siRNA analysis.

In rat toxicity studies, male Sprague Dawley rats (Charles River Laboratories) were administered three repeat weekly doses (qw×3) of a vehicle control (0.9% sodium chloride, saline) or 30 mg/kg siRNA subcutaneously in the upper back. On Day 16, serum was collected for clinical pathology evaluation, and livers were collected for histopathology evaluation and for mRNA and siRNA analysis.

mRNA and siRNA Quantitation

RNA was extracted with the miRNeasy Kit (Qiagen) according to manufacturer's instructions, converted to cDNA with the High-Capacity cDNA Reverse Transcription Kit (Thermo Fisher Scientific) according to manufacturer's instructions, and mRNA levels were assessed by quantitative polymerase chain reaction (qPCR) using gene-specific Taqman probes (Thermo Fisher Scientific) on Roche Light Cycler 480 II using LightCycler 480 Probes Master (Roche).

To quantitate exposure to siRNAs, cell pellets were resuspended in phosphate-buffer saline (PBS) containing 0.25% Triton X-100, heated at 95° C. for 10 min, centrifuged at 14,000 rpm at 4° C. for 10 min, and reverse transcription was performed on the supernatants using TaqMan MicroRNA Reverse Transcription Kit (Thermo Fisher Scientific) according to the manufacturer's instructions. qPCR was performed on Roche Light Cycler 480 II using LightCycler 480 Probes Master (Roche) according to the manufacturer's instructions.

Results

1. In Vitro Studies

Results of in vitro reporter assay are summarized in Table 1. As the data in Table 1 show, glycolic nucleic acid (GNA) modification at position 7 of the antisense strand preserves the on-target activity while mitigating the off-target activity in vitro.

TABLE 1

In vitro reporter assays data for GNA modification at position 7 of anti-sense strands

| | | On-target $IC_{50}$ (nM) | Off-target $IC_{50}$ (nM) |
|---|---|---|---|
| AAT | Parent | 0.013 | 0.97 |
| | (S)-GNA at AS pos. 7 | 0.013 | >500 |

Luciferase reporter plasmids were co-transfected with siRNAs into COS-7 cells and the luciferase assay was performed at 48 h.

2. Gene Expression Analysis

Results of in vitro gene expression analysis are summarized in Table 2. As seen from Table 2, GNA modification at position 7 of the antisense strand mitigated off-target activity in vitro.

TABLE 2

Gene expression analysis

| | | Number of downregulated genes ($p < 0.05$) | Number of upregulated genes ($p < 0.05$) |
|---|---|---|---|
| AAT | Parent | 100 | 11 |
| | (S)-GNA at AS pos. 7 | 1 | 2 |

Human hepatocytes (AAT) were transfected with siRNAs and RNA was collected at 24 h for RNA sequencing.

3. In Vivo Mouse Studies

Results of in vivo studies are summarized in Table 3. As seen, GNA modification at position 7 of the antisense strand preserves potency in vivo (Table 3).

TABLE 3

Mouse pharmacodynamics data

| | | % mRNA remaining at Day 8 |
|---|---|---|
| AAT | Parent | 30 |
| | (S)-GNA at AS pos. 7 | 29 |

Mice were administered a single dose of siRNAs targeting AAT at 1 mg/kg and liver mRNA knockdown was assessed at Day 8.

Example 2. In Vivo and In Vitro Analysis of dsRNA Agents Targeting Serpina1

To further evaluate the in vivo effect of incorporating a GNA nucleotide in AD-61444, AD-61444 was further modified with a GNA nucleotide at antisense position 6 (AD-75994) or 7 (AD-75995) (FIG. 1A) and mice transgenic for human AAT were subcutaneously administered a single1 mg/kg dose of the agent. Prior to dosing, and at the timepoints indicated in FIG. 1B, serum was obtained for quantification of circulating AAT. AAT protein levels were determined by sandwich ELISA, and the data was normalized to the baseline value of AAT protein levels.

As depicted in FIG. 1B, incorporation of a GNA nucleotide at either position 6 or 7 of the antisense strand of AD-61444 resulted in a loss of activity as compared to the parent molecule.

Accordingly, the total number of 2'-fluoro modified nucleotides in AD-61444 was reduced resulting in AD-77407, and a GNA nucleotide was incorporated at antisense position 7 of AD-77407 resulting in AD-77412 (FIG. 1C). Mice transgenic for human AAT were subcutaneously administered a single 1 mg/kg dose of the agent. Prior to dosing, and at the timepoints indicated in FIG. 1D, serum was obtained for quantification of circulating AAT. AAT protein levels were determined by sandwich ELISA, and the data was normalized to the baseline value of AAT protein levels.

FIG. 1D demonstrates that reducing the 2'flouro content of AD-61444 (i.e., AD-77407) resulted in a marked improvement in activity in the mice. Moreover, incorporation of a GNA nucleotide in this context (AD-77412) resulted in a net improvement relative to the parent molecule, AD-61444.

Figure 2B:
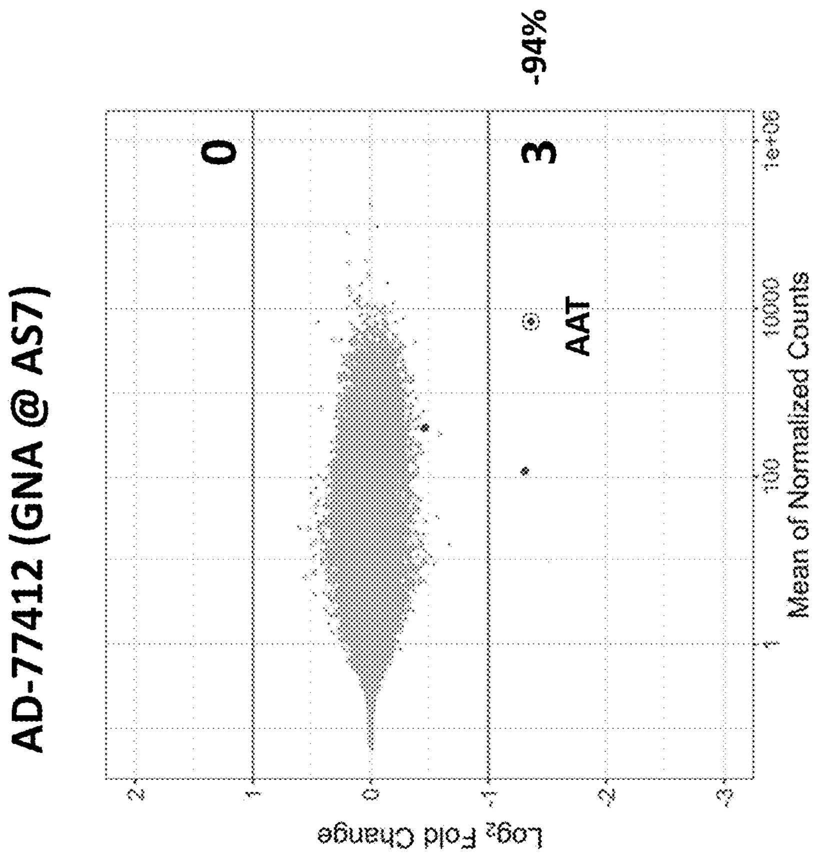
FIG. 2B is a graph depicting the off-target effect of AD-77412 in Hep3B cells transfected with 10 nM of the dsRNA agent 16 hours after treatment.
Figure 2A:
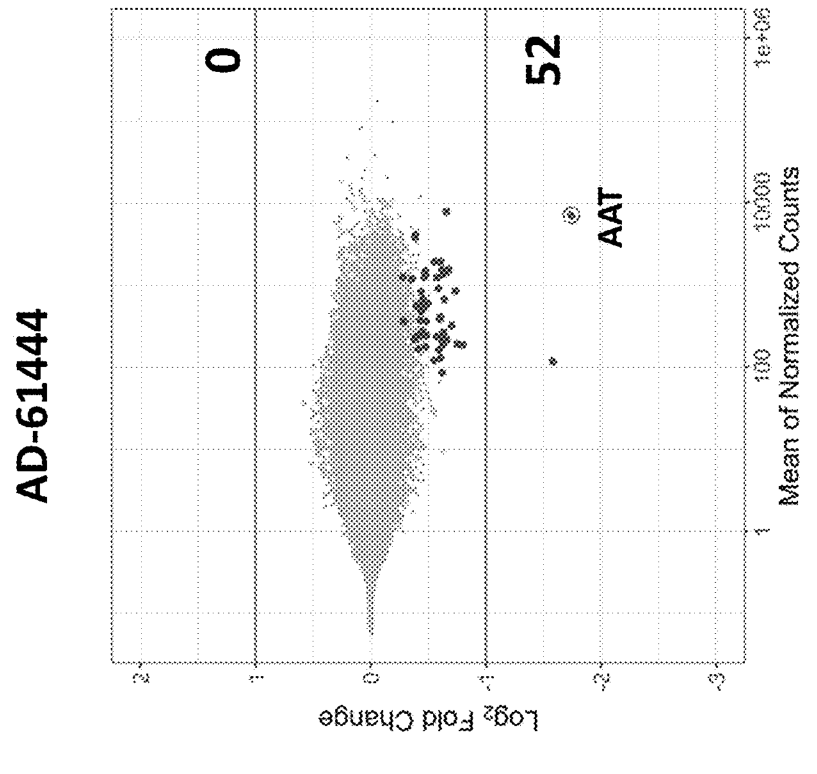
FIG. 2A is a graph depicting the off-target effect of AD-61444 in Hep3B cells transfected with 10 nM of the dsRNA agent 16 hours after treatment.
Figure 3A:
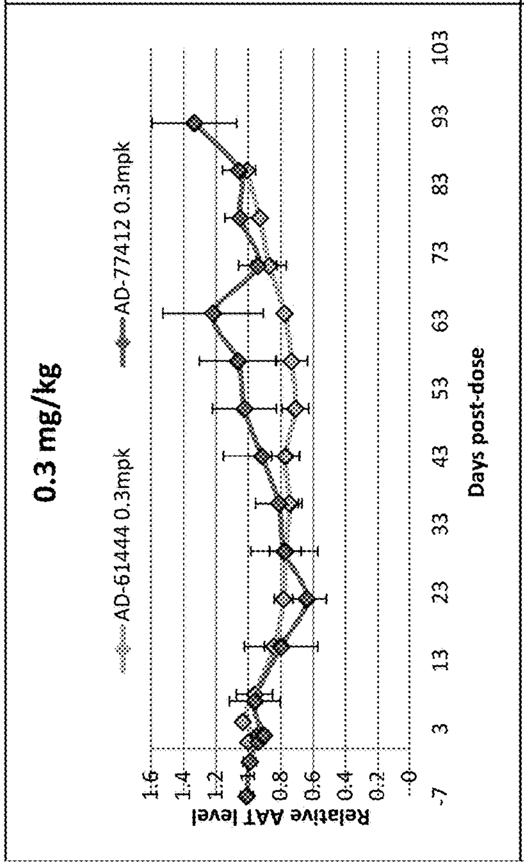
FIG. 3A is a graph depicting the efficacy and durability of AAT silencing in nonhuman primates (NHP) administered a single 0.3 mg/kg dose of the indicated agents. The level of expression of AAT shown is relative to the pre-bleed level of expression of AAT determined at days −7 and −1 pre-dose.
Figure 3B:
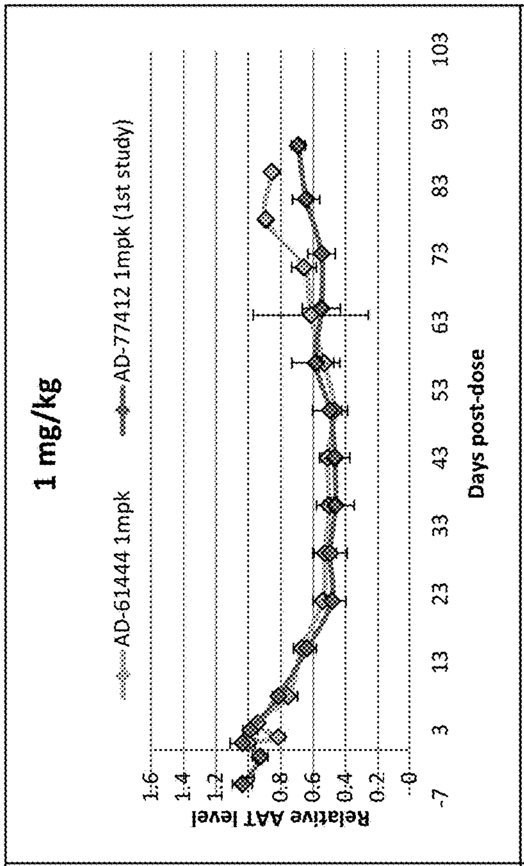
FIG. 3B is a graph depicting the durability of AAT silencing in nonhuman primates administered a single 1 mg/kg dose of the indicated agents. The level of expression of AAT shown is relative to the pre-bleed level of expression of AAT determined at days −7 and −1 pre-dose.
Figure 3C:
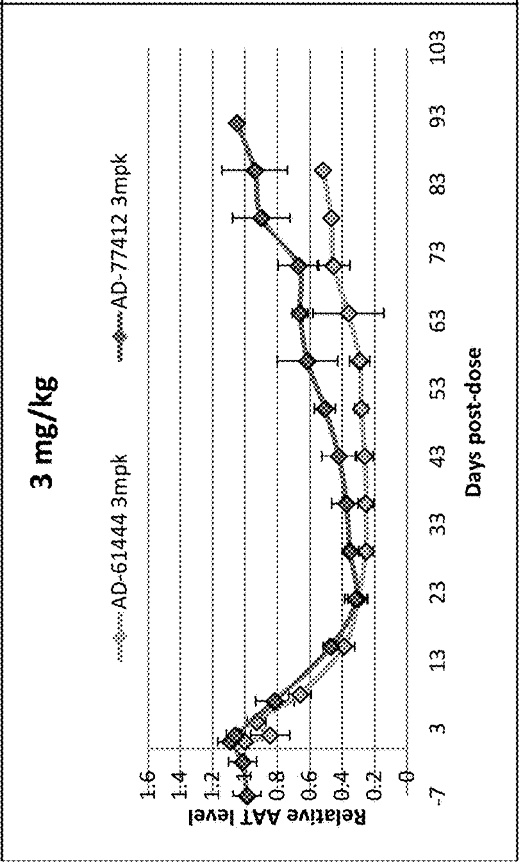
FIG. 3C is a graph depicting the durability of AAT silencing in nonhuman primates administered a single 3 mg/kg dose of the indicated agents. The level of expression of AAT shown is relative to the pre-bleed level of expression of AAT determined at days −7 and −1 pre-dose.
Figure 3D:
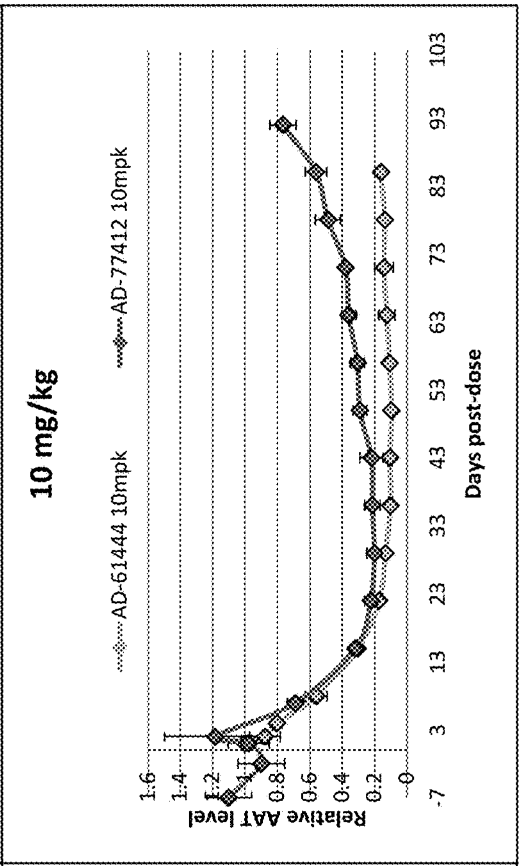
FIG. 3D is a graph depicting the durability of AAT silencing in nonhuman primates administered a single 10 mg/kg dose of the indicated agents. The level of expression of AAT shown is relative to the pre-bleed level of expression of AAT determined at days −7 and −1 pre-dose.

To determine the effect of reducing the 2'-fluoro content of AD-61444 and incorporation of a GNA nucleotide at position 7 of the antisense strand on off-target effects, Hep3b cells were transfected with 10 nM of AD-61444 or AD-77412 using Lipofectamine RNAiMax. After 16 hours, cells were lysed and prepared for transcriptional profiling. As depicted in FIGS. 2A and 2B, the resulting data was graphed showing transcripts whose expression was statistically significantly different relative to mock treated cells as black circles and transcripts whose expression was not statistically significantly different relative to mock treated cells as gray circles. The AAT transcript is indicated and highlighted with a circle.

The data depicted in FIGS. 2A and 2B demonstrate that treatment of cells with AD-61444 resulted in downregulation of fifty-two transcripts, including AAT. By comparison, the GNA-containing duplex, AD-77412, resulted in the downregulated transcripts of only three transcripts, including AAT. Thus, incorporation of a GNA nucleotide substantially reduced the number of observed off-targets downregulated by AD-61444 in vitro.

The effect of AD-77412 was also evaluated in non-human primates. Cynomolgus monkeys were subcutaeoulsy administered a single 0.3 mg/kg, 1.0 mg/kg, 3 mg/kg, or 10 mg/kg dose of either AD-61444 or AD-77412. Prior to dosing, and at the timepoints indicated in FIGS. 3A-3D, serum was obtained for quantification of circulating AAT. AAT protein levels were determined by sandwich ELISA, and the data was normalized to the baseline value of AAT protein levels.

As depicted in FIGS. 3A-3D, all doses of AD-61444 and AD-77412 effectively silenced AAT expression with similar maximum levels of silencing.

In summary, these assays demonstrate that incorporation of a GNA nucleotide into the antisense seed region of the parent molecule, AD-61444, does not result in loss of activity as compared to the parent molecule and significantly reduces off-target effects.

We claim:

1. A double stranded RNA (dsRNA) agent that inhibits expression of a serine peptidase inhibitor, clade A, member 1 (Serpina1) gene, comprising a sense strand and an antisense strand forming a double stranded region, wherein the sense strand comprises at least 19 contiguous nucleotides differing by no more than 3 nucleotides from the nucleotide sequence of 5'-CUUCUUAAUGAUUGAACAAAA-3' (SEQ ID NO: 417), and the antisense strand comprises at least 19 contiguous nucleotides differing by no more than 3 nucleotides from the nucleotide sequence of 5'-UUUUGUUCAAUCAUUAAGAAGAC-3' (SEQ ID NO: 419), wherein substantially all of the nucleotides of the antisense strand comprise a nucleotide modification, wherein the antisense strand comprises at least one thermally destabilizing modification selected from the group consisting of an abasic modification, a mismatch with the opposing nucleotide in the opposing strand, a 2'-deoxy modification, and an acyclic nucleotide modification, at position 4, 5, 6, 7 and/or 8 from the 5'-end, wherein the nucleotides at positions 2, 6, 8, 9, 14, and 16, or at positions 2, 6, 14, and 16, or at positions 2, 14, and 16 from the 5'-end of the antisense strand are 2'-F modified nucleotides, wherein substantially all of the nucleotides of the sense strand comprise a nucleotide modification, wherein the nucleotides at positions 7, 9, 10, and 11, or at positions 7, 10, and 11 from the 5'-end of the sense strand are 2'-F modified nucleotides, wherein the sense strand comprises an ASGPR ligand, wherein each of the sense strand and the antisense strand are independently 19 to 25 nucleotides in length.

2. The dsRNA agent of claim 1, wherein the thermally destabilizing modification is selected from the group consisting of

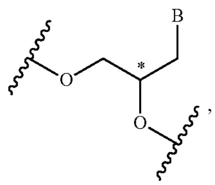
,
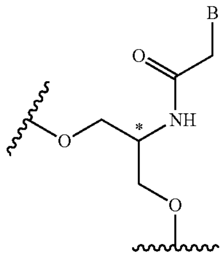
,

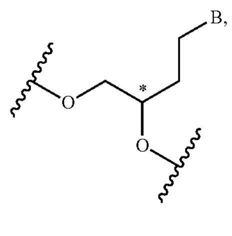

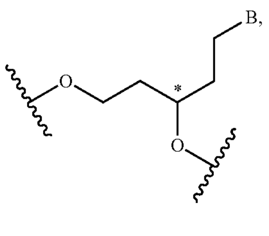

-continued

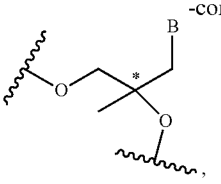
, and
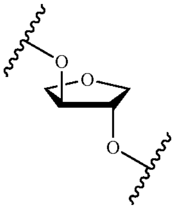
, wherein B is nucleobase.

3. The dsRNA agent of claim 1, wherein the ASGPR ligand is one or more GalNAc derivatives attached through a bivalent or trivalent branched linker.

4. A double stranded RNA (dsRNA) agent that inhibits expression of a serine peptidase inhibitor, clade A, member 1 (Serpina1) target gene sequence, comprising a sense strand and an antisense strand forming a double stranded region, wherein the antisense strand comprises at least 19 contiguous nucleotides differing by no more than 3 nucleotides from the nucleotide sequence of 5'-UUUUGUUCAAUCAUUAAGAAGAC-3' (SEQ ID NO: 419), wherein substantially all of the nucleotides of the antisense strand comprise a nucleotide modification, wherein the antisense strand comprises at least one thermally destabilizing modification selected from the group consisting of an abasic modification, a mismatch with the opposing nucleotide in the opposing strand, a 2'-deoxy modification, and an acyclic nucleotide modification at position 4, 5, 6, 7 and/or 8 from the 5'-end, wherein the nucleotides at positions 2, 6, 8, 9, 14, and 16, or at positions 2, 6, 14, and 16, or at positions 2, 14, and 16 from the 5'-end of the antisense strand are 2'-F modified nucleotides, wherein substantially all of the nucleotides of the sense strand comprise a nucleotide modification, wherein the nucleotides at positions 7, 9, 10, and 11, or at positions 7, 10, and 11 from the 5'-end of the sense strand are 2'-F modified nucleotides, wherein the sense strand comprises an ASGPR ligand, and wherein each of the sense strand and the antisense strand are independently 19 to 25 nucleotides in length.

5. The dsRNA agent of claim 4, wherein the ASGPR ligand is one or more GalNAc derivatives attached through a bivalent or trivalent branched linker.

6. The dsRNA agent of claim 4, wherein the antisense strand comprises the nucleotide sequence 5'-UUUUGUUCAAUCAUUAAGAAGAC-3' (SEQ ID NO: 419).

7. An isolated cell containing the dsRNA agent of claim 1 or 4.

8. A pharmaceutical composition comprising the dsRNA agent of claim 1 or 4.

9. The dsRNA agent of claim 1 or 4, wherein the destabilizing modification is located in position 7 of the antisense strand.

10. The dsRNA of claim 1 or 4, wherein all of the nucleotides of the sense strand and all of the nucleotides of the antisense strand are modified nucleotides.

11. The dsRNA agent of claim 1 or 4, wherein the ASGPR ligand is:

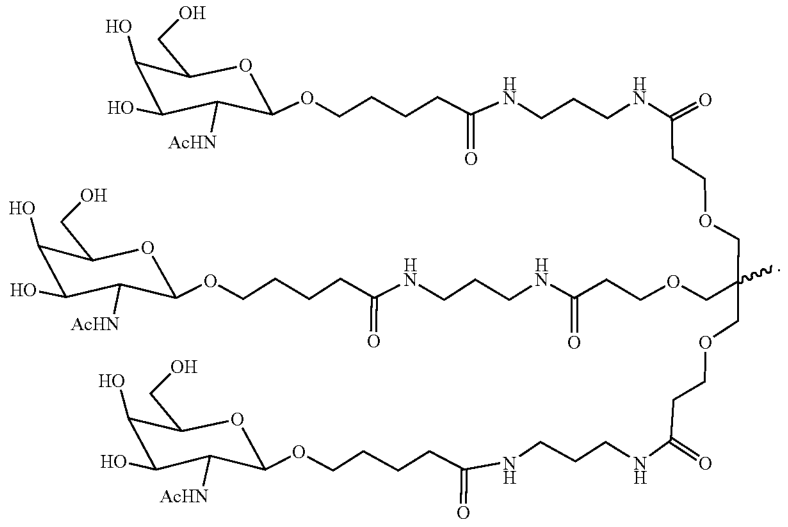 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
12. The dsRNA agent of claim 11, wherein the dsRNA agent is conjugated to the ligand as shown in the following schematic
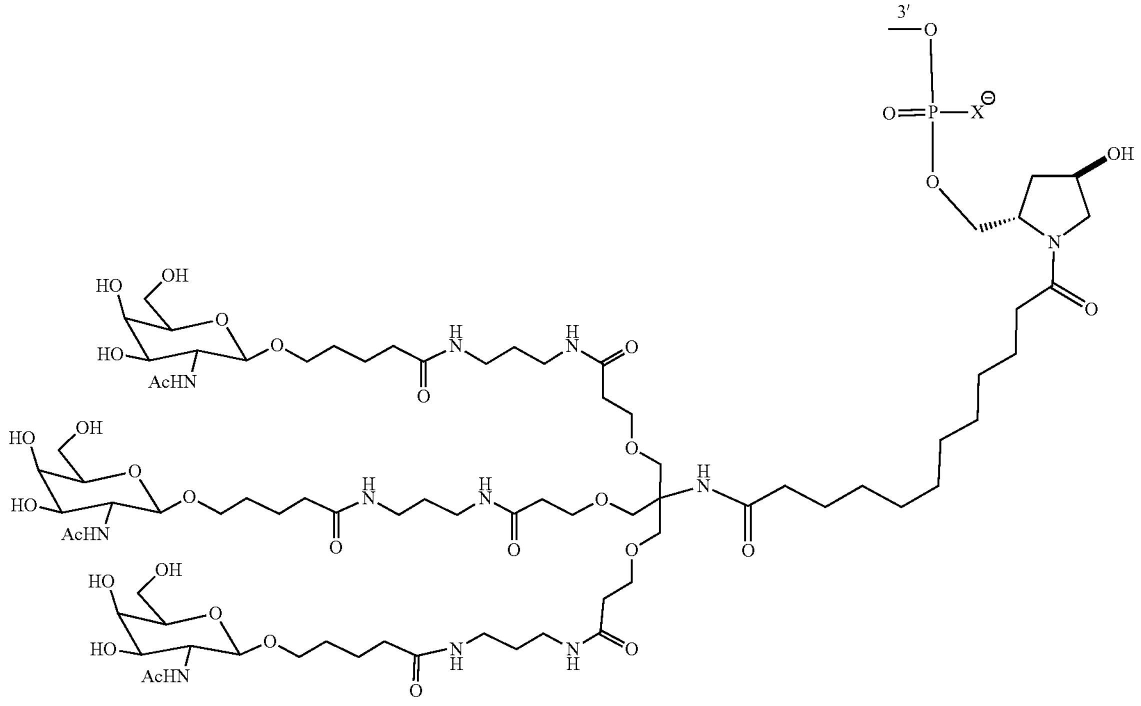
wherein X is O or S.

13. A double stranded RNA (dsRNA) agent that inhibits expression of a serine peptidase inhibitor, clade A, member 1 (Serpina1) target gene sequence, comprising a sense strand and an antisense strand forming a double stranded region, wherein the sense strand comprises at least 19 contiguous nucleotides differing by no more than 3 nucleotides from the nucleotide sequence of 5'-CUUCUUAAUGAUUGAACAAAA-3' (SEQ ID NO: 417), and the antisense strand comprises at least 19 contiguous nucleotides differing by no more than 3 nucleotides from the nucleotide sequence of 5'-UUUUGUUCAAUCAUUAAGAAGAC-3' (SEQ ID NO: 419), wherein all of the nucleotides of the antisense strand comprise a nucleotide modification selected from the group consisting of a thermally destabilizing modification, a 2'-F modification and a 2'-OMe modification, wherein the thermally destabilizing modification is located in position 4 to 8 from the 5'-end of the antisense strand and is selected from the group consisting of an abasic modification, a mismatch with the opposing nucleotide in the opposing strand, a 2'-deoxy modification, and an acyclic nucleotide modification, wherein the nucleotides at positions 2, 6, 8, 9, 14, and 16, or at positions 2, 6, 14, and 16, or at positions 2, 14, and 16 from the 5'-end of the antisense strand are 2'-F modified nucleotides, wherein all of the nucleotides of the sense strand comprise a nucleotide modification, wherein the nucleotides at positions 7, 9, 10, and 11, or at positions 7, 10, and 11 from the 5'-end of the sense strand are 2'-F modified nucleotides, wherein each of the sense strand and the antisense strand are independently 19 to 25 nucleotides in length, and wherein the dsRNA agent has a melting temperature of from about 40° C. to about 80° C.

14. A double stranded RNA (dsRNA) agent that inhibits expression of a serine peptidase inhibitor, clade A, member 1 (Serpina1) target gene sequence, comprising a sense strand and an antisense strand forming a double stranded region, wherein the antisense strand comprises at least 19 contiguous nucleotides differing by no more than 3 nucleotides from the nucleotide sequence of 5'-UUUUGUUCAAUCAUUAAGAAGAC-3' (SEQ ID NO: 419), wherein all of the nucleotides of the antisense strand comprise a nucleotide modification selected from the group consisting of a thermally destabilizing modification, a 2'-F modification and a 2'-OMe modification, wherein the thermally destabilizing modification is located in position 4 to 8 from the 5'-end of the antisense strand and is selected from the group consisting of an abasic modification, a mismatch with the opposing nucleotide in the opposing strand, a 2'-deoxy modification, and an acyclic nucleotide modification, wherein the nucleotides at positions 2, 6, 8, 9, 14, and 16, or at positions 2, 6, 14, and 16, or at positions 2, 14, and 16 from the 5'-end of the antisense strand are 2'-F modified nucleotides, wherein all of the nucleotides of the sense strand comprise a nucleotide modification, wherein the nucleotides at positions 7, 9, 10, and 11, or at positions 7, 10, and 11 from the 5'-end of the sense strand are 2'-F modified nucleotides, wherein each of the sense strand and the antisense strand are independently 19 to 25 nucleotides in length, and wherein the dsRNA agent has a melting temperature of from about 40° C. to about 80° C.

15. The dsRNA agent of claim 13 or 14, wherein the thermally destabilizing modification is selected from the group consisting of

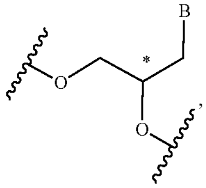
,
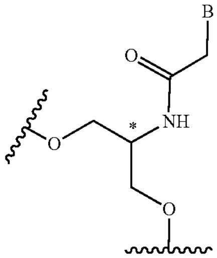
,

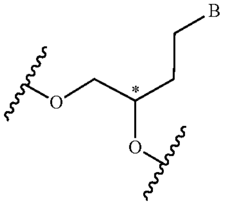

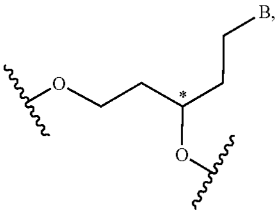
,

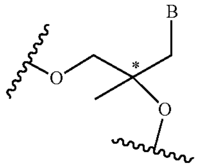
, and
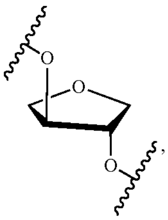
, wherein B is nucleobase.

16. The dsRNA agent of claim 13 or 14, wherein the destabilizing modification is located at position 7 of the antisense strand.

17. The dsRNA agent of claim 13 or 14, further comprising an ASGPR ligand.

18. The dsRNA agent of claim 17, wherein the ASGPR ligand is one or more GalNAc derivatives attached through a bivalent or trivalent branched linker.

19. The dsRNA agent of claim 18, wherein the ASGPR ligand is:

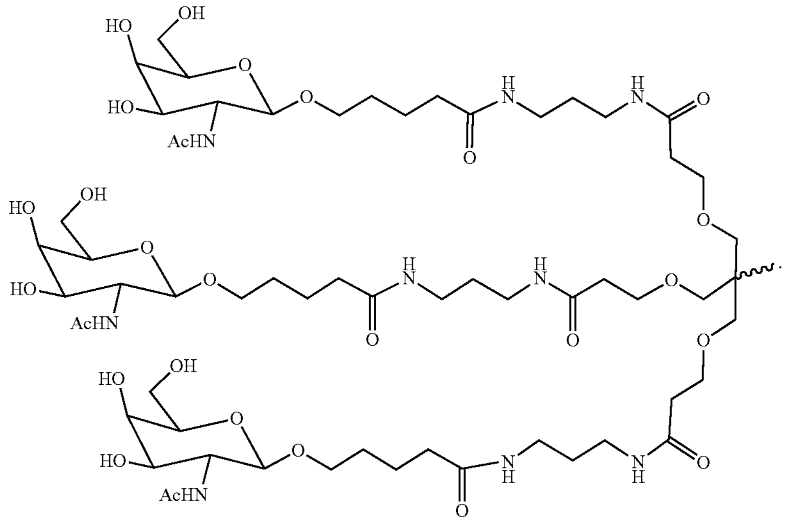 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]
20. The dsRNA agent of claim 19, wherein the dsRNA agent is conjugated to the ligand as shown in the following schematic
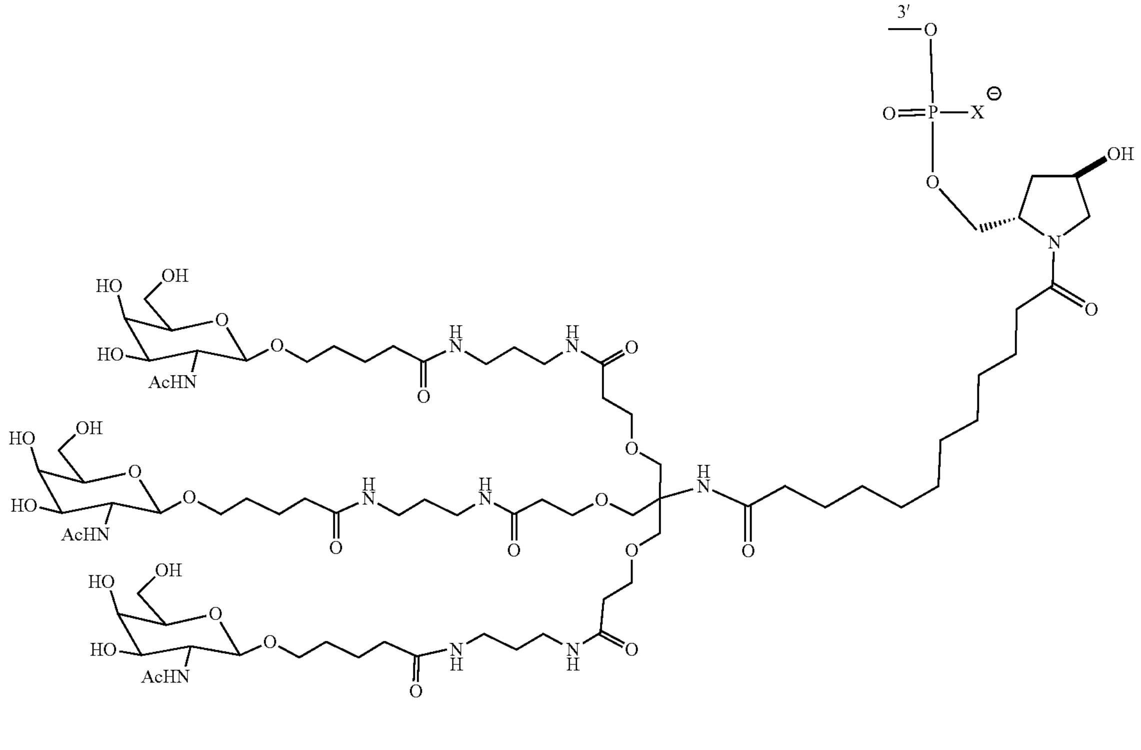
wherein X is O or S.

21. The dsRNA agent of any one of claim 1, 4, 13, or 14, wherein each strand is independently 19 to 23 nucleotides in length.

22. The dsRNA agent of any one of claim 1, 4, 13, or 14, wherein the sense strand is 21 nucleotides in length and the antisense strand is 23 nucleotides in length.

23. The dsRNA agent of any one of claim 1, 4, 13, or 14, wherein the nucleotides at positions 2, 14, and 16 from the 5'-end of the antisense strand are 2'-F modified nucleotides.

24. The dsRNA agent of any one of claim 1, 4, 13, or 14, wherein the nucleotides at positions 7, 9, 10, and 11 from the 5'-end of the sense strand are 2'-F modified nucleotides.

25. The dsRNA agent of any one of claim 1, 4, 13, or 14, wherein the sense strand further comprises two phosphorothioate or methylphosphonate internucleotide linkages.

26. The dsRNA agent of claim 25, wherein the two phosphorothioate or methylphosphonate internucleotide linkages are located between nucleotide positions 1 and 2 and between nucleotide positions 2 and 3 from the 5'-end of the sense strand.

27. The dsRNA agent of any one of claim 1, 4, 13, or 14, wherein the antisense strand further comprises four phosphorothioate or methylphosphonate internucleotide linkages.

28. The dsRNA agent of claim 27, wherein the four phosphorothioate or methylphosphonate internucleotide linkages are located between nucleotide positions 1 and 2, between nucleotide positions 2 and 3, between nucleotide positions 21 and 22, and between nucleotide positions 22 and 23 from the 5'-end of the antisense strand.

29. The dsRNA agent of any one of claim 1, 4, 13, or 14, wherein at least one strand comprises a 3' overhang of at least 1 nucleotide.

30. The dsRNA agent of any one of claim 1, 4, 13, or 14, wherein at least one strand comprises a 3' overhang of at least 2 nucleotides.

31. The dsRNA agent of any one of claim 1, 4, 13, or 14, wherein the antisense strand differs by no more than 2 nucleotides from from the nucleotide sequence of 5'-UUUUGUUCAAUCAUUAAGAAGAC-3' (SEQ ID NO: 419).

32. The dsRNA agent of any one of claim 1, 4, 13, or 14, wherein the antisense strand differs by no more than 1 nucleotide from from the nucleotide sequence of 5'-UUUUGUUCAAUCAUUAAGAAGAC-3' (SEQ ID NO: 419).

33. The dsRNA agent of any one of claim 1, 4, 13, or 14, wherein the antisense strand comprises the nucleotide sequence 5'-UUUUGUUCAAUCAUUAAGAAGAC-3' (SEQ ID NO: 419).

34. The dsRNA agent of any one of claim 1, 4, 13, or 14, wherein the sense strand comprises the nucleotide sequence 5'-CUUCUUAAUGAUUGAACAAAA-3' (SEQ ID NO: 417) and the antisense strand comprises the nucleotide sequence 5'-UUUUGUUCAAUCAUUAAGAAGAC-3' (SEQ ID NO: 419).

35. The dsRNA agent of any one of claim 1, 4, 13, or 14, wherein the sense strand comprises the nucleotide sequence 5'-csusucuuAfaUfGfAfuugaacaaaa-3' (SEQ ID NO: 33) and the antisense strand comprises the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA) S-Isomer.

36. The dsRNA agent of claim 33, wherein the sense strand consists of the nucleotide sequence 5'-csusucuuAfaUfGfAfuugaacaaaaL96-3' (SEQ ID NO: 35) and the antisense strand consists of the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; (Tgn) is a thymidine-glycol nucleic acid (GNA) S-Isomer; and L96 is N-[tris(GalNAc-alkyl)-amidodecanoyl)]-4-hydroxyprolinol.

37. A double stranded RNA (dsRNA) agent that inhibits expression of a serine peptidase inhibitor, clade A, member 1 (Serpina1) gene, comprising a sense strand and an antisense strand forming a double stranded region, wherein the sense strand comprises the nucleotide sequence 5'-csusucuuAfaUfGfAfuugaacaaaaL96-3' (SEQ ID NO: 35) and the antisense strand comprises the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; (Tgn) is a thymidine-glycol nucleic acid (GNA) S-Isomer; and L96 is N-[tris(GalNAc-alkyl)-amidodecanoyl)]-4-hydroxyprolinol.

38. An isolated cell containing the dsRNA agent of any one of claim 13, 14, or 37.

39. A pharmaceutical composition comprising the dsRNA agent of any one of claim 13, 14, or 37.

40. A double stranded RNA (dsRNA) agent that inhibits expression of a serine peptidase inhibitor, clade A, member 1 (Serpina1) gene, comprising a sense strand and an antisense strand forming a double stranded region, wherein the sense strand comprises the nucleotide sequence 5'-csusucuuAfaUfGfAfuugaacaaaa-3' (SEQ ID NO: 33) and the antisense strand comprises the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA) S-Isomer; and wherein the 3'-end of the sense strand is conjugated to a ligand as shown in the following schematic

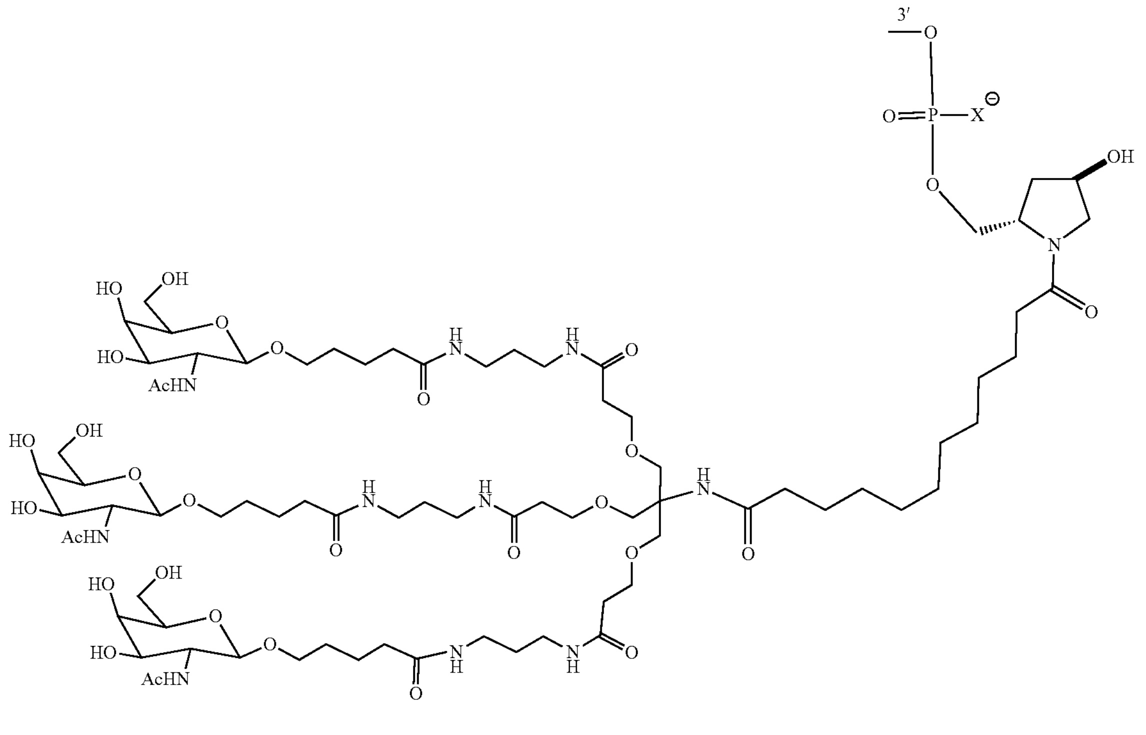

wherein X is O.

41. A pharmaceutical composition, comprising a double stranded RNA (dsRNA) agent that inhibits expression of a serine peptidase inhibitor, clade A, member 1 (Serpina1) gene, wherein the dsRNA agent comprises a sense strand and an antisense strand forming a double stranded region, wherein the sense strand comprises the nucleotide sequence 5'-csusucuuAfaUfGfAfuugaacaaaa-3' (SEQ ID NO: 33) and the antisense strand comprises the nucleotide sequence 5'-usUfsuugu(Tgn)caaucaUfuAfagaagsasc-3' (SEQ ID NO: 34), wherein a, g, c, and u are 2'-O-methyl (2'-OMe) A, G, C, and U, respectively; Af, Gf, Cf and Uf are 2'-fluoro A, G, C and U, respectively; s is a phosphorothioate linkage; and (Tgn) is a thymidine-glycol nucleic acid (GNA) S-Isomer; and wherein the 3'-end of the sense strand is conjugated to a ligand as shown in the following schematic

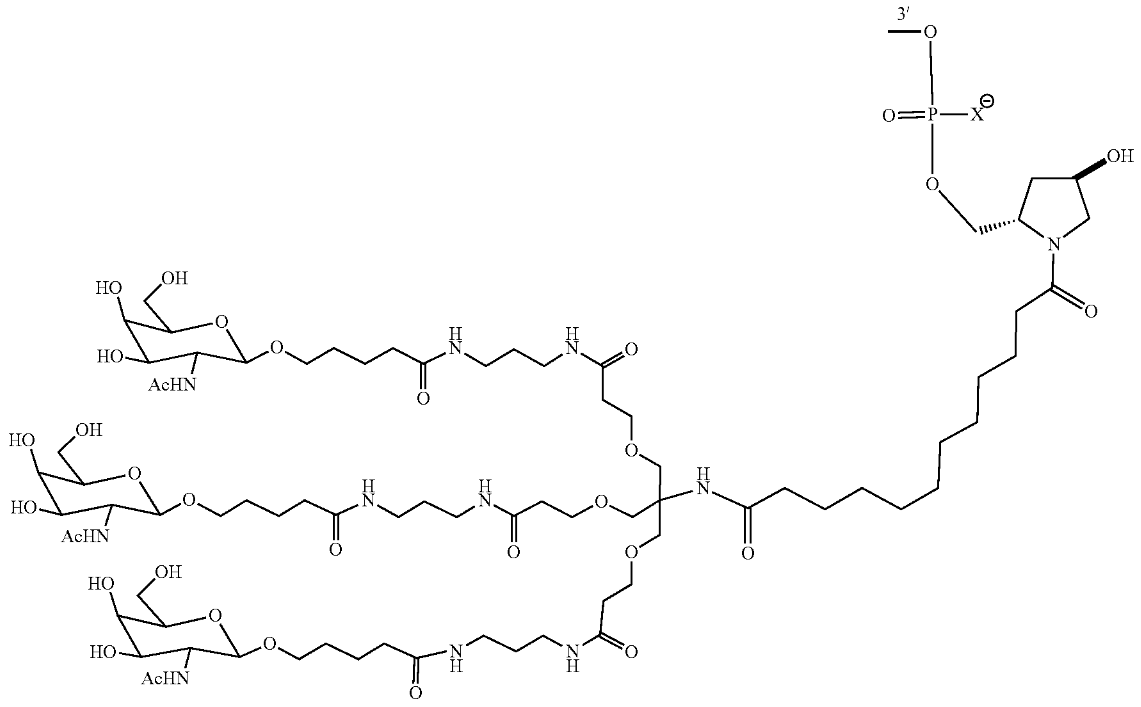
wherein X is O.
* * * * *

SEQUENCE LISTING

```
<160> NUMBER OF SEQ ID NOS: 420

<210> SEQ ID NO 1
<211> LENGTH: 3220
<212> TYPE: DNA
<213> ORGANISM: Homo sapiens

<400> SEQUENCE: 1

acaatgactc ctttcggtaa gtgcagtgga agctgtacac tgcccaggca aagcgtccgg     60

gcagcgtagg cgggcgactc agatcccagc cagtggactt agcccctgtt tgctcctccg    120

ataactgggg tgaccttggt taatattcac cagcagcctc ccccgttgcc cctctggatc    180

cactgcttaa atacggacga ggacagggcc ctgtctcctc agcttcaggc accaccactg    240

acctgggaca gtgaatcgac aatgccgtct tctgtctcgt ggggcatcct cctgctggca    300

ggcctgtgct gcctggtccc tgtctccctg gctgaggatc cccagggaga tgctgcccag    360

aagacagata catcccacca tgatcaggat cacccaacct tcaacaagat cacccccaac    420

ctggctgagt tcgccttcag cctataccgc cagctggcac accagtccaa cagcaccaat    480

atcttcttct ccccagtgag catcgctaca gcctttgcaa tgctctccct ggggaccaag    540

gctgacactc acgatgaaat cctggagggc ctgaatttca acctcacgga gattccggag    600

gctcagatcc atgaaggctt ccaggaactc ctccgtaccc tcaaccagcc agacagccag    660

ctccagctga ccaccggcaa tggcctgttc ctcagcgagg gcctgaagct agtggataag    720

tttttggagg atgttaaaaa gttgtaccac tcagaagcct tcactgtcaa cttcggggac    780

accgaagagg ccaagaaaca gatcaacgat tacgtggaga agggtactca agggaaaatt    840

gtggatttgg tcaaggagct tgacagagac acagtttttg ctctggtgaa ttacatcttc    900

tttaaaggca aatgggagag accctttgaa gtcaaggaca ccgaggaaga ggacttccac    960

gtggaccagg tgaccaccgt gaaggtgcct atgatgaagc gtttaggcat gtttaacatc   1020

cagcactgta agaagctgtc cagctgggtg ctgctgatga aatacctggg caatgccacc   1080

gccatcttct tcctgcctga tgaggggaaa ctacagcacc tggaaaatga actcacccac   1140

gatatcatca ccaagttcct ggaaaatgaa gacagaaggt ctgccagctt acatttaccc   1200

aaactgtcca ttactggaac ctatgatctg aagagcgtcc tgggtcaact gggcatcact   1260

aaggtcttca gcaatggggc tgacctctcc ggggtcacag aggaggcacc cctgaagctc   1320

tccaaggccg tgcataaggc tgtgctgacc atcgacgaga aagggactga agctgctggg   1380

gccatgtttt tagaggccat acccatgtct atcccccccg aggtcaagtt caacaaaccc   1440

tttgtcttct taatgattga acaaaatacc aagtctcccc tcttcatggg aaaagtggtg   1500

aatcccaccc aaaaataact gcctctcgct cctcaacccc tcccctccat ccctggcccc   1560

ctccctggat gacattaaag aagggttgag ctggtccctg cctgcatgtg actgtaaatc   1620

cctcccatgt tttctctgag tctccctttg cctgctgagg ctgtatgtgg gctccaggta   1680
```

acagtgctgt cttcgggccc cctgaactgt gttcatggag catctggctg ggtaggcaca 1740
tgctgggctt gaatccaggg gggactgaat cctcagctta cggacctggg cccatctgtt 1800
tctggagggc tccagtcttc cttgtcctgt cttggagtcc ccaagaagga atcacagggg 1860
aggaaccaga taccagccat gaccccaggc tccaccaagc atcttcatgt ccccctgctc 1920
atcccccact cccccccacc cagagttgct catcctgcca gggctggctg tgcccacccc 1980
aaggctgccc tcctgggggc cccagaactg cctgatcgtg ccgtggccca gttttgtggc 2040
atctgcagca acacaagaga gaggacaatg tcctcctctt gacccgctgt cacctaacca 2100
gactcgggcc ctgcacctct caggcacttc tggaaaatga ctgaggcaga ttcttcctga 2160
agcccattct ccatggggca acaaggacac ctattctgtc cttgtccttc catcgctgcc 2220
ccagaaagcc tcacatatct ccgtttagaa tcaggtccct tctccccaga tgaagaggag 2280
ggtctctgct ttgttttctc tatctcctcc tcagacttga ccaggcccag caggccccag 2340
aagaccatta ccctatatcc cttctcctcc ctagtcacat ggccataggc ctgctgatgg 2400
ctcaggaagg ccattgcaag gactcctcag ctatgggaga ggaagcacat cacccattga 2460
cccccgcaac ccctcccttt cctcctctga gtcccgactg gggccacatg cagcctgact 2520
tctttgtgcc tgttgctgtc cctgcagtct tcagagggcc accgcagctc cagtgccacg 2580
gcaggaggct gttcctgaat agcccctgtg gtaagggcca ggagagtcct tccatcctcc 2640
aaggccctgc taaaggacac agcagccagg aagtcccctg ggcccctagc tgaaggacag 2700
cctgctccct ccgtctctac caggaatggc cttgtcctat ggaaggcact gccccatccc 2760
aaactaatct aggaatcact gtctaaccac tcactgtcat gaatgtgtac ttaaaggatg 2820
aggttgagtc ataccaaata gtgatttcga tagttcaaaa tggtgaaatt agcaattcta 2880
catgattcag tctaatcaat ggataccgac tgtttcccac acaagtctcc tgttctctta 2940
agcttactca ctgacagcct ttcactctcc acaaatacat taaagatatg gccatcacca 3000
agccccctag gatgacacca gacctgagag tctgaagacc tggatccaag ttctgacttt 3060
tccccctgac agctgtgtga ccttcgtgaa gtcgccaaac ctctctgagc cccagtcatt 3120
gctagtaaga cctgcctttg agttggtatg atgttcaagt tagataacaa aatgtttata 3180
cccattagaa cagagaataa atagaactac atttcttgca 3220

<210> SEQ ID NO 2
<211> LENGTH: 3199
<212> TYPE: DNA
<213> ORGANISM: Homo sapiens

<400> SEQUENCE: 2
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaaggaca 240
atgccgtctt ctgtctcgtg gggcatcctc ctgctggcag gcctgtgctg cctggtccct 300
gtctccctgg ctgaggatcc ccagggagat gctgcccaga agacagatac atcccaccat 360
gatcaggatc acccaacctt caacaagatc acccccaacc tggctgagtt cgccttcagc 420
ctataccgcc agctggcaca ccagtccaac agcaccaata tcttcttctc cccagtgagc 480
atcgctacag cctttgcaat gctctccctg gggaccaagg ctgacactca cgatgaaatc 540
ctggagggcc tgaatttcaa cctcacggag attccggagg ctcagatcca tgaaggcttc 600

-continued

```
caggaactcc tccgtaccct caaccagcca gacagccagc tccagctgac caccggcaat    660
ggcctgttcc tcagcgaggg cctgaagcta gtggataagt tttggagga tgttaaaaag    720
ttgtaccact cagaagcctt cactgtcaac ttcggggaca ccgaagaggc caagaaacag    780
atcaacgatt acgtggagaa gggtactcaa gggaaaattg tggatttggt caaggagctt    840
gacagagaca cagtttttgc tctggtgaat tacatcttct ttaaaggcaa atgggagaga    900
ccctttgaag tcaaggacac cgaggaagag gacttccacg tggaccaggt gaccaccgtg    960
aaggtgccta tgatgaagcg tttaggcatg tttaacatcc agcactgtaa gaagctgtcc   1020
agctgggtgc tgctgatgaa atacctgggc aatgccaccg ccatcttctt cctgcctgat   1080
gaggggaaac tacagcacct ggaaaatgaa ctcacccacg atatcatcac caagttcctg   1140
gaaaatgaag acagaaggtc tgccagctta catttaccca aactgtccat tactggaacc   1200
tatgatctga agagcgtcct gggtcaactg ggcatcacta aggtcttcag caatggggct   1260
gacctctccg ggtcacaga ggaggcaccc ctgaagctct ccaaggccgt gcataaggct   1320
gtgctgacca tcgacgagaa agggactgaa gctgctgggg ccatgttttt agaggccata   1380
cccatgtcta tccccccga ggtcaagttc aacaaaccct ttgtcttctt aatgattgaa   1440
caaaatacca agtctcccct cttcatggga aaagtggtga atcccaccca aaaataactg   1500
cctctcgctc ctcaacccct cccctccatc cctggccccc tccctggatg acattaaaga   1560
agggttgagc tggtccctgc ctgcatgtga ctgtaaatcc ctcccatgtt ttctctgagt   1620
ctccctttgc ctgctgaggc tgtatgtggg ctccaggtaa cagtgctgtc ttcgggcccc   1680
ctgaactgtg ttcatggagc atctggctgg gtaggcacat gctgggcttg aatccagggg   1740
ggactgaatc ctcagcttac ggacctgggc ccatctgttt ctggagggct ccagtcttcc   1800
ttgtcctgtc ttggagtccc caagaaggaa tcacagggga ggaaccagat accagccatg   1860
accccaggct ccaccaagca tcttcatgtc cccctgctca tcccccactc ccccccaccc   1920
agagttgctc atcctgccag ggctggctgt gcccacccca aggctgccct cctgggggcc   1980
ccagaactgc ctgatcgtgc cgtggcccag ttttgtggca tctgcagcaa cacaagagag   2040
aggacaatgt cctcctcttg acccgctgtc acctaaccag actcgggccc tgcacctctc   2100
aggcacttct ggaaaatgac tgaggcagat tcttcctgaa gcccattctc catggggcaa   2160
caaggacacc tattctgtcc ttgtccttcc atcgctgccc cagaaagcct cacatatctc   2220
cgtttagaat caggtccctt ctccccagat gaagaggagg gtctctgctt tgttttctct   2280
atctcctcct cagacttgac caggcccagc aggccccaga agaccattac cctatatccc   2340
ttctcctccc tagtcacatg gccataggcc tgctgatggc tcaggaaggc cattgcaagg   2400
actcctcagc tatgggagag gaagcacatc acccattgac cccgcaacc cctcccttc   2460
ctcctctgag tcccgactgg ggccacatgc agcctgactt ctttgtgcct gttgctgtcc   2520
ctgcagtctt cagagggcca ccgcagctcc agtgccacgg caggaggctg ttcctgaata   2580
gcccctgtgg taagggccag gagagtcctt ccatcctcca aggccctgct aaaggacaca   2640
gcagccagga agtcccctgg gcccctagct gaaggacagc ctgctccctc cgtctctacc   2700
aggaatggcc ttgtcctatg gaaggcactg ccccatccca aactaatcta ggaatcactg   2760
tctaaccact cactgtcatg aatgtgtact taaaggatga ggttgagtca taccaaatag   2820
tgatttcgat agttcaaaat ggtgaaatta gcaattctac atgattcagt ctaatcaatg   2880
gataccgact gtttcccaca caagtctcct gttctcttaa gcttactcac tgacagcctt   2940
```

-continued tcactctcca caaatacatt aaagatatgg ccatcaccaa gccccctagg atgacaccag 3000
acctgagagt ctgaagacct ggatccaagt tctgactttt ccccctgaca gctgtgtgac 3060
cttcgtgaag tcgccaaacc tctctgagcc ccagtcattg ctagtaagac ctgcctttga 3120
gttggtatga tgttcaagtt agataacaaa atgtttatac ccattagaac agagaataaa 3180
tagaactaca tttcttgca 3199

<210> SEQ ID NO 3
<211> LENGTH: 3513
<212> TYPE: DNA
<213> ORGANISM: Homo sapiens

<400> SEQUENCE: 3
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaagggcg 240
gcagtaagtc ttcagcatca ggcattttgg ggtgactcag taaatggtag atcttgctac 300
cagtggaaca gccactaagg attctgcagt gagagcagag ggccagctaa gtggtactct 360
cccagagact gtctgactca cgccaccccc tccaccttgg acacaggacg ctgtggtttc 420
tgagccaggt acaatgactc ctttcgcagc ctcccccgtt gcccctctgg atccactgct 480
taaatacgga cgaggacagg gccctgtctc ctcagcttca ggcaccacca ctgacctggg 540
acagtgaatc gacaatgccg tcttctgtct cgtggggcat cctcctgctg gcaggcctgt 600
gctgcctggt ccctgtctcc ctggctgagg atccccaggg agatgctgcc cagaagacag 660
atacatccca ccatgatcag gatcacccaa ccttcaacaa gatcaccccc aacctggctg 720
agttcgcctt cagcctatac cgccagctgg cacaccagtc caacagcacc aatatcttct 780
tctccccagt gagcatcgct acagcctttg caatgctctc cctggggacc aaggctgaca 840
ctcacgatga aatcctggag ggcctgaatt tcaacctcac ggagattccg gaggctcaga 900
tccatgaagg cttccaggaa ctcctccgta ccctcaacca gccagacagc cagctccagc 960
tgaccaccgg caatggcctg ttcctcagcg agggcctgaa gctagtggat aagtttttgg 1020
aggatgttaa aaagttgtac cactcagaag ccttcactgt caacttcggg gacaccgaag 1080
aggccaagaa acagatcaac gattacgtgg agaagggtac tcaagggaaa attgtggatt 1140
tggtcaagga gcttgacaga gacacagttt ttgctctggt gaattacatc ttctttaaag 1200
gcaaatggga gagacccttt gaagtcaagg acaccgagga agaggacttc cacgtggacc 1260
aggtgaccac cgtgaaggtg cctatgatga agcgtttagg catgtttaac atccagcact 1320
gtaagaagct gtccagctgg gtgctgctga tgaaatacct gggcaatgcc accgccatct 1380
tcttcctgcc tgatgagggg aaactacagc acctggaaaa tgaactcacc cacgatatca 1440
tcaccaagtt cctggaaaat gaagacagaa ggtctgccag cttacattta cccaaactgt 1500
ccattactgg aacctatgat ctgaagagcg tcctgggtca actgggcatc actaaggtct 1560
tcagcaatgg ggctgacctc tccggggtca cagaggaggc acccctgaag ctctccaagg 1620
ccgtgcataa ggctgtgctg accatcgacg agaaagggac tgaagctgct ggggccatgt 1680
ttttagaggc catacccatg tctatccccc ccgaggtcaa gttcaacaaa ccctttgtct 1740
tcttaatgat tgaacaaaat accaagtctc ccctcttcat gggaaaagtg gtgaatccca 1800
cccaaaaata actgcctctc gctcctcaac ccctcccctc catccctggc cccctccctg 1860
gatgacatta aagaagggtt gagctggtcc ctgcctgcat gtgactgtaa atccctccca 1920
tgttttctct gagtctccct ttgcctgctg aggctgtatg tgggctccag gtaacagtgc 1980
tgtcttcggg ccccctgaac tgtgttcatg gagcatctgg ctgggtaggc acatgctggg 2040
cttgaatcca ggggggactg aatcctcagc ttacggacct gggcccatct gtttctggag 2100
ggctccagtc ttccttgtcc tgtcttggag tccccaagaa ggaatcacag gggaggaacc 2160
agataccagc catgacccca ggctccacca agcatcttca tgtccccctg ctcatccccc 2220
actccccccc acccagagtt gctcatcctg ccagggctgg ctgtgcccac cccaaggctg 2280
ccctcctggg ggccccagaa ctgcctgatc gtgccgtggc ccagttttgt ggcatctgca 2340
gcaacacaag agagaggaca atgtcctcct cttgacccgc tgtcacctaa ccagactcgg 2400
gccctgcacc tctcaggcac ttctggaaaa tgactgaggc agattcttcc tgaagcccat 2460
tctccatggg gcaacaagga cacctattct gtccttgtcc ttccatcgct gccccagaaa 2520
gcctcacata tctccgttta gaatcaggtc ccttctcccc agatgaagag gagggtctct 2580
gctttgtttt ctctatctcc tcctcagact tgaccaggcc cagcaggccc cagaagacca 2640
ttaccctata tcccttctcc tccctagtca catggccata ggcctgctga tggctcagga 2700
aggccattgc aaggactcct cagctatggg agaggaagca catcacccat tgaccccccgc 2760 aacccctccc tttcctcctc tgagtcccga ctggggccac atgcagcctg acttctttgt 2820
gcctgttgct gtccctgcag tcttcagagg gccaccgcag ctccagtgcc acggcaggag 2880
gctgttcctg aatagcccct gtggtaaggg ccaggagagt ccttccatcc tccaaggccc 2940
tgctaaagga cacagcagcc aggaagtccc ctgggcccct agctgaagga cagcctgctc 3000
cctccgtctc taccaggaat ggccttgtcc tatggaaggc actgccccat cccaaactaa 3060
tctaggaatc actgtctaac cactcactgt catgaatgtg tacttaaagg atgaggttga 3120
gtcataccaa atagtgattt cgatagttca aaatggtgaa attagcaatt ctacatgatt 3180
cagtctaatc aatggatacc gactgtttcc cacacaagtc tcctgttctc ttaagcttac 3240
tcactgacag cctttcactc tccacaaata cattaaagat atggccatca ccaagccccc 3300
taggatgaca ccagacctga gagtctgaag acctggatcc aagttctgac ttttccccct 3360
gacagctgtg tgaccttcgt gaagtcgcca aacctctctg agccccagtc attgctagta 3420
agacctgcct ttgagttggt atgatgttca agttagataa caaaatgttt atacccatta 3480
gaacagagaa taaatagaac tacatttctt gca 3513

<210> SEQ ID NO 4
<211> LENGTH: 3236
<212> TYPE: DNA
<213> ORGANISM: Homo sapiens

<400> SEQUENCE: 4
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaaggtgg 240
gacattgctg ctgctgctca ctcagttcca caggacaatg ccgtcttctg tctcgtgggg 300
catcctcctg ctggcaggcc tgtgctgcct ggtccctgtc tccctggctg aggatcccca 360
gggagatgct gcccagaaga cagatacatc ccaccatgat caggatcacc caaccttcaa 420

-continued

```
caagatcacc cccaacctgg ctgagttcgc cttcagccta taccgccagc tggcacacca    480
gtccaacagc accaatatct tcttctcccc agtgagcatc gctacagcct ttgcaatgct    540
ctccctgggg accaaggctg acactcacga tgaaatcctg gagggcctga atttcaacct    600
cacggagatt ccggaggctc agatccatga aggcttccag gaactcctcc gtaccctcaa    660
ccagccagac agccagctcc agctgaccac cggcaatggc ctgttcctca gcgagggcct    720
gaagctagtg gataagtttt tggaggatgt taaaaagttg taccactcag aagccttcac    780
tgtcaacttc ggggacaccg aagaggccaa gaaacagatc aacgattacg tggagaaggg    840
tactcaaggg aaaattgtgg atttggtcaa ggagcttgac agagacacag tttttgctct    900
ggtgaattac atcttcttta aaggcaaatg ggagagaccc tttgaagtca aggacaccga    960
ggaagaggac ttccacgtgg accaggtgac caccgtgaag gtgcctatga tgaagcgttt   1020
aggcatgttt aacatccagc actgtaagaa gctgtccagc tgggtgctgc tgatgaaata   1080
cctgggcaat gccaccgcca tcttcttcct gcctgatgag gggaaactac agcacctgga   1140
aaatgaactc acccacgata tcatcaccaa gttcctggaa aatgaagaca gaaggtctgc   1200
cagcttacat ttacccaaac tgtccattac tggaacctat gatctgaaga gcgtcctggg   1260
tcaactgggc atcactaagg tcttcagcaa tggggctgac ctctccgggg tcacagagga   1320
ggcacccctg aagctctcca aggccgtgca taaggctgtg ctgaccatcg acgagaaagg   1380
gactgaagct gctggggcca tgtttttaga ggccataccc atgtctatcc cccccgaggt   1440
caagttcaac aaaccctttg tcttcttaat gattgaacaa aataccaagt ctcccctctt   1500
catgggaaaa gtggtgaatc ccacccaaaa ataactgcct ctcgctcctc aacccctccc   1560
ctccatccct ggccccctcc ctggatgaca ttaaagaagg gttgagctgg tccctgcctg   1620
catgtgactg taaatccctc ccatgttttc tctgagtctc cctttgcctg ctgaggctgt   1680
atgtgggctc caggtaacag tgctgtcttc gggccccctg aactgtgttc atggagcatc   1740
tggctgggta ggcacatgct gggcttgaat ccaggggggga ctgaatcctc agcttacgga   1800
cctgggccca tctgtttctg gagggctcca gtcttccttg tcctgtcttg gagtccccaa   1860
gaaggaatca caggggagga accagatacc agccatgacc ccaggctcca ccaagcatct   1920
tcatgtcccc ctgctcatcc cccactcccc cccacccaga gttgctcatc ctgccagggc   1980
tggctgtgcc caccccaagg ctgccctcct gggggcccca gaactgcctg atcgtgccgt   2040
ggcccagttt tgtggcatct gcagcaacac aagagagagg acaatgtcct cctcttgacc   2100
cgctgtcacc taaccagact cgggccctgc acctctcagg cacttctgga aaatgactga   2160
ggcagattct tcctgaagcc cattctccat ggggcaacaa ggacacctat tctgtccttg   2220
tccttccatc gctgccccag aaagcctcac atatctccgt ttagaatcag gtcccttctc   2280
cccagatgaa gaggagggtc tctgctttgt tttctctatc tcctcctcag acttgaccag   2340
gcccagcagg ccccagaaga ccattaccct atatcccttc tcctccctag tcacatggcc   2400
ataggcctgc tgatggctca ggaaggccat tgcaaggact cctcagctat gggagaggaa   2460
gcacatcacc cattgacccc cgcaacccct cccttttcctc ctctgagtcc cgactggggc   2520
cacatgcagc ctgacttctt tgtgcctgtt gctgtccctg cagtcttcag agggccaccg   2580
cagctccagt gccacggcag gaggctgttc ctgaatagcc cctgtggtaa gggccaggag   2640
agtccttcca tcctccaagg ccctgctaaa ggacacagca gccaggaagt cccctgggcc   2700
cctagctgaa ggacagcctg ctccctccgt ctctaccagg aatggccttg tcctatggaa   2760
ggcactgccc catcccaaac taatctagga atcactgtct aaccactcac tgtcatgaat   2820
```

-continued

```
gtgtacttaa aggatgaggt tgagtcatac caaatagtga tttcgatagt tcaaaatggt   2880

gaaattagca attctacatg attcagtcta atcaatggat accgactgtt tcccacacaa   2940

gtctcctgtt ctcttaagct tactcactga cagcctttca ctctccacaa atacattaaa   3000

gatatggcca tcaccaagcc ccctaggatg acaccagacc tgagagtctg aagacctgga   3060

tccaagttct gacttttccc cctgacagct gtgtgacctt cgtgaagtcg ccaaacctct   3120

ctgagcccca gtcattgcta gtaagacctg cctttgagtt ggtatgatgt tcaagttaga   3180

taacaaaatg tttataccca ttagaacaga gaataaatag aactacattt cttgca       3236
```

<210> SEQ ID NO 5
<211> LENGTH: 3532
<212> TYPE: DNA
<213> ORGANISM: Homo sapiens

<400> SEQUENCE: 5

```
tgggcaggaa ctgggcactg tgcccagggc atgcactgcc tccacgcagc aaccctcaga     60

gtcctgagct gaaccaagaa ggaggagggg gtcgggcctc cgaggaaggc ctagccgctg    120

ctgctgccag gaattccagg ttggaggggc ggcaacctcc tgccagcctt caggccactc    180

tcctgtgcct gccagaagag acagagcttg aggagagctt gaggagagca ggaaaggtgg    240

gacattgctg ctgctgctca ctcagttcca cagggcggca gtaagtcttc agcatcaggc    300

attttggggt gactcagtaa atggtagatc ttgctaccag tggaacagcc actaaggatt    360

ctgcagtgag agcagagggc cagctaagtg gtactctccc agagactgtc tgactcacgc    420

cacccccctcc accttggaca caggacgctg tggtttctga gccagcagcc tcccccgttg    480

cccctctgga tccactgctt aaatacggac gaggacaggg ccctgtctcc tcagcttcag    540

gcaccaccac tgacctggga cagtgaatcg acaatgccgt cttctgtctc gtggggcatc    600

ctcctgctgg caggcctgtg ctgcctggtc cctgtctccc tggctgagga tccccaggga    660

gatgctgccc agaagacaga tacatcccac catgatcagg atcacccaac cttcaacaag    720

atcaccccca acctggctga gttcgccttc agcctatacc gccagctggc acaccagtcc    780

aacagcacca atatcttctt ctccccagtg agcatcgcta cagcctttgc aatgctctcc    840

ctggggacca aggctgacac tcacgatgaa atcctggagg gcctgaattt caacctcacg    900

gagattccgg aggctcagat ccatgaaggc ttccaggaac tcctccgtac cctcaaccag    960

ccagacagcc agctccagct gaccaccggc aatggcctgt tcctcagcga gggcctgaag   1020

ctagtggata agtttttgga ggatgttaaa aagttgtacc actcagaagc cttcactgtc   1080

aacttcgggg acaccgaaga ggccaagaaa cagatcaacg attacgtgga gaagggtact   1140

caagggaaaa ttgtggattt ggtcaaggag cttgacagag acacagtttt tgctctggtg   1200

aattacatct tctttaaagg caaatgggag agaccctttg aagtcaagga caccgaggaa   1260

gaggacttcc acgtggacca ggtgaccacc gtgaaggtgc ctatgatgaa gcgtttaggc   1320

atgtttaaca tccagcactg taagaagctg tccagctggg tgctgctgat gaaatacctg   1380

ggcaatgcca ccgccatctt cttcctgcct gatgagggga aactacagca cctggaaaat   1440

gaactcaccc acgatatcat caccaagttc ctggaaaatg aagacagaag gtctgccagc   1500

ttacatttac ccaaactgtc cattactgga acctatgatc tgaagagcgt cctgggtcaa   1560

ctgggcatca ctaaggtctt cagcaatggg gctgacctct ccggggtcac agaggaggca   1620

cccctgaagc tctccaaggc cgtgcataag gctgtgctga ccatcgacga gaaagggact   1680
```

-continued gaagctgctg gggccatgtt tttagaggcc atacccatgt ctatcccccc cgaggtcaag 1740
ttcaacaaac cctttgtctt cttaatgatt gaacaaaata ccaagtctcc cctcttcatg 1800
ggaaaagtgg tgaatcccac ccaaaaataa ctgcctctcg ctcctcaacc cctcccctcc 1860
atccctggcc ccctccctgg atgacattaa agaagggttg agctggtccc tgcctgcatg 1920
tgactgtaaa tccctcccat gttttctctg agtctccctt tgcctgctga ggctgtatgt 1980
gggctccagg taacagtgct gtcttcgggc cccctgaact gtgttcatgg agcatctggc 2040
tgggtaggca catgctgggc ttgaatccag gggggactga atcctcagct tacggacctg 2100
ggcccatctg tttctggagg gctccagtct tccttgtcct gtcttggagt ccccaagaag 2160
gaatcacagg ggaggaacca gataccagcc atgaccccag gctccaccaa gcatcttcat 2220
gtccccctgc tcatccccca ctcccccccca cccagagttg ctcatcctgc cagggctggc 2280
tgtgcccacc ccaaggctgc cctcctgggg gccccagaac tgcctgatcg tgccgtggcc 2340
cagttttgtg gcatctgcag caacacaaga gagaggacaa tgtcctcctc ttgacccgct 2400
gtcacctaac cagactcggg ccctgcacct ctcaggcact tctggaaaat gactgaggca 2460
gattcttcct gaagcccatt ctccatgggg caacaaggac acctattctg tccttgtcct 2520
tccatcgctg ccccagaaag cctcacatat ctccgtttag aatcaggtcc cttctcccca 2580
gatgaagagg agggtctctg ctttgttttc tctatctcct cctcagactt gaccaggccc 2640
agcaggcccc agaagaccat taccctatat cccttctcct ccctagtcac atggccatag 2700
gcctgctgat ggctcaggaa ggccattgca aggactcctc agctatggga gaggaagcac 2760
atcacccatt gacccccgca accctccct ttcctcctct gagtcccgac tggggccaca 2820
tgcagcctga cttctttgtg cctgttgctg tccctgcagt cttcagaggg ccaccgcagc 2880
tccagtgcca cggcaggagg ctgttcctga atagcccctg tggtaagggc caggagagtc 2940
cttccatcct ccaaggccct gctaaaggac acagcagcca ggaagtcccc tgggccccta 3000
gctgaaggac agcctgctcc ctccgtctct accaggaatg gccttgtcct atggaaggca 3060
ctgccccatc ccaaactaat ctaggaatca ctgtctaacc actcactgtc atgaatgtgt 3120
acttaaagga tgaggttgag tcataccaaa tagtgatttc gatagttcaa aatggtgaaa 3180
ttagcaattc tacatgattc agtctaatca atggataccg actgtttccc acacaagtct 3240
cctgttctct taagcttact cactgacagc ctttcactct ccacaaatac attaaagata 3300
tggccatcac caagcccccct aggatgacac cagacctgag agtctgaaga cctggatcca 3360
agttctgact tttcccccctg acagctgtgt gaccttcgtg aagtcgccaa acctctctga 3420
gccccagtca ttgctagtaa gacctgcctt tgagttggta tgatgttcaa gttagataac 3480
aaaatgttta tacccattag aacagagaat aaatagaact acatttcttg ca 3532

<210> SEQ ID NO 6
<211> LENGTH: 3340
<212> TYPE: DNA
<213> ORGANISM: Homo sapiens

<400> SEQUENCE: 6
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaaggtgg 240
gacattgctg ctgctgctca ctcagttcca cagcagcctc ccccgttgcc cctctggatc 300

-continued

```
cactgcttaa atacggacga ggacagggcc ctgtctcctc agcttcaggc accaccactg    360
acctgggaca gtgaatcgac aatgccgtct tctgtctcgt ggggcatcct cctgctggca    420
ggcctgtgct gcctggtccc tgtctccctg gctgaggatc cccagggaga tgctgcccag    480
aagacagata catcccacca tgatcaggat cacccaacct tcaacaagat cacccccaac    540
ctggctgagt tcgccttcag cctataccgc cagctggcac accagtccaa cagcaccaat    600
atcttcttct ccccagtgag catcgctaca gcctttgcaa tgctctccct ggggaccaag    660
gctgacactc acgatgaaat cctggagggc ctgaatttca acctcacgga gattccggag    720
gctcagatcc atgaaggctt ccaggaactc ctccgtaccc tcaaccagcc agacagccag    780
ctccagctga ccaccggcaa tggcctgttc ctcagcgagg gcctgaagct agtggataag    840
tttttggagg atgttaaaaa gttgtaccac tcagaagcct tcactgtcaa cttcggggac    900
accgaagagg ccaagaaaca gatcaacgat tacgtggaga agggtactca agggaaaatt    960
gtggatttgg tcaaggagct tgacagagac acagtttttg ctctggtgaa ttacatcttc   1020
tttaaaggca aatgggagag accctttgaa gtcaaggaca ccgaggaaga ggacttccac   1080
gtggaccagg tgaccaccgt gaaggtgcct atgatgaagc gtttaggcat gtttaacatc   1140
cagcactgta agaagctgtc cagctgggtg ctgctgatga aatacctggg caatgccacc   1200
gccatcttct tcctgcctga tgaggggaaa ctacagcacc tggaaaatga actcacccac   1260
gatatcatca ccaagttcct ggaaaatgaa gacagaaggt ctgccagctt acatttaccc   1320
aaactgtcca ttactggaac ctatgatctg aagagcgtcc tgggtcaact gggcatcact   1380
aaggtcttca gcaatggggc tgacctctcc ggggtcacag aggaggcacc cctgaagctc   1440
tccaaggccg tgcataaggc tgtgctgacc atcgacgaga aagggactga agctgctggg   1500
gccatgtttt tagaggccat acccatgtct atcccccccg aggtcaagtt caacaaaccc   1560
tttgtcttct taatgattga acaaaatacc aagtctcccc tcttcatggg aaaagtggtg   1620
aatcccaccc aaaaataact gcctctcgct cctcaacccc tcccctccat ccctggcccc   1680
ctccctggat gacattaaag aagggttgag ctggtccctg cctgcatgtg actgtaaatc   1740
cctcccatgt tttctctgag tctccctttg cctgctgagg ctgtatgtgg gctccaggta   1800
acagtgctgt cttcgggccc cctgaactgt gttcatggag catctggctg ggtaggcaca   1860
tgctgggctt gaatccaggg gggactgaat cctcagctta cggacctggg cccatctgtt   1920
tctggagggc tccagtcttc cttgtcctgt cttggagtcc ccaagaagga atcacagggg   1980
aggaaccaga taccagccat gaccccaggc tccaccaagc atcttcatgt cccccctgctc   2040
atcccccact cccccccacc cagagttgct catcctgcca gggctggctg tgcccacccc   2100
aaggctgccc tcctgggggc cccagaactg cctgatcgtg ccgtggccca gttttgtggc   2160
atctgcagca acacaagaga gaggacaatg tcctcctctt gacccgctgt cacctaacca   2220
gactcgggcc ctgcacctct caggcacttc tggaaaatga ctgaggcaga ttcttcctga   2280
agcccattct ccatggggca acaaggacac ctattctgtc cttgtccttc catcgctgcc   2340
ccagaaagcc tcacatatct ccgtttagaa tcaggtccct tctccccaga tgaagaggag   2400
ggtctctgct ttgttttctc tatctcctcc tcagacttga ccaggcccag caggccccag   2460
aagaccatta ccctatatcc cttctcctcc ctagtcacat ggccataggc ctgctgatgg   2520
ctcaggaagg ccattgcaag gactcctcag ctatgggaga ggaagcacat cacccattga   2580
cccccgcaac ccctcccttt cctcctctga gtcccgactg ggccacatg cagcctgact   2640
```

```
tctttgtgcc tgttgctgtc cctgcagtct tcagagggcc accgcagctc cagtgccacg   2700

gcaggaggct gttcctgaat agcccctgtg gtaagggcca ggagagtcct tccatcctcc   2760

aaggccctgc taaaggacac agcagccagg aagtcccctg ggcccctagc tgaaggacag   2820

cctgctccct ccgtctctac caggaatggc cttgtcctat ggaaggcact gccccatccc   2880

aaactaatct aggaatcact gtctaaccac tcactgtcat gaatgtgtac ttaaaggatg   2940

aggttgagtc ataccaaata gtgatttcga tagttcaaaa tggtgaaatt agcaattcta   3000

catgattcag tctaatcaat ggataccgac tgtttcccac acaagtctcc tgttctctta   3060

agcttactca ctgacagcct ttcactctcc acaaatacat taaagatatg gccatcacca   3120

agccccctag gatgacacca gacctgagag tctgaagacc tggatccaag ttctgacttt   3180

tccccctgac agctgtgtga ccttcgtgaa gtcgccaaac ctctctgagc cccagtcatt   3240

gctagtaaga cctgcctttg agttggtatg atgttcaagt tagataacaa aatgtttata   3300

cccattagaa cagagaataa atagaactac atttcttgca                         3340
```

<210> SEQ ID NO 7
<211> LENGTH: 3495
<212> TYPE: DNA
<213> ORGANISM: Homo sapiens

<400> SEQUENCE: 7

```
tgggcaggaa ctgggcactg tgcccagggc atgcactgcc tccacgcagc aaccctcaga     60

gtcctgagct gaaccaagaa ggaggagggg gtcgggcctc cgaggaaggc ctagccgctg    120

ctgctgccag gaattccagg ttggaggggc ggcaacctcc tgccagcctt caggccactc    180

tcctgtgcct gccagaagag acagagcttg aggagagctt gaggagagca ggaaagggcg    240

gcagtaagtc ttcagcatca ggcattttgg ggtgactcag taaatggtag atcttgctac    300

cagtggaaca gccactaagg attctgcagt gagagcagag ggccagctaa gtggtactct    360

cccagagact gtctgactca cgccaccccc tccaccttgg acacaggacg ctgtggtttc    420

tgagccagca gcctccccg ttgcccctct ggatccactg cttaaatacg gacgaggaca     480

gggccctgtc tcctcagctt caggcaccac cactgacctg ggacagtgaa tcgacaatgc    540

cgtcttctgt ctcgtggggc atcctcctgc tggcaggcct gtgctgcctg gtccctgtct    600

ccctggctga ggatccccag ggagatgctg cccagaagac agatacatcc caccatgatc    660

aggatcaccc aaccttcaac aagatcaccc ccaacctggc tgagttcgcc ttcagcctat    720

accgccagct ggcacaccag tccaacagca ccaatatctt cttctcccca gtgagcatcg    780

ctacagcctt tgcaatgctc tccctgggga ccaaggctga cactcacgat gaaatcctgg    840

agggcctgaa tttcaacctc acggagattc cggaggctca gatccatgaa ggcttccagg    900

aactcctccg taccctcaac cagccagaca gccagctcca gctgaccacc ggcaatggcc    960

tgttcctcag cgagggcctg aagctagtgg ataagttttt ggaggatgtt aaaaagttgt   1020

accactcaga agccttcact gtcaacttcg gggacaccga agaggccaag aaacagatca   1080

acgattacgt ggagaagggt actcaaggga aaattgtgga tttggtcaag gagcttgaca   1140

gagacacagt tttgctctg gtgaattaca tcttctttaa aggcaaatgg gagagaccct    1200

ttgaagtcaa ggacaccgag gaagaggact tccacgtgga ccaggtgacc accgtgaagg   1260

tgcctatgat gaagcgttta ggcatgttta acatccagca ctgtaagaag ctgtccagct   1320

gggtgctgct gatgaaatac ctgggcaatg ccaccgccat cttcttcctg cctgatgagg   1380

ggaaactaca gcacctggaa aatgaactca cccacgatat catcaccaag ttcctggaaa   1440
```

```
atgaagacag aaggtctgcc agcttacatt tacccaaact gtccattact ggaacctatg   1500
atctgaagag cgtcctgggt caactgggca tcactaaggt cttcagcaat ggggctgacc   1560
tctccggggt cacagaggag gcacccctga agctctccaa ggccgtgcat aaggctgtgc   1620
tgaccatcga cgagaaaggg actgaagctg ctggggccat gtttttagag gccataccca   1680
tgtctatccc ccccgaggtc aagttcaaca aaccctttgt cttcttaatg attgaacaaa   1740
ataccaagtc tcccctcttc atgggaaaag tggtgaatcc cacccaaaaa taactgcctc   1800
tcgctcctca acccctcccc tccatccctg gccccctccc tggatgacat taaagaaggg   1860
ttgagctggt ccctgcctgc atgtgactgt aaatccctcc catgttttct ctgagtctcc   1920
ctttgcctgc tgaggctgta tgtgggctcc aggtaacagt gctgtcttcg ggccccctga   1980
actgtgttca tggagcatct ggctgggtag gcacatgctg ggcttgaatc caggggggac   2040
tgaatcctca gcttacggac ctgggcccat ctgtttctgg agggctccag tcttccttgt   2100
cctgtcttgg agtccccaag aaggaatcac aggggaggaa ccagatacca gccatgaccc   2160
caggctccac caagcatctt catgtccccc tgctcatccc ccactccccc ccacccagag   2220
ttgctcatcc tgccagggct ggctgtgccc accccaaggc tgccctcctg ggggccccag   2280
aactgcctga tcgtgccgtg gcccagtttt gtggcatctg cagcaacaca agagagagga   2340
caatgtcctc ctcttgaccc gctgtcacct aaccagactc gggccctgca cctctcaggc   2400
acttctggaa aatgactgag gcagattctt cctgaagccc attctccatg gggcaacaag   2460
gacacctatt ctgtccttgt ccttccatcg ctgccccaga aagcctcaca tatctccgtt   2520
tagaatcagg tcccttctcc ccagatgaag aggagggtct ctgctttgtt ttctctatct   2580
cctcctcaga cttgaccagg cccagcaggc cccagaagac cattacccta tatcccttct   2640
cctccctagt cacatggcca taggcctgct gatggctcag gaaggccatt gcaaggactc   2700
ctcagctatg ggagaggaag cacatcaccc attgaccccc gcaacccctc cctttcctcc   2760
tctgagtccc gactggggcc acatgcagcc tgacttcttt gtgcctgttg ctgtccctgc   2820
agtcttcaga gggccaccgc agctccagtg ccacggcagg aggctgttcc tgaatagccc   2880
ctgtggtaag ggccaggaga gtccttccat cctccaaggc cctgctaaag gacacagcag   2940
ccaggaagtc ccctgggccc ctagctgaag gacagcctgc tccctccgtc tctaccagga   3000
atggccttgt cctatggaag gcactgcccc atcccaaact aatctaggaa tcactgtcta   3060
accactcact gtcatgaatg tgtacttaaa ggatgaggtt gagtcatacc aaatagtgat   3120
ttcgatagtt caaaatggtg aaattagcaa ttctacatga ttcagtctaa tcaatggata   3180
ccgactgttt cccacacaag tctcctgttc tcttaagctt actcactgac agcctttcac   3240
tctccacaaa tacattaaag atatggccat caccaagccc cctaggatga caccagacct   3300
gagagtctga agacctggat ccaagttctg acttttcccc ctgacagctg tgtgaccttc   3360
gtgaagtcgc caaacctctc tgagccccag tcattgctag taagacctgc ctttgagttg   3420
gtatgatgtt caagttagat aacaaaatgt ttatacccat tagaacagag aataaataga   3480
actacatttc ttgca                                                    3495
```

<210> SEQ ID NO 8
<211> LENGTH: 3492
<212> TYPE: DNA
<213> ORGANISM: Homo sapiens

<400> SEQUENCE: 8

-continued

```
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggaggggc ggcaacctcc tgccagcctt caggccactc     180
tcctgtgcct gccagaagag acagagcttg aggagagctt gaggagagca ggaaagggcg     240
gcagtaagtc ttcagcatca ggcattttgg ggtgactcag taaatggtag atcttgctac     300
cagtggaaca gccactaagg attctgcagt gagagcagag ggccagctaa gtggtactct     360
cccagagact gtctgactca cgccaccccc tccaccttgg acacaggacg ctgtggtttc     420
tgagccagcc tcccccgttg cccctctgga tccactgctt aaatacggac gaggacaggg     480
ccctgtctcc tcagcttcag gcaccaccac tgacctggga cagtgaatcg acaatgccgt     540
cttctgtctc gtggggcatc ctcctgctgg caggcctgtg ctgcctggtc cctgtctccc     600
tggctgagga tccccaggga gatgctgccc agaagacaga tacatcccac catgatcagg     660
atcacccaac cttcaacaag atcacccccca acctggctga gttcgccttc agcctatacc     720
gccagctggc acaccagtcc aacagcacca atatcttctt ctccccagtg agcatcgcta     780
cagcctttgc aatgctctcc ctggggacca aggctgacac tcacgatgaa atcctggagg     840
gcctgaattt caacctcacg gagattccgg aggctcagat ccatgaaggc ttccaggaac     900
tcctccgtac cctcaaccag ccagacagcc agctccagct gaccaccggc aatggcctgt     960
tcctcagcga gggcctgaag ctagtggata agtttttgga ggatgttaaa aagttgtacc    1020
actcagaagc cttcactgtc aacttcgggg acaccgaaga ggccaagaaa cagatcaacg    1080
attacgtgga gaagggtact caagggaaaa ttgtggattt ggtcaaggag cttgacagag    1140
acacagtttt tgctctggtg aattacatct tctttaaagg caaatgggag agaccctttg    1200
aagtcaagga caccgaggaa gaggacttcc acgtggacca ggtgaccacc gtgaaggtgc    1260
ctatgatgaa gcgtttaggc atgtttaaca tccagcactg taagaagctg tccagctggg    1320
tgctgctgat gaaatacctg ggcaatgcca ccgccatctt cttcctgcct gatgagggga    1380
aactacagca cctggaaaat gaactcaccc acgatatcat caccaagttc ctggaaaatg    1440
aagacagaag gtctgccagc ttacatttac ccaaactgtc cattactgga acctatgatc    1500
tgaagagcgt cctgggtcaa ctgggcatca ctaaggtctt cagcaatggg gctgacctct    1560
ccggggtcac agaggaggca cccctgaagc tctccaaggc cgtgcataag gctgtgctga    1620
ccatcgacga gaaagggact gaagctgctg gggccatgtt tttagaggcc atacccatgt    1680
ctatcccccc cgaggtcaag ttcaacaaac cctttgtctt cttaatgatt gaacaaaata    1740
ccaagtctcc cctcttcatg ggaaaagtgg tgaatcccac ccaaaaataa ctgcctctcg    1800
ctcctcaacc cctcccctcc atccctggcc ccctccctgg atgacattaa agaagggttg    1860
agctggtccc tgcctgcatg tgactgtaaa tccctcccat gttttctctg agtctccctt    1920
tgcctgctga ggctgtatgt gggctccagg taacagtgct gtcttcgggc cccctgaact    1980
gtgttcatgg agcatctggc tgggtaggca catgctgggc ttgaatccag gggggactga    2040
atcctcagct tacggacctg ggcccatctg tttctggagg gctccagtct tccttgtcct    2100
gtcttggagt ccccaagaag gaatcacagg ggaggaacca gataccagcc atgaccccag    2160
gctccaccaa gcatcttcat gtccccctgc tcatcccca ctcccccccca cccagagttg    2220
ctcatcctgc cagggctggc tgtgcccacc ccaaggctgc cctcctgggg gccccagaac    2280
tgcctgatcg tgccgtggcc cagttttgtg gcatctgcag caacacaaga gagaggacaa    2340
tgtcctcctc ttgacccgct gtcacctaac cagactcggg ccctgcacct ctcaggcact    2400
```

```
tctggaaaat gactgaggca gattcttcct gaagcccatt ctccatgggg caacaaggac   2460
acctattctg tccttgtcct tccatcgctg ccccagaaag cctcacatat ctccgtttag   2520
aatcaggtcc cttctcccca gatgaagagg agggtctctg ctttgttttc tctatctcct   2580
cctcagactt gaccaggccc agcaggcccc agaagaccat taccctatat cccttctcct   2640
ccctagtcac atggccatag gcctgctgat ggctcaggaa ggccattgca aggactcctc   2700
agctatggga gaggaagcac atcacccatt gacccccgca acccctccct ttcctcctct   2760
gagtcccgac tggggccaca tgcagcctga cttctttgtg cctgttgctg tccctgcagt   2820
cttcagaggg ccaccgcagc tccagtgcca cggcaggagg ctgttcctga atagcccctg   2880
tggtaagggc caggagagtc cttccatcct ccaaggccct gctaaaggac acagcagcca   2940
ggaagtcccc tgggccccta gctgaaggac agcctgctcc ctccgtctct accaggaatg   3000
gccttgtcct atggaaggca ctgccccatc ccaaactaat ctaggaatca ctgtctaacc   3060
actcactgtc atgaatgtgt acttaaagga tgaggttgag tcataccaaa tagtgatttc   3120
gatagttcaa aatggtgaaa ttagcaattc tacatgattc agtctaatca atggataccg   3180
actgtttccc acacaagtct cctgttctct taagcttact cactgacagc ctttcactct   3240
ccacaaatac attaaagata tggccatcac caagcccccct aggatgacac cagacctgag   3300
agtctgaaga cctggatcca agttctgact tttcccccctg acagctgtgt gaccttcgtg   3360
aagtcgccaa acctctctga gccccagtca ttgctagtaa gacctgcctt tgagttggta   3420
tgatgttcaa gttagataac aaaatgttta tacccattag aacagagaat aaatagaact   3480
acatttcttg ca                                                       3492
```

<210> SEQ ID NO 9
<211> LENGTH: 3510
<212> TYPE: DNA
<213> ORGANISM: Homo sapiens

<400> SEQUENCE: 9

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaagggcg    240
gcagtaagtc ttcagcatca ggcattttgg ggtgactcag taaatggtag atcttgctac    300
cagtggaaca gccactaagg attctgcagt gagagcagag ggccagctaa gtggtactct    360
cccagagact gtctgactca cgccaccccc tccaccttgg acacaggacg ctgtggtttc    420
tgagccaggt acaatgactc ctttcgcctc ccccgttgcc cctctggatc cactgcttaa    480
atacggacga ggacagggcc ctgtctcctc agcttcaggc accaccactg acctgggaca    540
gtgaatcgac aatgccgtct tctgtctcgt ggggcatcct cctgctggca ggcctgtgct    600
gcctggtccc tgtctccctg gctgaggatc cccagggaga tgctgcccag aagacagata    660
catcccacca tgatcaggat cacccaacct tcaacaagat cacccccaac ctggctgagt    720
tcgccttcag cctataccgc cagctggcac accagtccaa cagcaccaat atcttcttct    780
ccccagtgag catcgctaca gcctttgcaa tgctctccct ggggaccaag gctgacactc    840
acgatgaaat cctggagggc ctgaatttca acctcacgga gattccggag gctcagatcc    900
atgaaggctt ccaggaactc ctccgtaccc tcaaccagcc agacagccag ctccagctga    960
```

-continued

```
ccaccggcaa tggcctgttc ctcagcgagg gcctgaagct agtggataag tttttggagg   1020
atgttaaaaa gttgtaccac tcagaagcct tcactgtcaa cttcggggac accgaagagg   1080
ccaagaaaca gatcaacgat tacgtggaga agggtactca agggaaaatt gtggatttgg   1140
tcaaggagct tgacagagac acagtttttg ctctggtgaa ttacatcttc tttaaaggca   1200
aatgggagag accctttgaa gtcaaggaca ccgaggaaga ggacttccac gtggaccagg   1260
tgaccaccgt gaaggtgcct atgatgaagc gtttaggcat gtttaacatc cagcactgta   1320
agaagctgtc cagctgggtg ctgctgatga aatacctggg caatgccacc gccatcttct   1380
tcctgcctga tgaggggaaa ctacagcacc tggaaaatga actcacccac gatatcatca   1440
ccaagttcct ggaaaatgaa gacagaaggt ctgccagctt acatttaccc aaactgtcca   1500
ttactggaac ctatgatctg aagagcgtcc tgggtcaact gggcatcact aaggtcttca   1560
gcaatggggc tgacctctcc ggggtcacag aggaggcacc cctgaagctc tccaaggccg   1620
tgcataaggc tgtgctgacc atcgacgaga aagggactga agctgctggg gccatgtttt   1680
tagaggccat acccatgtct atcccccccg aggtcaagtt caacaaaccc tttgtcttct   1740
taatgattga acaaaatacc aagtctcccc tcttcatggg aaaagtggtg aatcccaccc   1800
aaaaataact gcctctcgct cctcaacccc tcccctccat ccctggcccc ctccctggat   1860
gacattaaag aagggttgag ctggtccctg cctgcatgtg actgtaaatc cctcccatgt   1920
tttctctgag tctccctttg cctgctgagg ctgtatgtgg gctccaggta acagtgctgt   1980
cttcgggccc cctgaactgt gttcatggag catctggctg ggtaggcaca tgctgggctt   2040
gaatccaggg gggactgaat cctcagctta cggacctggg cccatctgtt tctggagggc   2100
tccagtcttc cttgtcctgt cttggagtcc ccaagaagga atcacagggg aggaaccaga   2160
taccagccat gaccccaggc tccaccaagc atcttcatgt ccccctgctc atcccccact   2220
ccccccacc cagagttgct catcctgcca gggctggctg tgcccacccc aaggctgccc   2280
tcctgggggc cccagaactg cctgatcgtg ccgtggccca gttttgtggc atctgcagca   2340
acacaagaga gaggacaatg tcctcctctt gacccgctgt cacctaacca gactcgggcc   2400
ctgcacctct caggcacttc tggaaaatga ctgaggcaga ttcttcctga agcccattct   2460
ccatggggca acaaggacac ctattctgtc cttgtccttc catcgctgcc ccagaaagcc   2520
tcacatatct ccgtttagaa tcaggtccct tctccccaga tgaagaggag ggtctctgct   2580
ttgttttctc tatctcctcc tcagacttga ccaggcccag caggccccag aagaccatta   2640
ccctatatcc cttctcctcc ctagtcacat ggccataggc ctgctgatgg ctcaggaagg   2700
ccattgcaag gactcctcag ctatgggaga ggaagcacat cacccattga cccccgcaac   2760
ccctcccttt cctcctctga gtcccgactg gggccacatg cagcctgact tctttgtgcc   2820
tgttgctgtc cctgcagtct tcagagggcc accgcagctc cagtgccacg gcaggaggct   2880
gttcctgaat agcccctgtg gtaagggcca ggagagtcct tccatcctcc aaggccctgc   2940
taaaggacac agcagccagg aagtcccctg ggcccctagc tgaaggacag cctgctccct   3000
ccgtctctac caggaatggc cttgtcctat ggaaggcact gccccatccc aaactaatct   3060
aggaatcact gtctaaccac tcactgtcat gaatgtgtac ttaaaggatg aggttgagtc   3120
ataccaaata gtgatttcga tagttcaaaa tggtgaaatt agcaattcta catgattcag   3180
tctaatcaat ggataccgac tgtttcccac acaagtctcc tgttctctta agcttactca   3240
ctgacagcct ttcactctcc acaaatacat taaagatatg gccatcacca agccccctag   3300
gatgacacca gacctgagag tctgaagacc tggatccaag ttctgacttt tccccctgac   3360
```

agctgtgtga ccttcgtgaa gtcgccaaac ctctctgagc cccagtcatt gctagtaaga 3420
cctgcctttg agttggtatg atgttcaagt tagataacaa aatgtttata cccattagaa 3480
cagagaataa atagaactac atttcttgca 3510

<210> SEQ ID NO 10
<211> LENGTH: 3303
<212> TYPE: DNA
<213> ORGANISM: Homo sapiens

<400> SEQUENCE: 10
tgggcaggaa ctgggcactg tgcccagggc atgcactgcc tccacgcagc aaccctcaga 60
gtcctgagct gaaccaagaa ggaggagggg gtcgggcctc cgaggaaggc ctagccgctg 120
ctgctgccag gaattccagg ttggaggggc ggcaacctcc tgccagcctt caggccactc 180
tcctgtgcct gccagaagag acagagcttg aggagagctt gaggagagca ggaaagcagc 240
ctcccccgtt gcccctctgg atccactgct taaatacgga cgaggacagg gccctgtctc 300
ctcagcttca ggcaccacca ctgacctggg acagtgaatc gacaatgccg tcttctgtct 360
cgtggggcat cctcctgctg gcaggcctgt gctgcctggt ccctgtctcc ctggctgagg 420
atccccaggg agatgctgcc cagaagacag atacatccca ccatgatcag gatcacccaa 480
ccttcaacaa gatcaccccc aacctggctg agttcgcctt cagcctatac cgccagctgg 540
cacaccagtc caacagcacc aatatcttct tctccccagt gagcatcgct acagcctttg 600
caatgctctc cctggggacc aaggctgaca ctcacgatga aatcctggag ggcctgaatt 660
tcaacctcac ggagattccg gaggctcaga tccatgaagg cttccaggaa ctcctccgta 720
ccctcaacca gccagacagc cagctccagc tgaccaccgg caatggcctg ttcctcagcg 780
agggcctgaa gctagtggat aagtttttgg aggatgttaa aaagttgtac cactcagaag 840
ccttcactgt caacttcggg gacaccgaag aggccaagaa acagatcaac gattacgtgg 900
agaagggtac tcaagggaaa attgtggatt tggtcaagga gcttgacaga gacacagttt 960
ttgctctggt gaattacatc ttctttaaag gcaaatggga gagacccttt gaagtcaagg 1020
acaccgagga agaggacttc cacgtggacc aggtgaccac cgtgaaggtg cctatgatga 1080
agcgtttagg catgtttaac atccagcact gtaagaagct gtccagctgg gtgctgctga 1140
tgaaatacct gggcaatgcc accgccatct tcttcctgcc tgatgagggg aaactacagc 1200
acctggaaaa tgaactcacc cacgatatca tcaccaagtt cctggaaaat gaagacagaa 1260
ggtctgccag cttacattta cccaaactgt ccattactgg aacctatgat ctgaagagcg 1320
tcctgggtca actgggcatc actaaggtct tcagcaatgg ggctgacctc tccggggtca 1380
cagaggaggc acccctgaag ctctccaagg ccgtgcataa ggctgtgctg accatcgacg 1440
agaaagggac tgaagctgct ggggccatgt ttttagaggc catacccatg tctatccccc 1500
ccgaggtcaa gttcaacaaa ccctttgtct tcttaatgat tgaacaaaat accaagtctc 1560
ccctcttcat gggaaaagtg gtgaatccca cccaaaaata actgcctctc gctcctcaac 1620
ccctcccctc catccctggc cccctccctg gatgacatta aagaagggtt gagctggtcc 1680
ctgcctgcat gtgactgtaa atccctccca tgttttctct gagtctccct ttgcctgctg 1740
aggctgtatg tgggctccag gtaacagtgc tgtcttcggg ccccctgaac tgtgttcatg 1800
gagcatctgg ctgggtaggc acatgctggg cttgaatcca gggggactg aatcctcagc 1860 ttacggacct gggcccatct gtttctggag ggctccagtc ttccttgtcc tgtcttggag 1920

```
tccccaagaa ggaatcacag gggaggaacc agataccagc catgacccca ggctccacca   1980
agcatcttca tgtccccctg ctcatccccc actccccccc acccagagtt gctcatcctg   2040
ccagggctgg ctgtgcccac cccaaggctg ccctcctggg ggccccagaa ctgcctgatc   2100
gtgccgtggc ccagttttgt ggcatctgca gcaacacaag agagaggaca atgtcctcct   2160
cttgacccgc tgtcacctaa ccagactcgg gccctgcacc tctcaggcac ttctggaaaa   2220
tgactgaggc agattcttcc tgaagcccat tctccatggg gcaacaagga cacctattct   2280
gtccttgtcc ttccatcgct gccccagaaa gcctcacata tctccgttta gaatcaggtc   2340
ccttctcccc agatgaagag gagggtctct gctttgtttt ctctatctcc tcctcagact   2400
tgaccaggcc cagcaggccc cagaagacca ttaccctata tcccttctcc tccctagtca   2460
catggccata ggcctgctga tggctcagga aggccattgc aaggactcct cagctatggg   2520
agaggaagca catcacccat tgacccccgc aacccctccc tttcctcctc tgagtcccga   2580
ctggggccac atgcagcctg acttctttgt gcctgttgct gtccctgcag tcttcagagg   2640
gccaccgcag ctccagtgcc acggcaggag gctgttcctg aatagcccct gtggtaaggg   2700
ccaggagagt ccttccatcc tccaaggccc tgctaaagga cacagcagcc aggaagtccc   2760
ctgggcccct agctgaagga cagcctgctc cctccgtctc taccaggaat ggccttgtcc   2820
tatggaaggc actgccccat cccaaactaa tctaggaatc actgtctaac cactcactgt   2880
catgaatgtg tacttaaagg atgaggttga gtcataccaa atagtgattt cgatagttca   2940
aaatggtgaa attagcaatt ctacatgatt cagtctaatc aatggatacc gactgtttcc   3000
cacacaagtc tcctgttctc ttaagcttac tcactgacag cctttcactc tccacaaata   3060
cattaaagat atggccatca ccaagccccc taggatgaca ccagacctga gagtctgaag   3120
acctggatcc aagttctgac ttttccccct gacagctgtg tgaccttcgt gaagtcgcca   3180
aacctctctg agccccagtc attgctagta agacctgcct ttgagttggt atgatgttca   3240
agttagataa caaaatgttt atacccatta gaacagagaa taaatagaac tacatttctt   3300
gca                                                                 3303
```

```
<210> SEQ ID NO 11
<211> LENGTH: 3300
<212> TYPE: DNA
<213> ORGANISM: Homo sapiens

<400> SEQUENCE: 11

tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaagcctc    240
ccccgttgcc cctctggatc cactgcttaa atacggacga ggacagggcc ctgtctcctc    300
agcttcaggc accaccactg acctgggaca gtgaatcgac aatgccgtct tctgtctcgt    360
ggggcatcct cctgctggca ggcctgtgct gcctggtccc tgtctccctg gctgaggatc    420
cccagggaga tgctgcccag aagacagata catcccacca tgatcaggat cacccaacct    480
tcaacaagat cacccccaac ctggctgagt tcgccttcag cctataccgc cagctggcac    540
accagtccaa cagcaccaat atcttcttct ccccagtgag catcgctaca gcctttgcaa    600
tgctctccct ggggaccaag gctgacactc acgatgaaat cctggagggc ctgaatttca    660
acctcacgga gattccggag gctcagatcc atgaaggctt ccaggaactc ctccgtaccc    720
```

-continued

```
tcaaccagcc agacagccag ctccagctga ccaccggcaa tggcctgttc ctcagcgagg    780
gcctgaagct agtggataag tttttggagg atgttaaaaa gttgtaccac tcagaagcct    840
tcactgtcaa cttcggggac accgaagagg ccaagaaaca gatcaacgat tacgtggaga    900
agggtactca agggaaaatt gtggatttgg tcaaggagct tgacagagac acagtttttg    960
ctctggtgaa ttacatcttc tttaaaggca aatgggagag accctttgaa gtcaaggaca   1020
ccgaggaaga ggacttccac gtggaccagg tgaccaccgt gaaggtgcct atgatgaagc   1080
gtttaggcat gtttaacatc cagcactgta agaagctgtc cagctgggtg ctgctgatga   1140
aatacctggg caatgccacc gccatcttct tcctgcctga tgaggggaaa ctacagcacc   1200
tggaaaatga actcacccac gatatcatca ccaagttcct ggaaaatgaa gacagaaggt   1260
ctgccagctt acatttaccc aaactgtcca ttactggaac ctatgatctg aagagcgtcc   1320
tgggtcaact gggcatcact aaggtcttca gcaatggggc tgacctctcc ggggtcacag   1380
aggaggcacc cctgaagctc tccaaggccg tgcataaggc tgtgctgacc atcgacgaga   1440
aagggactga agctgctggg gccatgtttt tagaggccat acccatgtct atcccccccg   1500
aggtcaagtt caacaaaccc tttgtcttct taatgattga acaaaatacc aagtctcccc   1560
tcttcatggg aaaagtggtg aatcccaccc aaaaataact gcctctcgct cctcaacccc   1620
tcccctccat ccctggcccc ctccctggat gacattaaag aagggttgag ctggtccctg   1680
cctgcatgtg actgtaaatc cctcccatgt tttctctgag tctccctttg cctgctgagg   1740
ctgtatgtgg gctccaggta acagtgctgt cttcgggccc cctgaactgt gttcatggag   1800
catctggctg ggtaggcaca tgctgggctt gaatccaggg gggactgaat cctcagctta   1860
cggacctggg cccatctgtt tctggagggc tccagtcttc cttgtcctgt cttggagtcc   1920
ccaagaagga atcacagggg aggaaccaga taccagccat gaccccaggc tccaccaagc   1980
atcttcatgt cccccctgctc atcccccact cccccccacc cagagttgct catcctgcca   2040
gggctggctg tgcccacccc aaggctgccc tcctgggggc cccagaactg cctgatcgtg   2100
ccgtggccca gttttgtggc atctgcagca acacaagaga gaggacaatg tcctcctctt   2160
gacccgctgt cacctaacca gactcgggcc ctgcacctct caggcacttc tggaaaatga   2220
ctgaggcaga ttcttcctga agcccattct ccatggggca acaaggacac ctattctgtc   2280
cttgtccttc catcgctgcc ccagaaagcc tcacatatct ccgtttagaa tcaggtccct   2340
tctccccaga tgaagaggag ggtctctgct ttgttttctc tatctcctcc tcagacttga   2400
ccaggcccag caggccccag aagaccatta ccctatatcc cttctcctcc ctagtcacat   2460
ggccataggc ctgctgatgg ctcaggaagg ccattgcaag gactcctcag ctatgggaga   2520
ggaagcacat cacccattga cccccgcaac ccctcccttt cctcctctga gtcccgactg   2580
gggccacatg cagcctgact tctttgtgcc tgttgctgtc cctgcagtct tcagagggcc   2640
accgcagctc cagtgccacg gcaggaggct gttcctgaat agcccctgtg gtaagggcca   2700
ggagagtcct tccatcctcc aaggccctgc taaaggacac agcagccagg aagtcccctg   2760
ggcccctagc tgaaggacag cctgctccct ccgtctctac caggaatggc cttgtcctat   2820
ggaaggcact gccccatccc aaactaatct aggaatcact gtctaaccac tcactgtcat   2880
gaatgtgtac ttaaaggatg aggttgagtc ataccaaata gtgatttcga tagttcaaaa   2940
tggtgaaatt agcaattcta catgattcag tctaatcaat ggataccgac tgtttcccac   3000
acaagtctcc tgttctctta agcttactca ctgacagcct ttcactctcc acaaatacat   3060
```

```
taaagatatg gccatcacca agccccctag gatgacacca gacctgagag tctgaagacc   3120

tggatccaag ttctgacttt tccccctgac agctgtgtga ccttcgtgaa gtcgccaaac   3180

ctctctgagc cccagtcatt gctagtaaga cctgcctttg agttggtatg atgttcaagt   3240

tagataacaa aatgtttata cccattagaa cagagaataa atagaactac atttcttgca   3300
```

<210> SEQ ID NO 12
<211> LENGTH: 1321
<212> TYPE: DNA
<213> ORGANISM: Macaca mulatta

<400> SEQUENCE: 12

```
caggacaatg ccatcttctg tctcatgggg cgtcctcctg ctggcaggcc tgtgctgcct     60

gctccccggc tctctggctg aggatcccca gggagatgct gcccagaaga cggatacatc    120

ccaccatgat caggaccacc caaccctcaa caagatcacc cccagcctgg ctgagttcgg    180

cttcagccta taccgccagc tggcacacca gtccaacagc accaatatct tcttctcccc    240

agtgagcatc gctacagcct ttgcaatgct ctccctgggg accaaggctg acactcacag    300

tgaaatcctg gagggcctga atttcaacgt cacggagatt ccggaggctc aggtccatga    360

aggcttccag gaactcctcc ataccctcaa caagccagac agccagctcc agctgaccac    420

cggcaacggc ctgttcctca acaagagcct gaaggtagtg gataagtttt tggaggatgt    480

caaaaaactg taccactcag aagccttctc tgtcaacttt gaggacaccg aagaggccaa    540

gaaacagatc aacaattacg tggagaagga aactcaaggg aaaattgtgg atttggtcaa    600

ggagcttgac agagacacag tttttgctct ggtgaattac atcttcttta aaggcaaatg    660

ggagagaccc tttgacgttg aggccaccaa ggaagaggac ttccacgtgg accaggcgac    720

caccgtgaag gtgcccatga tgaggcgttt aggcatgttt aacatctacc actgtgagaa    780

gctgtccagc tgggtgctgc tgatgaaata cctgggcaat gccaccgcca tcttcttcct    840

gcctgatgag gggaaactgc agcacctgga aaatgaactc acccatgata tcatcaccaa    900

gttcctggaa aatgaaaaca gcaggtctgc caacttacat ttacccagac tggccattac    960

tggaacctat gatctgaaga cagtcctggg ccacctgggt atcactaagg tcttcagcaa   1020

tggggctgac ctctcgggga tcacggagga ggcacccctg aagctctcca aggccgtgca   1080

taaggctgtg ctgaccatcg atgagaaagg gactgaagct gctggggcca tgtttttaga   1140

ggccataccc atgtctattc cccccgaggt caagttcaac aaaccctttg tcttcttaat   1200

gattgaacaa aataccaagt ctcccctctt catgggaaaa gtggtgaatc ccacccagaa   1260

ataactgcct gtcactcctc agcccctccc ctccatccct ggccccctcc ctgaatgaca   1320

t                                                                   1321
```

<210> SEQ ID NO 13
<211> LENGTH: 2064
<212> TYPE: DNA
<213> ORGANISM: Macaca mulatta

<400> SEQUENCE: 13

```
gcccagtctt gtgtctgcct ggcaatgggc aaggcccctt cctgcccaag ctccccgccc     60

ctccccaacc tattgcctcc gccacccgcc acccgaggcc aacttcctgg gtgggcagga    120

actgggccct gtgcccaggg cgtgcactgc ctccacgcag caaccctcag agtactgagc    180

tgagcaaagg aggaggaggg gatcagcact ctgaggaagg cctagccact gctgctgcca    240

ggaattccag ggcggcatca gtcttcagca tcaggcattt cggggtgaat tagtaaatgg    300
```

tagatcttgc taccagtgga acagccgcta aggattctgc agtgagagca gagggccagc 360
aaagtggtac tctcccagcg actggctgac tcacgccacc ccctccacct tggacgcagg 420
acactgtggt ttctgagcca ggtacaatga ctccttttgg tacgtgcagt ggaggctgta 480
tgctgctcag gcagagcgtc cggacagcgt gggcgggcga ctcagcgccc agcctgtgaa 540
cttagtccct gtttgctcct ccggtaactg ggtgatctt ggttaatatt caccagcagc 600
ctcccccgtt gcccctctgc acccactgct taaatacgga caaggacagg gctctgtctc 660
ctcagcctca ggcaccacca ctgacctggg acggtgaatc gacaatgcca tcttctgtct 720
catggggcgt cctcctgctg gcaggcctgt gctgcctgct ccccggctct ctggctgagg 780
atccccaggg agatgctgcc cagaagacgg atacatccca ccatgatcag gaccacccaa 840
ccctcaacaa gatcaccccc agcctggctg agttcggctt cagcctatac cgccagctgg 900
cacaccagtc caacagcacc aatatcttct tctccccagt gagcatcgct acagcctttg 960
caatgctctc cctggggacc aaggctgaca ctcacagtga aatcctggag ggcctgaatt 1020
tcaacgtcac ggagattccg gaggctcagg tccatgaagg cttccaggaa ctcctccata 1080
ccctcaacaa gccagacagc cagctccagc tgaccaccgg caacggcctg ttcctcaaca 1140
agagcctgaa ggtagtggat aagtttttgg aggatgtcaa aaaactgtac cactcagaag 1200
ccttctctgt caactttgag gacaccgaag aggccaagaa acagatcaac aattacgtgg 1260
agaaggaaac tcaagggaaa attgtggatt tggtcaagga gcttgacaga gacacagttt 1320
ttgctctggt gaattacatc ttctttaaag gcaaatggga gagacccttt gacgttgagg 1380
ccaccaagga agaggacttc cacgtggacc aggcgaccac cgtgaaggtg cccatgatga 1440
ggcgtttagg catgtttaac atctaccact gtgagaagct gtccagctgg gtgctgctga 1500
tgaaatacct gggcaatgcc accgccatct tcttcctgcc tgatgagggg aaactgcagc 1560
acctggaaaa tgaactcacc catgatatca tcaccaagtt cctggaaaat gaaaacagca 1620
ggtctgccaa cttacattta cccagactgg ccattactgg aacctatgat ctgaagacag 1680
tcctgggcca cctgggtatc actaaggtct tcagcaatgg ggctgacctc tcggggatca 1740
cggaggaggc acccctgaag ctctccaagg ccgtgcataa ggctgtgctg accatcgatg 1800
agaaagggac tgaagctgct ggggccatgt ttttagaggc catacccatg tctattcccc 1860
ccgaggtcaa gttcaacaaa ccctttgtct tcttaatgat tgaacaaaat accaagtctc 1920
ccctcttcat gggaaaagtg gtgaatccca cccagaaata actgcctgtc actcctcagc 1980
ccctcccctc catccctggc cccctccctg aatgacatta aagaagggtt gagctggtcc 2040
ctgcctgcgt gtgtgactgc aaac 2064

<210> SEQ ID NO 14
<211> LENGTH: 1608
<212> TYPE: DNA
<213> ORGANISM: Macaca mulatta

<400> SEQUENCE: 14
tcttgtgtct gcctggcaat gggcaaggcc ccttcctgcc caagctcccc gcccctcccc 60
aacctattgc ctccgccacc cgccacccga ggccaacttc ctgggtgggc aggaactggg 120
ccctgtgccc agggcgtgca ctgcctccac gcagcaaccc tcagagtact gagctgagca 180
aaggaggagg aggggatcag cactctgagg aaggcctagc cactgctgct gccaggaatt 240
ccaggacaat gccatcttct gtctcatggg gcgtcctcct gctggcaggc ctgtgctgcc 300
tgctccccgg ctctctggct gaggatcccc agggagatgc tgcccagaag acggatacat 360
cccaccatga tcaggaccac ccaaccctca acaagatcac ccccagcctg gctgagttcg 420
gcttcagcct ataccgccag ctggcacacc agtccaacag caccaatatc ttcttctccc 480
cagtgagcat cgctacagcc tttgcaatgc tctccctggg gaccaaggct gacactcaca 540
gtgaaatcct ggagggcctg aatttcaacg tcacggagat tccggaggct caggtccatg 600
aaggcttcca ggaactcctc cataccctca acaagccaga cagccagctc cagctgacca 660
ccggcaacgg cctgttcctc aacaagagcc tgaaggtagt ggataagttt ttggaggatg 720
tcaaaaaact gtaccactca gaagccttct ctgtcaactt tgaggacacc gaagaggcca 780
agaaacagat caacaattac gtggagaagg aaactcaagg gaaaattgtg gatttggtca 840
aggagcttga cagagacaca gtttttgctc tggtgaatta catcttcttt aaaggcaaat 900
gggagagacc ctttgacgtt gaggccacca aggaagagga cttccacgtg gaccaggcga 960
ccaccgtgaa ggtgcccatg atgaggcgtt taggcatgtt taacatctac cactgtgaga 1020
agctgtccag ctgggtgctg ctgatgaaat acctgggcaa tgccaccgcc atcttcttcc 1080
tgcctgatga ggggaaactg cagcacctgg aaaatgaact cacccatgat atcatcacca 1140
agttcctgga aaatgaaaac agcaggtctg ccaacttaca tttacccaga ctggccatta 1200
ctggaaccta tgatctgaag acagtcctgg gccacctggg tatcactaag gtcttcagca 1260
atggggctga cctctcgggg atcacggagg aggcacccct gaagctctcc aaggccgtgc 1320
ataaggctgt gctgaccatc gatgagaaag ggactgaagc tgctggggcc atgtttttag 1380
aggccatacc catgtctatt ccccccgagg tcaagttcaa caaacccttt gtcttcttaa 1440
tgattgaaca aaataccaag tctcccctct tcatgggaaa agtggtgaat cccacccaga 1500
aataactgcc tgtcactcct cagcccctcc cctccatccc tggcccccctc cctgaatgac 1560 attaaagaag ggttgagctg gtccctgcct gcgtgtgtga ctgcaaac 1608

<210> SEQ ID NO 15
<211> LENGTH: 3220
<212> TYPE: DNA
<213> ORGANISM: Homo sapiens

<400> SEQUENCE: 15
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcagggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840

```
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag gggg ccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt    1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctgctg gtgaatatta accaaggtca ccccagttat cggaggagca aacaggggct   3120
aagtccactg gctgggatct gagtcgcccg cctacgctgc ccggacgctt tgcctgggca   3180
```

-continued gtgtacagct tccactgcac ttaccgaaag gagtcattgt 3220

<210> SEQ ID NO 16
<211> LENGTH: 3199
<212> TYPE: DNA
<213> ORGANISM: Homo sapiens

<400> SEQUENCE: 16
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcaggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840
atgtgactag ggaggagaag ggatataggg taatggtctt ctggggcctg ctgggcctgg 900
tcaagtctga ggaggagata gagaaaacaa agcagagacc ctcctcttca tctggggaga 960
agggacctga ttctaaacgg agatatgtga ggctttctgg ggcagcgatg gaaggacaag 1020
gacagaatag gtgtccttgt tgccccatgg agaatgggct tcaggaagaa tctgcctcag 1080
tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800 cggggggg at agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcctttcct gctctcctca agctctcctc aagctctgtc 3000
tcttctggca ggcacaggag agtggcctga aggctggcag gaggttgccg cccctccaac 3060
ctggaattcc tggcagcagc agcggctagg ccttcctcgg aggcccgacc ccctcctcct 3120
tcttggttca gctcaggact ctgagggttg ctgcgtggag gcagtgcatg ccctgggcac 3180
agtgcccagt tcctgccca 3199

<210> SEQ ID NO 17
<211> LENGTH: 3513
<212> TYPE: DNA
<213> ORGANISM: Homo sapiens

<400> SEQUENCE: 17
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcagggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840
atgtgactag ggaggagaag ggatataggg taatggtctt ctggggcctg ctgggcctgg 900
tcaagtctga ggaggagata gagaaaacaa agcagagacc ctcctcttca tctggggaga 960

-continued

```
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctgcga aaggagtcat tgtacctggc tcagaaacca cagcgtcctg tgtccaaggt   3120
ggagggggtg gcgtgagtca gacagtctct gggagagtac cacttagctg gccctctgct   3180
ctcactgcag aatccttagt ggctgttcca ctggtagcaa gatctaccat ttactgagtc   3240
accccaaaat gcctgatgct gaagacttac tgccgccctt tcctgctctc ctcaagctct   3300
cctcaagctc tgtctcttct ggcaggcaca ggagagtggc ctgaaggctg gcaggaggtt   3360
```

gccgcccctc caacctggaa ttcctggcag cagcagcggc taggccttcc tcggaggccc 3420
gaccccctcc tccttcttgg ttcagctcag gactctgagg gttgctgcgt ggaggcagtg 3480
catgccctgg gcacagtgcc cagttcctgc cca 3513

<210> SEQ ID NO 18
<211> LENGTH: 3236
<212> TYPE: DNA
<213> ORGANISM: Homo sapiens

<400> SEQUENCE: 18
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcaggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840
atgtgactag ggaggagaag ggatataggg taatggtctt ctggggcctg ctgggcctgg 900
tcaagtctga ggaggagata gagaaaacaa agcagagacc ctcctcttca tctggggaga 960
agggacctga ttctaaacgg agatatgtga ggctttctgg ggcagcgatg gaaggacaag 1020
gacagaatag gtgtccttgt tgccccatgg agaatgggct tcaggaagaa tctgcctcag 1080
tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800 cggggggga t agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcctgtgga actgagtgag cagcagcagc aatgtcccac 3000
ctttcctgct ctcctcaagc tctcctcaag ctctgtctct tctggcaggc acaggagagt 3060
ggcctgaagg ctggcaggag gttgccgccc ctccaacctg gaattcctgg cagcagcagc 3120
ggctaggcct tcctcggagg cccgaccccc tcctccttct tggttcagct caggactctg 3180
agggttgctg cgtggaggca gtgcatgccc tgggcacagt gcccagttcc tgccca 3236

<210> SEQ ID NO 19
<211> LENGTH: 3532
<212> TYPE: DNA
<213> ORGANISM: Homo sapiens

<400> SEQUENCE: 19
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcagggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840

-continued atgtgactag ggaggagaag ggatataggg taatggtctt ctggggcctg ctgggcctgg 900
tcaagtctga ggaggagata gagaaaacaa agcagagacc ctcctcttca tctggggaga 960
agggacctga ttctaaacgg agatatgtga ggctttctgg ggcagcgatg gaaggacaag 1020
gacagaatag gtgtccttgt tgccccatgg agaatgggct tcaggaagaa tctgcctcag 1080
tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800 cggggggat agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggctgctg gctcagaaac cacagcgtcc tgtgtccaag gtggaggggg tggcgtgagt 3120
cagacagtct ctgggagagt accacttagc tggccctctg ctctcactgc agaatcctta 3180

```
gtggctgttc cactggtagc aagatctacc atttactgag tcaccccaaa atgcctgatg   3240
ctgaagactt actgccgccc tgtggaactg agtgagcagc agcagcaatg tcccaccttt   3300
cctgctctcc tcaagctctc ctcaagctct gtctcttctg gcaggcacag gagagtggcc   3360
tgaaggctgg caggaggttg ccgcccctcc aacctggaat tcctggcagc agcagcggct   3420
aggccttcct cggaggcccg accccctcct ccttcttggt tcagctcagg actctgaggg   3480
ttgctgcgtg gaggcagtgc atgccctggg cacagtgccc agttcctgcc ca           3532
```

<210> SEQ ID NO 20
<211> LENGTH: 3340
<212> TYPE: DNA
<213> ORGANISM: Homo sapiens

<400> SEQUENCE: 20

```
tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcaggggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
```

-continued

```
cgggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctgctg tggaactgag tgagcagcag cagcaatgtc ccacctttcc tgctctcctc   3120
aagctctcct caagctctgt ctcttctggc aggcacagga gagtggcctg aaggctggca   3180
ggaggttgcc gcccctccaa cctggaattc ctggcagcag cagcggctag gccttcctcg   3240
gaggcccgac cccctcctcc ttcttggttc agctcaggac tctgagggtt gctgcgtgga   3300
ggcagtgcat gccctgggca cagtgcccag ttcctgccca                         3340
```

<210> SEQ ID NO 21
<211> LENGTH: 3495
<212> TYPE: DNA
<213> ORGANISM: Homo sapiens

<400> SEQUENCE: 21

```
tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcaggggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
```

-continued

```
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
```

-continued acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggctgctg gctcagaaac cacagcgtcc tgtgtccaag gtggaggggg tggcgtgagt 3120
cagacagtct ctgggagagt accacttagc tggccctctg ctctcactgc agaatcctta 3180
gtggctgttc cactggtagc aagatctacc atttactgag tcaccccaaa atgcctgatg 3240
ctgaagactt actgccgccc tttcctgctc tcctcaagct ctcctcaagc tctgtctctt 3300
ctggcaggca caggagagtg gcctgaaggc tggcaggagg ttgccgcccc tccaacctgg 3360
aattcctggc agcagcagcg gctaggcctt cctcggaggc ccgacccccct cctccttctt 3420 ggttcagctc aggactctga gggttgctgc gtggaggcag tgcatgccct gggcacagtg 3480
cccagttcct gccca 3495

<210> SEQ ID NO 22
<211> LENGTH: 3492
<212> TYPE: DNA
<213> ORGANISM: Homo sapiens

<400> SEQUENCE: 22
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcagggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840
atgtgactag ggaggagaag ggatataggg taatggtctt ctggggcctg ctgggcctgg 900
tcaagtctga ggaggagata gagaaaacaa agcagagacc ctcctcttca tctggggaga 960
agggacctga ttctaaacgg agatatgtga ggctttctgg ggcagcgatg gaaggacaag 1020
gacagaatag gtgtccttgt tgccccatgg agaatgggct tcaggaagaa tctgcctcag 1080
tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800 cggggggat agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggctggct cagaaaccac agcgtcctgt gtccaaggtg gagggggtgg cgtgagtcag 3120
acagtctctg ggagagtacc acttagctgg ccctctgctc tcactgcaga atccttagtg 3180
gctgttccac tggtagcaag atctaccatt tactgagtca ccccaaaatg cctgatgctg 3240
aagacttact gccgcccttt cctgctctcc tcaagctctc ctcaagctct gtctcttctg 3300
gcaggcacag gagagtggcc tgaaggctgg caggaggttg ccgcccctcc aacctggaat 3360
tcctggcagc agcagcggct aggccttcct cggaggcccg acccccctcct ccttcttggt 3420 tcagctcagg actctgaggg ttgctgcgtg gaggcagtgc atgccctggg cacagtgccc 3480
agttcctgcc ca 3492

<210> SEQ ID NO 23
<211> LENGTH: 3510
<212> TYPE: DNA
<213> ORGANISM: Homo sapiens

<400> SEQUENCE: 23
tgcaagaaat gtagttctat ttattctctg ttctaatggg tataaacatt ttgttatcta 60
acttgaacat cataccaact caaaggcagg tcttactagc aatgactggg gctcagagag 120

```
gtttggcgac ttcacgaagg tcacacagct gtcaggggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cggggggat agacatgggt atggcctcta aaaacatggc cccagcagct tcagtccctt    1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcatttcc aggaacttgg tgatgatatc gtgggtgagt tcattttcca    2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
```

```
aggcttctga gtggtacaac tttttaacat cctccaaaaa cttatccact agcttcaggc   2520

cctcgctgag gaacaggcca ttgccggtgg tcagctggag ctggctgtct ggctggttga   2580

gggtacggag gagttcctgg aagccttcat ggatctgagc ctccggaatc tccgtgaggt   2640

tgaaattcag gccctccagg atttcatcgt gagtgtcagc cttggtcccc agggagagca   2700

ttgcaaaggc tgtagcgatg ctcactgggg agaagaagat attggtgctg ttggactggt   2760

gtgccagctg gcggtatagg ctgaaggcga actcagccag gttgggggtg atcttgttga   2820

aggttgggtg atcctgatca tggtgggatg tatctgtctt ctgggcagca tctccctggg   2880

gatcctcagc cagggagaca gggaccaggc agcacaggcc tgccagcagg aggatgcccc   2940

acgagacaga agacggcatt gtcgattcac tgtcccaggt cagtggtggt gcctgaagct   3000

gaggagacag ggccctgtcc tcgtccgtat ttaagcagtg gatccagagg ggcaacgggg   3060

gaggcgaaag gagtcattgt acctggctca gaaaccacag cgtcctgtgt ccaaggtgga   3120

gggggtggcg tgagtcagac agtctctggg agagtaccac ttagctggcc ctctgctctc   3180

actgcagaat ccttagtggc tgttccactg gtagcaagat ctaccattta ctgagtcacc   3240

ccaaaatgcc tgatgctgaa gacttactgc cgccctttcc tgctctcctc aagctctcct   3300

caagctctgt ctcttctggc aggcacagga gagtggcctg aaggctggca ggaggttgcc   3360

gcccctccaa cctggaattc ctggcagcag cagcggctag gccttcctcg gaggcccgac   3420

cccctcctcc ttcttggttc agctcaggac tctgagggtt gctgcgtgga ggcagtgcat   3480

gccctgggca cagtgcccag ttcctgccca                                    3510
```

<210> SEQ ID NO 24
<211> LENGTH: 3303
<212> TYPE: DNA
<213> ORGANISM: Homo sapiens

<400> SEQUENCE: 24

```
tgcaagaaat gtagttctat ttattctctg ttctaatggg tataaacatt ttgttatcta     60

acttgaacat cataccaact caaaggcagg tcttactagc aatgactggg gctcagagag    120

gtttggcgac ttcacgaagg tcacacagct gtcaggggga aaagtcagaa cttggatcca    180

ggtcttcaga ctctcaggtc tggtgtcatc ctagggggct tggtgatggc catatcttta    240

atgtatttgt ggagagtgaa aggctgtcag tgagtaagct taagagaaca ggagacttgt    300

gtgggaaaca gtcggtatcc attgattaga ctgaatcatg tagaattgct aatttcacca    360

ttttgaacta tcgaaatcac tatttggtat gactcaacct catcctttaa gtacacattc    420

atgacagtga gtggttagac agtgattcct agattagttt gggatggggc agtgccttcc    480

ataggacaag gccattcctg gtagagacgg agggagcagg ctgtccttca gctaggggcc    540

caggggactt cctggctgct gtgtccttta gcagggcctt ggaggatgga aggactctcc    600

tggcccttac cacaggggct attcaggaac agcctcctgc cgtggcactg gagctgcggt    660

ggccctctga agactgcagg gacagcaaca ggcacaaaga agtcaggctg catgtggccc    720

cagtcgggac tcagaggagg aaagggaggg gttgcggggg tcaatgggtg atgtgcttcc    780

tctcccatag ctgaggagtc cttgcaatgg ccttcctgag ccatcagcag gcctatggcc    840

atgtgactag ggaggagaag ggatataggg taatggtctt ctggggcctg ctgggcctgg    900

tcaagtctga ggaggagata gagaaaacaa agcagagacc ctcctcttca tctggggaga    960

agggacctga ttctaaacgg agatatgtga ggctttctgg ggcagcgatg gaaggacaag   1020

gacagaatag gtgtccttgt tgccccatgg agaatgggct tcaggaagaa tctgcctcag   1080
```

tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800
cggggggggat agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggctgctt tcctgctctc ctcaagctct cctcaagctc tgtctcttct ggcaggcaca 3120
ggagagtggc ctgaaggctg gcaggaggtt gccgcccctc caacctggaa ttcctggcag 3180
cagcagcggc taggccttcc tcggaggccc gaccccctcc tccttcttgg ttcagctcag 3240
gactctgagg gttgctgcgt ggaggcagtg catgccctgg gcacagtgcc cagttcctgc 3300
cca 3303

<210> SEQ ID NO 25

<211> LENGTH: 3300
<212> TYPE: DNA
<213> ORGANISM: Homo sapiens

<400> SEQUENCE: 25
tgcaagaaat gtagttctat ttattctctg ttctaatggg tataaacatt ttgttatcta 60
acttgaacat cataccaact caaaggcagg tcttactagc aatgactggg gctcagagag 120
gtttggcgac ttcacgaagg tcacacagct gtcaggggga aaagtcagaa cttggatcca 180
ggtcttcaga ctctcaggtc tggtgtcatc ctagggggct tggtgatggc catatcttta 240
atgtatttgt ggagagtgaa aggctgtcag tgagtaagct taagagaaca ggagacttgt 300
gtgggaaaca gtcggtatcc attgattaga ctgaatcatg tagaattgct aatttcacca 360
ttttgaacta tcgaaatcac tatttggtat gactcaacct catcctttaa gtacacattc 420
atgacagtga gtggttagac agtgattcct agattagttt gggatggggc agtgccttcc 480
ataggacaag gccattcctg gtagagacgg agggagcagg ctgtccttca gctaggggcc 540
caggggactt cctggctgct gtgtccttta gcagggcctt ggaggatgga aggactctcc 600
tggcccttac cacaggggct attcaggaac agcctcctgc cgtggcactg gagctgcggt 660
ggccctctga agactgcagg gacagcaaca ggcacaaaga agtcaggctg catgtggccc 720
cagtcgggac tcagaggagg aaagggaggg gttgcggggg tcaatgggtg atgtgcttcc 780
tctcccatag ctgaggagtc cttgcaatgg ccttcctgag ccatcagcag gcctatggcc 840
atgtgactag ggaggagaag ggatataggg taatggtctt ctggggcctg ctgggcctgg 900
tcaagtctga ggaggagata gagaaaacaa agcagagacc ctcctcttca tctggggaga 960
agggacctga ttctaaacgg agatatgtga ggctttctgg ggcagcgatg gaaggacaag 1020
gacagaatag gtgtccttgt tgccccatgg agaatgggct tcaggaagaa tctgcctcag 1080
tcattttcca gaagtgcctg agaggtgcag ggcccgagtc tggttaggtg acagcgggtc 1140
aagaggagga cattgtcctc tctcttgtgt tgctgcagat gccacaaaac tgggccacgg 1200
cacgatcagg cagttctggg gcccccagga gggcagcctt ggggtgggca cagccagccc 1260
tggcaggatg agcaactctg ggtggggggg agtgggggat gagcaggggg acatgaagat 1320
gcttggtgga gcctggggtc atggctggta tctggttcct cccctgtgat tccttcttgg 1380
ggactccaag acaggacaag gaagactgga gccctccaga aacagatggg cccaggtccg 1440
taagctgagg attcagtccc ccctggattc aagcccagca tgtgcctacc cagccagatg 1500
ctccatgaac acagttcagg gggcccgaag acagcactgt tacctggagc ccacatacag 1560
cctcagcagg caaagggaga ctcagagaaa acatgggagg gatttacagt cacatgcagg 1620
cagggaccag ctcaaccctt ctttaatgtc atccagggag ggggccaggg atggagggga 1680
ggggttgagg agcgagaggc agttattttt gggtgggatt caccactttt cccatgaaga 1740
ggggagactt ggtattttgt tcaatcatta agaagacaaa gggtttgttg aacttgacct 1800
cgggggggat agacatgggt atggcctcta aaaacatggc cccagcagct tcagtccctt 1860
tctcgtcgat ggtcagcaca gccttatgca cggccttgga gagcttcagg ggtgcctcct 1920
ctgtgacccc ggagaggtca gccccattgc tgaagacctt agtgatgccc agttgaccca 1980
ggacgctctt cagatcatag gttccagtaa tggacagttt gggtaaatgt aagctggcag 2040
accttctgtc ttcattttcc aggaacttgg tgatgatatc gtgggtgagt tcattttcca 2100
ggtgctgtag tttcccctca tcaggcagga agaagatggc ggtggcattg cccaggtatt 2160
tcatcagcag cacccagctg gacagcttct tacagtgctg gatgttaaac atgcctaaac 2220
gcttcatcat aggcaccttc acggtggtca cctggtccac gtggaagtcc tcttcctcgg 2280
tgtccttgac ttcaaagggt ctctcccatt tgcctttaaa gaagatgtaa ttcaccagag 2340
caaaaactgt gtctctgtca agctccttga ccaaatccac aattttccct tgagtaccct 2400
tctccacgta atcgttgatc tgtttcttgg cctcttcggt gtccccgaag ttgacagtga 2460
aggcttctga gtggtacaac tttttaacat cctccaaaaa cttatccact agcttcaggc 2520
cctcgctgag gaacaggcca ttgccggtgg tcagctggag ctggctgtct ggctggttga 2580
gggtacggag gagttcctgg aagccttcat ggatctgagc ctccggaatc tccgtgaggt 2640
tgaaattcag gccctccagg atttcatcgt gagtgtcagc cttggtcccc agggagagca 2700
ttgcaaaggc tgtagcgatg ctcactgggg agaagaagat attggtgctg ttggactggt 2760
gtgccagctg gcggtatagg ctgaaggcga actcagccag gttgggggtg atcttgttga 2820
aggttgggtg atcctgatca tggtgggatg tatctgtctt ctgggcagca tctccctggg 2880
gatcctcagc cagggagaca gggaccaggc agcacaggcc tgccagcagg aggatgcccc 2940
acgagacaga agacggcatt gtcgattcac tgtcccaggt cagtggtggt gcctgaagct 3000
gaggagacag ggccctgtcc tcgtccgtat ttaagcagtg gatccagagg ggcaacgggg 3060
gaggctttcc tgctctcctc aagctctcct caagctctgt ctcttctggc aggcacagga 3120
gagtggcctg aaggctggca ggaggttgcc gcccctccaa cctggaattc ctggcagcag 3180
cagcggctag gccttcctcg gaggcccgac cccctcctcc ttcttggttc agctcaggac 3240
tctgagggtt gctgcgtgga ggcagtgcat gccctgggca cagtgcccag ttcctgccca 3300

<210> SEQ ID NO 26
<211> LENGTH: 1321
<212> TYPE: DNA
<213> ORGANISM: Macaca mulatta

<400> SEQUENCE: 26
atgtcattca gggagggggc cagggatgga ggggaggggc tgaggagtga caggcagtta 60
tttctgggtg ggattcacca cttttcccat gaagagggga gacttggtat tttgttcaat 120
cattaagaag acaaagggtt tgttgaactt gacctcgggg ggaatagaca tgggtatggc 180
ctctaaaaac atggccccag cagcttcagt ccctttctca tcgatggtca gcacagcctt 240
atgcacggcc ttggagagct tcaggggtgc ctcctccgtg atccccgaga ggtcagcccc 300
attgctgaag accttagtga tacccaggtg gcccaggact gtcttcagat cataggttcc 360
agtaatggcc agtctgggta aatgtaagtt ggcagacctg ctgttttcat tttccaggaa 420
cttggtgatg atatcatggg tgagttcatt ttccaggtgc tgcagtttcc cctcatcagg 480
caggaagaag atggcggtgg cattgcccag gtatttcatc agcagcaccc agctggacag 540
cttctcacag tggtagatgt taaacatgcc taaacgcctc atcatgggca ccttcacggt 600
ggtcgcctgg tccacgtgga agtcctcttc cttggtggcc tcaacgtcaa agggtctctc 660
ccatttgcct ttaaagaaga tgtaattcac cagagcaaaa actgtgtctc tgtcaagctc 720
cttgaccaaa tccacaattt tcccttgagt ttccttctcc acgtaattgt tgatctgttt 780
cttggcctct tcggtgtcct caaagttgac agagaaggct tctgagtggt acagtttttt 840
gacatcctcc aaaaacttat ccactacctt caggctcttg ttgaggaaca ggccgttgcc 900
ggtggtcagc tggagctggc tgtctggctt gttgagggta tggaggagtt cctggaagcc 960
ttcatggacc tgagcctccg gaatctccgt gacgttgaaa ttcaggccct ccaggatttc 1020

-continued

```
actgtgagtg tcagccttgg tccccaggga gagcattgca aaggctgtag cgatgctcac   1080

tggggagaag aagatattgg tgctgttgga ctggtgtgcc agctggcggt ataggctgaa   1140

gccgaactca gccaggctgg gggtgatctt gttgagggtt gggtggtcct gatcatggtg   1200

ggatgtatcc gtcttctggg cagcatctcc ctggggatcc tcagccagag agccggggag   1260

caggcagcac aggcctgcca gcaggaggac gccccatgag acagaagatg gcattgtcct   1320

g                                                                   1321
```

<210> SEQ ID NO 27
<211> LENGTH: 2064
<212> TYPE: DNA
<213> ORGANISM: Macaca mulatta

<400> SEQUENCE: 27

```
gtttgcagtc acacacgcag gcagggacca gctcaaccct tctttaatgt cattcaggga     60

gggggccagg gatggagggg aggggctgag gagtgacagg cagttatttc tgggtgggat    120

tcaccacttt tcccatgaag aggggagact tggtattttg ttcaatcatt aagaagacaa    180

agggtttgtt gaacttgacc tcggggggaa tagacatggg tatggcctct aaaaacatgg    240

ccccagcagc ttcagtccct ttctcatcga tggtcagcac agccttatgc acggccttgg    300

agagcttcag ggtgcctcc tccgtgatcc ccgagaggtc agccccattg ctgaagacct    360

tagtgatacc caggtggccc aggactgtct tcagatcata ggttccagta atggccagtc    420

tgggtaaatg taagttggca gacctgctgt tttcattttc caggaacttg gtgatgatat    480

catgggtgag ttcattttcc aggtgctgca gtttcccctc atcaggcagg aagaagatgg    540

cggtggcatt gcccaggtat ttcatcagca gcacccagct ggacagcttc tcacagtggt    600

agatgttaaa catgcctaaa cgcctcatca tgggcacctt cacggtggtc gcctggtcca    660

cgtggaagtc ctcttccttg gtggcctcaa cgtcaaaggg tctctcccat ttgcctttaa    720

agaagatgta attcaccaga gcaaaaactg tgtctctgtc aagctccttg accaaatcca    780

caattttccc ttgagtttcc ttctccacgt aattgttgat ctgtttcttg gcctcttcgg    840

tgtcctcaaa gttgacagag aaggcttctg agtggtacag ttttttgaca tcctccaaaa    900

acttatccac taccttcagg ctcttgttga ggaacaggcc gttgccggtg gtcagctgga    960

gctggctgtc tggcttgttg agggtatgga ggagttcctg gaagccttca tggacctgag   1020

cctccggaat ctccgtgacg ttgaaattca ggccctccag gatttcactg tgagtgtcag   1080

ccttggtccc cagggagagc attgcaaagg ctgtagcgat gctcactggg gagaagaaga   1140

tattggtgct gttggactgg tgtgccagct ggcggtatag gctgaagccg aactcagcca   1200

ggctgggggt gatcttgttg agggttgggt ggtcctgatc atggtgggat gtatccgtct   1260

tctgggcagc atctccctgg ggatcctcag ccagagagcc ggggagcagg cagcacaggc   1320

ctgccagcag gaggacgccc catgagacag aagatggcat tgtcgattca ccgtcccagg   1380

tcagtggtgg tgcctgaggc tgaggagaca gagccctgtc cttgtccgta tttaagcagt   1440

gggtgcagag gggcaacggg ggaggctgct ggtgaatatt aaccaagatc accccagtta   1500

ccggaggagc aaacagggac taagttcaca ggctgggcgc tgagtcgccc gcccacgctg   1560

tccggacgct ctgcctgagc agcatacagc ctccactgca cgtaccaaaa ggagtcattg   1620

tacctggctc agaaaccaca gtgtcctgcg tccaaggtgg agggggtggc gtgagtcagc   1680

cagtcgctgg gagagtacca ctttgctggc cctctgctct cactgcagaa tccttagcgg   1740

ctgttccact ggtagcaaga tctaccattt actaattcac cccgaaatgc ctgatgctga   1800
```

agactgatgc cgccctggaa ttcctggcag cagcagtggc taggccttcc tcagagtgct 1860
gatcccctcc tcctcctttg ctcagctcag tactctgagg gttgctgcgt ggaggcagtg 1920
cacgccctgg gcacagggcc cagttcctgc ccacccagga agttggcctc gggtggcggg 1980
tggcggaggc aataggttgg ggaggggcgg ggagcttggg caggaagggg ccttgcccat 2040
tgccaggcag acacaagact gggc 2064

<210> SEQ ID NO 28
<211> LENGTH: 1608
<212> TYPE: DNA
<213> ORGANISM: Macaca mulatta

<400> SEQUENCE: 28
gtttgcagtc acacacgcag gcagggacca gctcaaccct tctttaatgt cattcaggga 60
gggggccagg gatggagggg aggggctgag gagtgacagg cagttatttc tgggtgggat 120
tcaccacttt tcccatgaag aggggagact tggtattttg ttcaatcatt aagaagacaa 180
agggtttgtt gaacttgacc tcggggggaa tagacatggg tatggcctct aaaaacatgg 240
ccccagcagc ttcagtccct ttctcatcga tggtcagcac agccttatgc acggccttgg 300
agagcttcag ggtgcctcc tccgtgatcc ccgagaggtc agccccattg ctgaagacct 360
tagtgatacc caggtggccc aggactgtct tcagatcata ggttccagta atggccagtc 420
tgggtaaatg taagttggca gacctgctgt tttcattttc caggaacttg gtgatgatat 480
catgggtgag ttcattttcc aggtgctgca gtttcccctc atcaggcagg aagaagatgg 540
cggtggcatt gcccaggtat ttcatcagca gcacccagct ggacagcttc tcacagtggt 600
agatgttaaa catgcctaaa cgcctcatca tgggcacctt cacggtggtc gcctggtcca 660
cgtggaagtc ctcttccttg gtggcctcaa cgtcaaaggg tctctcccat ttgcctttaa 720
agaagatgta attcaccaga gcaaaaactg tgtctctgtc aagctccttg accaaatcca 780
caattttccc ttgagtttcc ttctccacgt aattgttgat ctgtttcttg gcctcttcgg 840
tgtcctcaaa gttgacagag aaggcttctg agtggtacag ttttttgaca tcctccaaaa 900
acttatccac taccttcagg ctcttgttga ggaacaggcc gttgccggtg gtcagctgga 960
gctggctgtc tggcttgttg agggtatgga ggagttcctg gaagccttca tggacctgag 1020
cctccggaat ctccgtgacg ttgaaattca ggccctccag gatttcactg tgagtgtcag 1080
ccttggtccc cagggagagc attgcaaagg ctgtagcgat gctcactggg gagaagaaga 1140
tattggtgct gttggactgg tgtgccagct ggcggtatag gctgaagccg aactcagcca 1200
ggctgggggt gatcttgttg agggttgggt ggtcctgatc atggtgggat gtatccgtct 1260
tctgggcagc atctccctgg ggatcctcag ccagagagcc ggggagcagg cagcacaggc 1320
ctgccagcag gaggacgccc catgagacag aagatggcat tgtcctggaa ttcctggcag 1380
cagcagtggc taggccttcc tcagagtgct gatcccctcc tcctcctttg ctcagctcag 1440
tactctgagg gttgctgcgt ggaggcagtg cacgccctgg gcacagggcc cagttcctgc 1500
ccacccagga agttggcctc gggtggcggg tggcggaggc aataggttgg ggaggggcgg 1560
ggagcttggg caggaagggg ccttgcccat tgccaggcag acacaaga 1608

<210> SEQ ID NO 29
<211> LENGTH: 16
<212> TYPE: PRT
<213> ORGANISM: Unknown
<220> FEATURE:

<223> OTHER INFORMATION: Description of Unknown:
RFGF peptide

<400> SEQUENCE: 29

Ala Ala Val Ala Leu Leu Pro Ala Val Leu Leu Ala Leu Leu Ala Pro
1 5 10 15

<210> SEQ ID NO 30
<211> LENGTH: 11
<212> TYPE: PRT
<213> ORGANISM: Unknown
<220> FEATURE:
<223> OTHER INFORMATION: Description of Unknown:
RFGF analogue peptide

<400> SEQUENCE: 30

Ala Ala Leu Leu Pro Val Leu Leu Ala Ala Pro
1 5 10

<210> SEQ ID NO 31
<211> LENGTH: 13
<212> TYPE: PRT
<213> ORGANISM: Human immunodeficiency virus

<400> SEQUENCE: 31

Gly Arg Lys Lys Arg Arg Gln Arg Arg Arg Pro Pro Gln
1 5 10

<210> SEQ ID NO 32
<211> LENGTH: 16
<212> TYPE: PRT
<213> ORGANISM: Drosophila sp.

<400> SEQUENCE: 32

Arg Gln Ile Lys Ile Trp Phe Gln Asn Arg Arg Met Lys Trp Lys Lys
1 5 10 15

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 33
cuucuuaaug auugaacaaa a 21

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 34
uuuugutcaa ucauuaagaa gac 23

<210> SEQ ID NO 35
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 35

cuucuuaaug auugaacaaa a                                              21


<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36

cuucuuaaug auugaacaaa a                                              21


<210> SEQ ID NO 37
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37

uuuuguucaa ucauuaagaa gac                                            23


<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38

uuuugtucaa ucauuaagaa gac                                            23


<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39

uuuugutcaa ucauuaagaa gac                                            23


<210> SEQ ID NO 40

<400> SEQUENCE: 40

000


<210> SEQ ID NO 41

<400> SEQUENCE: 41

000
```

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

-continued

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115

<400> SEQUENCE: 115

000

<210> SEQ ID NO 116

<400> SEQUENCE: 116

000

<210> SEQ ID NO 117

<400> SEQUENCE: 117

000

<210> SEQ ID NO 118

<400> SEQUENCE: 118

000

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

-continued

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

-continued

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

-continued

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301

<400> SEQUENCE: 301

000

<210> SEQ ID NO 302

<400> SEQUENCE: 302

000

<210> SEQ ID NO 303

<400> SEQUENCE: 303

000

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341

000

<210> SEQ ID NO 342

<400> SEQUENCE: 342

000

<210> SEQ ID NO 343

<400> SEQUENCE: 343

000

<210> SEQ ID NO 344

<400> SEQUENCE: 344

000

<210> SEQ ID NO 345

<400> SEQUENCE: 345

000

<210> SEQ ID NO 346

<400> SEQUENCE: 346

000

<210> SEQ ID NO 347

<400> SEQUENCE: 347

000

<210> SEQ ID NO 348

<400> SEQUENCE: 348

000

<210> SEQ ID NO 349

<400> SEQUENCE: 349

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381
<400> SEQUENCE: 381
000

<210> SEQ ID NO 382
<400> SEQUENCE: 382
000

<210> SEQ ID NO 383
<400> SEQUENCE: 383
000

<210> SEQ ID NO 384
<400> SEQUENCE: 384
000

<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

-continued

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 417
cuucuuaaug auugaacaaa a 21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 418
cuucuuaaug auugaacaaa a 21

<210> SEQ ID NO 419
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 419
uuuuguucaa ucauuaagaa gac 23

<210> SEQ ID NO 420
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 420
uuuuguucaa ucauuaagaa gac 23